US009157906B2

(12) United States Patent
Greengard et al.

(10) Patent No.: US 9,157,906 B2
(45) Date of Patent: Oct. 13, 2015

(54) PHOSPHODIESTERASE ACTIVITY AND REGULATION OF PHOSPHODIESTERASE 1B-MEDIATED SIGNALING IN BRAIN

(75) Inventors: Paul Greengard, New York, NY (US); David Repaske, Loveland, OH (US); Gretchen Snyder, Philadelphia, PA (US)

(73) Assignees: THE ROCKEFELLER UNIVERSITY, New York, NY (US); THE CHILDREN'S HOSPITAL MEDICAL CENTER, Cincinnati, OH (US)

(*) Notice: Subject to any disclaimer, the term of this patent is extended or adjusted under 35 U.S.C. 154(b) by 1124 days.

(21) Appl. No.: 12/951,775

(22) Filed: Nov. 22, 2010

(65) Prior Publication Data
US 2013/0239234 A1    Sep. 12, 2013

Related U.S. Application Data

(63) Continuation of application No. 11/801,400, filed on May 8, 2007, now abandoned, which is a continuation of application No. 10/233,449, filed on Sep. 3, 2002, now abandoned.

(60) Provisional application No. 60/316,320, filed on Aug. 31, 2001.

(51) Int. Cl.
*C12Q 1/00* (2006.01)
*G01N 33/573* (2006.01)
*G01N 33/50* (2006.01)
*C12Q 1/44* (2006.01)
*G01N 33/94* (2006.01)
*A61K 31/00* (2006.01)
*A61K 31/137* (2006.01)
*A61K 31/55* (2006.01)
*A61K 49/00* (2006.01)

(52) U.S. Cl.
CPC ............ *G01N 33/5041* (2013.01); *A61K 31/00* (2013.01); *A61K 31/137* (2013.01); *A61K 31/55* (2013.01); *A61K 49/0008* (2013.01); *C12Q 1/44* (2013.01); *G01N 33/9413* (2013.01); *G01N 2333/916* (2013.01); *G01N 2500/04* (2013.01); *G01N 2800/2835* (2013.01)

(58) Field of Classification Search
None
See application file for complete search history.

(56) References Cited

U.S. PATENT DOCUMENTS

| 5,294,612 A | 3/1994 | Bacon et al. |
| 5,393,755 A | 2/1995 | Neustadt et al. |
| 5,719,283 A | 2/1998 | Bell et al. |
| 5,777,195 A | 7/1998 | Fienberg et al. |
| 5,824,683 A | 10/1998 | McKittrick et al. |
| 5,849,770 A | 12/1998 | Head et al. |
| 5,885,834 A | 3/1999 | Epstein |
| 5,939,419 A | 8/1999 | Chackalamannil et al. |
| 5,962,492 A | 10/1999 | Warrellow et al. |
| 6,013,621 A | 1/2000 | Nishi et al. |
| 6,133,273 A | 10/2000 | Gilbert et al. |
| 6,235,742 B1 | 5/2001 | Bell et al. |
| 6,235,746 B1 | 5/2001 | Davis et al. |
| 6,316,444 B1 | 11/2001 | Hunt et al. |
| 6,423,716 B1 | 7/2002 | Matsuno et al. |
| 6,492,371 B2 | 12/2002 | Roylance |
| 6,498,165 B1 | 12/2002 | Armstrong et al. |
| 6,552,029 B1 | 4/2003 | Davis et al. |
| 6,586,423 B2 | 7/2003 | Bilodeau et al. |
| 6,599,908 B1 | 7/2003 | Davis et al. |
| 6,649,908 B2 | 11/2003 | Apffel et al. |
| 6,670,368 B1 | 12/2003 | Breault et al. |
| 6,693,099 B2 | 2/2004 | Degenhardt |
| 6,756,373 B1 | 6/2004 | Allerton et al. |
| 6,969,719 B2 | 11/2005 | Asberom et al. |
| 7,153,824 B2 | 12/2006 | Palmer et al. |
| 7,320,785 B2 | 1/2008 | Greengard et al. |
| 2002/0077274 A1 | 6/2002 | Roylance |
| 2003/0069246 A1 | 4/2003 | Darrow et al. |

(Continued)

FOREIGN PATENT DOCUMENTS

| AU | 2005201482 A1 | 5/2005 |
| DE | 19931206 A1 | 1/2001 |

(Continued)

OTHER PUBLICATIONS

Borisy et al. (J Neurosc 12: 915-923, 1992).*
Reed et al, Mamm Genome 9: 571-576, 1998.*
Abel et al. *Cell* 88: 615-626, 1997.
Ahn et al. *J. Med. Chem.* 40: 2196-2210, 1997.
Alvarez et at, "A Semi automated Method for the Assay of Cyclic Adenosine 5'-Monophosphate Phosphodiesterase," (1996), Analytical Biochemistry, 236: 367-369.
Bach, et al. *Cell* 81: 905-915, 1995.
Bibb et al., "Severe Deficiencies in Dopamine Signaling in Presymptomatic Huntington's Disease Mice," (2000), PNAS, 97:6809-6814.

(Continued)

*Primary Examiner* — Daniel E Kolker
*Assistant Examiner* — Aditi Dutt
(74) *Attorney, Agent, or Firm* — Hoxie & Associates LLC

(57) ABSTRACT

The present invention provides methods and compositions for modulating the activity of phosphodiesterase 1B (PDE1B) in intracellular signaling pathways, including but not limited to, dopamine D1 intracellular signaling pathways. The invention also provides methods and compositions for modulating the activities of intracellular signaling molecules, including, but not limited to, DARPP-32 and GluR1 AMPA receptor, via modulation of PDE1B. The invention also provides pharmaceutical compositions and methods of screening for compounds that modulate PDE1B activity. The invention also provides methods of treating or ameliorating the symptoms of a disorder, including but not limited to a PDE1B-related disorder or a dopamine D1 receptor intracellular signaling pathway disorder, by administering a modulator of PDE1B, preferably, but not limited to, an inhibitor of PDE1B or an agent that decreases the production of PDE1B.

4 Claims, 7 Drawing Sheets

(56) References Cited

U.S. PATENT DOCUMENTS

Figure 1:
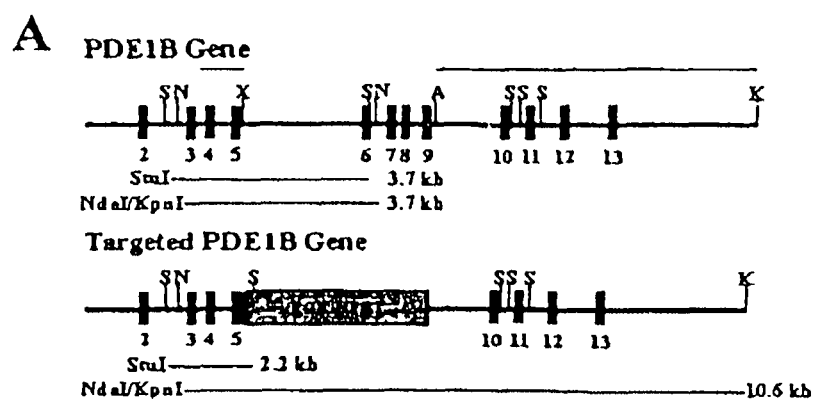
Figure 1:
Figure 1:
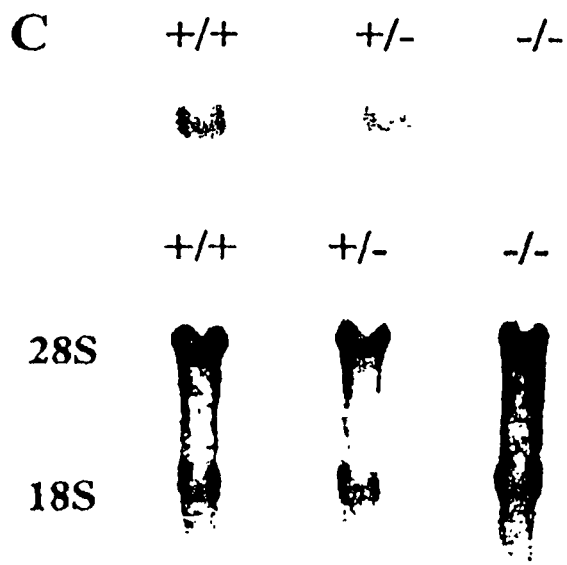

| | | | |
|---|---|---|---|
| 2003/0162782 | A1 | 8/2003 | Grossman et al. |
| 2003/0171255 | A1* | 9/2003 | Greengard et al. ........... 514/1 |
| 2003/0195205 | A1 | 10/2003 | DeNinno |
| 2003/0211040 | A1 | 11/2003 | Greengard et al. |
| 2004/0023989 | A1 | 2/2004 | Fryburg |
| 2004/0087517 | A1 | 5/2004 | Burnet et al. |
| 2005/0048573 | A1 | 3/2005 | Artis et al. |
| 2005/0075795 | A1 | 4/2005 | Pandit |
| 2008/0176961 | A1 | 7/2008 | Greengard et al. |
| 2008/0188492 | A1 | 8/2008 | Li et al. |
| 2008/0193964 | A1 | 8/2008 | Greengard et al. |
| 2008/0194592 | A1 | 8/2008 | Mates et al. |
| 2009/0137549 | A1 | 5/2009 | Edward et al. |
| 2010/0087450 | A1 | 4/2010 | Mates et al. |
| 2010/0173878 | A1 | 7/2010 | Li et al. |
| 2010/0323997 | A1 | 12/2010 | Fienberg et al. |
| 2012/0053190 | A1 | 3/2012 | Fienberg |

FOREIGN PATENT DOCUMENTS

| | | |
|---|---|---|
| EP | 0063381 A1 | 10/1982 |
| EP | 0201188 A2 | 12/1986 |
| EP | 0911333 A1 | 4/2002 |
| GB | A-2151629 | 7/1985 |
| JP | 53031694 A | 3/1978 |
| JP | A-11-043499 | 2/1999 |
| JP | 2000-224992 | 8/2000 |
| WO | WO 91/19717 A1 | 12/1991 |
| WO | WO 94/19351 A1 | 9/1994 |
| WO | WO 97/35989 | 10/1997 |
| WO | WO 98/46606 A1 | 10/1998 |
| WO | WO 98/52568 A1 | 11/1998 |
| WO | WO 99/20273 | 4/1999 |
| WO | WO 00/00197 | 1/2000 |
| WO | WO 00/17345 | 3/2000 |
| WO | WO 01/00851 | 1/2001 |
| WO | WO 01/46145 | 6/2001 |
| WO | WO 02/060428 A2 | 8/2002 |
| WO | WO 03/002567 A1 | 1/2003 |
| WO | WO 03/020702 | 3/2003 |
| WO | WO 03/020702 A2 | 3/2003 |
| WO | WO 03/020724 A1 | 3/2003 |
| WO | WO 03/037432 A1 | 5/2003 |
| WO | WO 03/037899 A1 | 5/2003 |
| WO | WO 03/042216 A1 | 5/2003 |
| WO | WO 2004/056831 A1 | 7/2004 |
| WO | WO 2004/087906 A1 | 10/2004 |
| WO | WO 2006/133261 A2 | 12/2006 |
| WO | WO 2007/025103 A2 | 3/2007 |
| WO | WO 2007/143705 A2 | 12/2007 |
| WO | WO 2008/063505 A1 | 5/2008 |
| WO | WO 2009/073210 A1 | 6/2009 |
| WO | WO 2009/075784 A1 | 6/2009 |

OTHER PUBLICATIONS

Bönöczk et al., Role of sodium channel inhibition in neuroprotection: Effect of vinpocetine, Brain Research Bulletin, 2000, vol. 53, No. 3, pp. 245-254.
Borisy et al. *J. Neurosci.* 12: 915-923, 1992.
Bourtchuladze et al. *Cell* 79: 44-68, 1994—(Abstract only), 59.
Burnouf et al., "Synthesis, Structure-Activity Relationships, and Pharmacological Profile of 9-Amino-4-0xo-I-Phenyl-3,4,5,6,7-Tetrahydrol[I,4JDiazepino[6,7,I-hi]Indoles: Discovery of Potent, Selective Phosphodiesterase Type 4 Inhibitors," (2000), J. Med. Chem., 43: 4850-4867.
Davis et al. *Mol. Cell. Biochem.* 149/150: 271-278, 1995—(Abstract only).
Dousa, Kidney Int 55: 29-62, 1999.
Du et al., "Minocycline Prevents Nigrostriatel Dopaminergic Neurodegeneration in the MPTP Model of Parkinson's Disease," (2001), PNAS, 98:14669-14674.
Duplantier et al., "7-Oxo-4,5,6,7-Tetrahydro-1H-Pyrazolo[3,4-c] Pyridines As Novel Inhibitors of Hyman Eosinophil Phosphodiesterase," (1998), J. Med. Chem., 41:2268-2277.
Erneux et al., "A Mechanism in the Control of Intracellular cAMP Level: The Activation of a Calmodulin-Sensitive Phosphodiesterase by a Rise of Intracellular Free Clacium," (1985), Molecular and Cellular Endocrinology, 43: 123-134.
Escalera et al. *Endo.* 131 (6): 2965-2971, 1992.
Fienberg et al. *Brain Research* 31(2-3): 313-319, 2000.
Fienberg et al., "DARPP-32: Regulator of the Efficacy of Dopaminergic Neurotransmission," (1998), Science, 281: 838-842.
Furuyama et al. *Mol. Brain Res.* 26: 331-336, 1994—(Abstract only).
Gally et al. *Proc. Natl. Acad. Sci. USA* 87: 3547-3551, 1990.
Garthwaite, *J. Trends Neurosci.* 14: 60-67, 1991—(Abstract only).
Greengard et al. Neuron 23: 435-447, 1999.
Guzowski et al. *Proc. Natl. Acad. Sci. USA* 94: 2693-2698, 1997.
Hebb et al. Neuroscience 123: 967-981,2004.
Houslay et al, "The Multienzyme PDE4 Cyclic Adenosine Monophosphate-Specific Phosphodiesterase Family: Intracellular Targeting, Regulation, and Selective Inhibition by Compounds Exerting Anti-Inflammatory and Antidepressant Actions," (1998), Advances in Pharmacology, 44:225-342.
Jaber et al. *Neuropharmacology* 35: 1503-1519, 1996.
Jassen et al. *Mol. Pharmacol.* 70: 71-77, 2006.
Kakkar et al. *Cellular and Molecular Life Sciences*, 55: 1164-1186, 1999.
Kotter, R. *Prog. Neurobiol.* 44: 163-196, 1994—(Abstract only).
Lindskog et al. *Neuroscience* 88: 1005-1008, 1999.
Livingstone et al. *Cell* 37: 205-215, 1984.
Mansuy et al. *Cell* 92: 39-49, 1998.
Mayerhofer, et al. *J. Clin. Endocrin. Metab.* 84(1): 257-264, 1999.
Mayford et al. *Cell* 81: 891-904, 1995.
Nishi et al., Bidirectional Regulation of DARPP-32 Phosphorylation by Dopamine, (1997), The Journal of Neuroscience, 17: 8147-8155.
Polli & Kincaid. *J. Neurosci.* 14: 1251-1261, 1994.
Puckett et al., "Molecular Cloning and Chromosomal Localization of one of the Human Glutamate Receptor Genes," (1997), PNAS, 88:7557-7561.
Qui & Davis. *Genes Dev.* 7: 1447-1458, 1993.
Reed et al. Jour of Neurosci 22: 5188-5197, 2002.
Repaske et al., A Polymerase Chain Reaction Strategy to Identify and Clone Cyclic Nucleotide Phosphodiesterase cDNAs: (1992), The Journal of Biological Chemistry, 267:18683-18688.
Sakakibara et al. *Neuroendo.* 68: 365-373, 1998.
Sharma et al. *J. of Biological Chemistry* 255: 5916-5923, 1979.
Skoulakis, et al. *Neuron.* 11: 197-208, 1993—(Abstract only).
Snyder et al. *J. Neurochem.* 63: 1766-1771, 1994.
Svenningsson et al. *Neuroscience* 84(1): 223-228, 1998.
Svenningsson et al. The AAPS Jour. 7: E353-E360, 2005.
Traficante et al., "Dopamine-Sensitive Adenylate Cyclase and cAMP Phosphodiesterase in Substantia Nigra and Corpus Striatum of Rat Brain," (1976), Life Sciences, 19: 1061-1066.
Tsou et al., Nitric oxide/cGMP pathway stimulates phosphorylation of DARPP-32, a dopamine- and cAMP-regulated phosphoprotein, in the substantia nigra, Proc. Natl. Acad. Sci USA, Apr. 1993, vol. 90, pp. 3462-3465.
Yan et al. *J. Biol. Chem.* 271: 25699-25706, 1996.
Yan et al. *J. Neurosci.* 14: 973-984, 1994.
Yan et al. *Proc. Natl. Acad. Sci. USA.* 92: 9677-9681, 1995.
Yin et al. *Cell* 79: 49-58, 1994—(Abstract only).
Bibb J A et al, "Effects of chronic exposure to cocaine are regulated by the neuronal protein Cdk5" Nature, Nature Publishing Group, London, UK, vol. 410, 2001, p. 376-380.
Cai J X et al: "Dose-dependent effects of the dopamine D1 receptor agonists A77636 or SKF81297 on spatial working memory in aged monkeys.", J. Pharma. Exp. Therap., vol. 283 (1), 1997, p. 183-189.
Allende et al, Comp Biochem Physiol (1987) 88(2):581-587.
Bastia et al, Neurosci Letters (2002) 328:241-244.
Bender et al, Pharrmacol Rev (2006) 58: 488-520.
Chebib et al, Bioorg & Med Chem (2000) 8:2581-2590.
Chermat et al, Pharmacol (1986) 17:348-350.
Dewald et al, J Med Chem (1988) 31:454-461.

(56) References Cited

OTHER PUBLICATIONS

Elvevag et al, Critical Reviews in Neurobiology (2000) 14(1):1-21 (abstract only).
Esfahani et al, Iranian J of Pharmacol and Therapeutics (2002) 1:8-11.
Goldman-Rakic et al, Psychopharmacology (2004) 174:3-16.
Lundqvist et al, Nature (2007) 447:817-822.
Mani et al, Science (1994) 265:1246-1249.
Mani et al, Science (2000) 287:1053-1056.
Morissette et al, Advanced Drug Delivery Reviews (2004) 56:275-300.
Murray et al, JPET (2003) 306:752-762.
Porsolt et al, Nature (1977) 266:730-732.
Poulsen et al, Bioorg & Med Chem Letter (2001) 11:191-193.
Rybalkin et al, Circ Res (2003) 93:280-291.
Turko et al, Mol Pharmacol (1990) 56:124-130.
Uckert et al, J Urology (2004) 171(4):428 (abstract).
Ungerstedt, Acta Physiol Scand Suppl (1971) 367:1-48.
Ungerstedt et al., Brain (1970) 24:485-493.
Vippagunta et al, Advanced Drug Delivery Reviews (2001) 48:3-26.
Lincoln, Molecular Pharmacol (2004) 66:11-13.
Ehrman et al., "Phosphodiesterase 1B differentially modulates the effects of methamphetamine on locomotor activity and spatial learning through DARPP32-dependent pathways: evidence from PDE1B-DARPP32 double-knockout mice", *Genes Brain Behav.* Oct. 2006; 5(7):540-51.
Han, P. et al., "The Calcium/Calmodulin-Dependent Phosphodiesterase PDE1C Down-Regulates Glucose-Induced Insulin Secretion", The Journal of Biomedical Chemistry, vol. 274, No. 32, (1999), pp. 22337-22341.
Shimizu, K. et al., "Calmodulin-Dependent Cyclic Nucleotide Phosphodiesterase (PDE1) is a Pharmalogical arget of Differentiation-Inducing Factor-1, an Antitumor Agent Isolated from Dictyostelium", Cancer Res., (Apr. 1, 2004), vol. 64, No. 7, pp. 2568-2571.
Vatter, S. et al., "Differential Phosphodiesterase Expression and Cytosolic $Ca^{2+}$ in Human CNS Tumour Cells and in Non-Malignant and Malignant Cells of Rat Origin", Journal of Neurochemistry, (2005), vol. 93, pp. 321-329.
Kruuse, et al., "Phosphodiesterase 5 and effects of sildenafil on cerebral arteries of man and guinea pig" *European Journal of Pharmacology*, Elsevier BV, NL, vol. 521, No. 1-3, 3, pp. 105-114 (Oct. 2005).
Hamilton, et al., "Synthesis and Structure-Activity Relationships of Pyrazoloú3/4 Pyrimidin-7-Ones As Adenosine Receptor Antagonists" Journal of Medicinal Chemistry, American Chemical Society, Washington, US, vol. 30, No. 1, pp. 91-96 (1987).
Xia, et al., J Med Chem (1997) 40:4372-4377.

* cited by examiner

PHOSPHODIESTERASE ACTIVITY AND REGULATION OF PHOSPHODIESTERASE 1B-MEDIATED SIGNALING IN BRAIN

RELATED APPLICATIONS

This application is a continuation application of U.S. application Ser. No. 11/801,400, filed May 8, 2007 which is now abandoned, which is a continuation application of U.S. application Ser. No. 10/233,449, filed Sep. 3, 2002 which is now abandoned, which claims benefit, under 35 U.S.C. §119(e), of U.S. provisional application No. 60/316,320, filed on Aug. 31, 2001, the contents of each of which are incorporated herein by reference in their entireties.

This invention was made with Government support under grant number MH 40899 awarded by the National Institute of Mental Health. The United States Government has certain rights in the invention.

1. TECHNICAL FIELD

The present invention relates to methods and compositions for modulating the activity of phosphodiesterase 1B (PDE1B) in intracellular signaling pathways, including but not limited to, dopamine D1 intracellular signaling pathways. The invention also relates to methods and compositions for modulating the activities of intracellular signaling molecules, including, but not limited to, DARPP-32 and GluR1 AMPA receptor, via modulation of PDE1B. The invention also relates to pharmaceutical compositions and methods of screening for compounds that modulate PDE1B activity. The invention also relates to methods of treating or ameliorating the symptoms of a disorder, including but not limited to a PDE1B-related disorder or a dopamine D1 receptor intracellular signaling pathway disorder, by administering a modulator of PDE1B, preferably, but not limited to, an inhibitor of PDE1B or an agent that decreases the production of PDE1B.

2. BACKGROUND OF THE INVENTION

Cyclic nucleotides and calcium are the principal second messengers of the signal transduction pathways within an area of the brain known as the basal ganglia or striatum. NMDA-type glutamate receptor activation and/or dopamine D2 receptor activation result in increased intracellular calcium concentrations (Greengard, P. et al. 1999. Neuron 23:435-447; Kotter, R. 1994. Prog. Neurobiol. 44:163-196), leading to activation of effectors such as calmodulin-dependent kinase II (CaMKII) and calcineurin and potentially to activation of calcium and calmodulin-dependent phosphodiesterases (CaM-PDEs). Dopamine D1 or D2 receptor activation leads to adenylyl cyclase activation (and increased cAMP) or inhibition (and decreased cAMP), respectively. Intracellular concentration of cGMP also are increased after dopamine D1 receptor activation and are unchanged or inhibited after D2 receptor activation. Cyclic nucleotides activate protein kinase A (PKA; cAMP-dependent protein kinase) and/or protein kinase G (PKG; cGMP-dependent protein kinase) that phosphorylate downstream signal transduction pathway elements such as DARPP-32 (dopamine and cAMP-regulated phosphoprotein) and cAMP responsive element binding protein (CREB). These signaling pathways are down-regulated by phosphodiesterases (PDEs) by hydrolysis of the cyclic nucleotides to their 5'-monophosphates. Calcium-regulated PDEs that hydrolyze cAMP and/or cGMP are therefore potential interfaces between dopamine-regulated and other intracellular signaling pathways in the basal ganglia (striatum), including but not limited to nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP) and endorphin intracellular signaling pathways.

Long-term potentiation and long-term depression, the major forms of plasticity associated with hippocampally-mediated learning and memory, are also regulated by the cyclic nucleotide and calcium/calmodulin signal transduction cascades, including the activity of PKA (Abel, T. et al. 1997. Cell 88:615-626; Skoulakis, E. M. C. et al. 1993. Neuron 11:197-208), CaMKII (Bach, M. E. et al. 1995. Cell 81:905-915; Mayford, M. et al. 1995. Cell 81:891-904), CREB (Bourtchuladze, R. et al. 1994. Cell 79:59-68; Guzowski, J. F. et al. 1997. Proc. Natl. Acad. Sci. USA 94:2693-2698; Yin, J. C. P. et al. 1994. Cell 79:49-58), and calcineurin (Mansuy, I. M. et al. 1998. Cell 92:39-49). Drosophila mutants have shown altered intracellular levels of cAMP or an altered cAMP signaling pathway with concomitant learning deficits in an olfactory conditioning paradigm (Qui, Y. and R. L. Davis. 1993. Genes Dev. 7:1447-1458; Livingstone, M. S. et al. 1984. Cell 37:205-215; Skoulakis, E. M. C. et al. 1993. Neuron 11:197-208; Davis, R. L. et al. 1995. Mol. Cell. Biochem. 149/150:271-278). The activity of cGMP has also been implicated in learning and memory through the nitric oxide pathway of retrograde signal transduction (Gaily, J. A. et al. 1990. Proc. Natl. Acad. Sci. USA 87:3547-3551; Garthwaite, J. 1991. Trends Neurosci. 14:60-67).

Ten families of PDEs have been identified but only Family I, the calmodulin-dependent phosphodiesterases (CaM-PDEs) have been shown to act as a potential point of interaction between the calcium and cyclic nucleotide signaling pathways. The three known CaM-PDE genes, PDE1A, PDE1B, and PDE1C, are all expressed in central nervous system tissue. PDE1A is expressed throughout the brain with higher levels of expression in the CA1 to CA3 layers of the hippocampus and cerebellum and at a low level in the striatum (Borisy, F. F. et al. 1992. J. Neurosci. 12:915-923; Yan, C. et al. 1994. J. Neurosci. 14:973-984). PDE1B is predominately expressed in the striatum, dentate gyrus, olfactory tract and cerebellum and its expression has been correlated with brain regions having high levels of dopaminergic innervation (Furuyama, T. et al. 1994. Mol. Brain. Res. 26:331-336; Polli, J. W. and R. L. Kincaid. 1994. J. Neurosci. 14:1251-1261; Yan, C. et al. 1994. J. Neurosci. 14:973-984). PDE1C is primarily expressed in olfactory epithelium, cerebellar granule cells, and striatum (Yan, C. et al. 1995. Proc. Natl. Acad. Sci. USA 92:9677-9681; Yan, C. et al. 1996. J. Biol. Chem. 271:25699-25706). While expression patterns have been extensively studied, a physiological role for the CaM-PDEs in the brain has not been established.

Therefore, there is a need in the art to provide new methods of screening that can be used to develop novel compositions or drugs that can be used to treat diseases or disorders related to the regulation of phosphodiesterases in the nervous system. Furthermore, there is a need to develop treatments for such diseases or disorders that are due, at least in part, to an aberration or dysregulation of an intracellular signaling pathway regulated by phosphodiesterases. The present invention provides such methods and compositions.

Citation or identification of any reference in Section 2, or in any other section of this application, shall not be considered an admission that such reference is available as prior art to the present invention.

3. SUMMARY OF THE INVENTION

The present invention is based on the surprising discovery, on the part of the inventors, that phosphodiesterase (PDE)

activity, in particular, phosphodiesterase 1B (PDE1B) activity, functions in brain tissue as a regulator of locomotor activity and learning and memory. According to the invention, PDE1B may be used a therapeutic target for regulation of intracellular signaling pathways, preferably in the nervous system, including but not limited to a dopamine D1 receptor, dopamine D2 receptor, nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP) or endorphin intracellular signaling pathway. In preferred embodiments, PDE1B may be used as a therapeutic target for treatment of, e.g., a PDE1B-related disorder or a dopamine D1 receptor intracellular pathway disorder. In a specific embodiment, PDE1B may be used as a therapeutic target for treatment of Parkinson's disease.

The invention provides a method for modulating PDE1B activity in a cell or tissue comprising contacting said cell or tissue with an amount of a compound sufficient to modulate activity of a dopamine D1 intracellular signaling pathway, wherein contact of said cell or tissue with the compound results in modulation of PDE1B activity. In certain embodiments, the compound binds to PDE1B. In other embodiments, the compound alters expression of PDE1B. In other embodiments, phosphorylation of phospho-Thr34 of DARPP-32 (hereinafter "phospho-Thr34") or phospho-Ser845 of GluR1 AMPA receptor (hereinafter "phospho-Ser845") is modulated.

The invention also provides a method for treating a disorder, including but not limited to a PDE1B-related disorder and a dopamine D1 receptor intracellular signaling pathway disorder, in a patient in need thereof, comprising administering to the patient an agent that alters the activity of PDE1B, wherein PDE1B activity modulates phosphorylation of DARPP-32 and/or the GluR1 AMPA receptor.

The present invention provides methods for treating a disorder, including but not limited to a PDE1B-related and dopamine D1 receptor intracellular signaling pathway disorder, in an individual (e.g., a patient) or an animal subject by administering an effective amount of a compound of the invention to modulate PDE1B activity. In one embodiment, the agent promotes or increases the activity of PDE1B. In another embodiment, the agent inhibits or decreases the activity of PDE1B. In certain embodiments, the agent promotes (or increases) or inhibits (or decreases) the activity of a dopamine D1 receptor intracellular signaling pathway via modulation of PDE1B activity.

In certain embodiments, the invention provides a method for treating a disorder, including, but not limited to, a PDE1B-related and a dopamine D1 receptor intracellular signaling pathway disorder, in a patient in need thereof, comprising administering to the patient an agent that modulates PDE1B activity, wherein the phosphorylation of DARPP-32 at Thr34, and/or the phosphorylation of GluR1 AMPA receptor at Ser845, is modulated. In specific embodiments, the agent modulates the activity of PDE1B by binding to PDE1B.

In one embodiment, a subject in need of such treatment is administered an amount of a compound of the present invention sufficient to modulate PDE1B activity, and modulate DARPP-32 activity, GluR1 AMPA receptor activity, and/or the activity of a intracellular signaling pathway including, but not limited to a dopamine D1 receptor, dopamine D2 receptor, nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP) or endorphin intracellular signaling pathway.

The invention also provides a method of identifying a compound that modulates PDE1B activity in a dopamine D1 receptor intracellular signaling pathway in a cell or tissue comprising:
(a) determining a first level of PDE1B activity in said cell or tissue;
(b) contacting said cell or tissue with a test compound; and
(c) determining a second level of PDE1B activity in said cell or tissue,
wherein a difference in said first level and said second level of PDE1B activity is indicative of the ability of said test compound to modulate PDE1B activity. In certain embodiments, phosphorylation of phospho-Thr34 of DARPP-32 (hereinafter "phospho-Thr34") or phospho-Ser845 of GluR1 AMPA receptor (hereinafter "phospho-Ser845") is modulated. In other embodiments, the difference in PDE1B activity is indicative of the ability of said test compound to modulate phosphorylation-dependent activation of DARPP-32 or GluR1 AMPA receptor. In other embodiments, the difference in PDE1B activity is indicative of the ability of said test compound to modulate phosphorylation-dependent activation of ARPP-16, ARPP-19, ARPP-21, CREB, cAMP, cGMP, CK1, CK2, Cdk5, PKA, PKG, PP-2C, PP-2B, PP-1, calcium channels, Na/K ATPase or NMDA receptor.

The invention also provides a method of identifying a compound that modulates activity of a dopamine D1 receptor intracellular signaling pathway in a cell or tissue comprising:
(a) determining a first level of activity of PDE1B in said cell or tissue;
(b) contacting said cell or tissue with a test compound; and
(c) determining a second level of activity of PDE1B in said cell or tissue,
wherein a difference in said first level and said second level of PDE1B activity is indicative of the ability of said test compound to modulate activity of said pathway. In certain embodiments, phosphorylation of phospho-Thr34 of DARPP-32 (hereinafter "phospho-Thr34") or phospho-Ser845 of GluR1 AMPA receptor (hereinafter "phospho-Ser845") is modulated. In other embodiments, the difference in PDE1B activity is indicative of the ability of said test compound to modulate phosphorylation-dependent activation of DARPP-32 or GluR1 AMPA receptor. In other embodiments, the difference in PDE1B activity is indicative of the ability of said test compound to modulate phosphorylation-dependent activation of ARPP-16, ARPP-19, ARPP-21, CREB, cAMP, cGMP, CK1, CK2, Cdk5, PKA, PKG, PP-2C, PP-2B, PP-1, calcium channels, Na/K ATPase or NMDA receptor.

The invention also provides a method of identifying a compound that modulates activity of a dopamine. D2 receptor, nitric oxide, noradrenergic, neurotensin, CCK, VIP, serotonin, glutamate, GABA, acetylcholine, adenosine, cannabinoid receptor, natriuretic peptide or endorphin intracellular signaling pathway in a cell or tissue comprising:
(a) determining a first level of activity of PDE1B in said cell or tissue;
(b) contacting said cell or tissue with a test compound; and
(c) determining a second level of activity of PDE1B in said cell or tissue,
wherein a difference in said first level and said second level of PDE1B activity is indicative of the ability of said test compound to modulate activity of said pathway. In certain embodiments, phosphorylation of phospho-Thr34 of DARPP-32 (hereinafter "phospho-Thr34") or phospho-Ser845 of GluR1 AMPA receptor (hereinafter "phospho-Ser845") is modulated.

The invention also provides a method of identifying a compound that modulates activity of a dopamine D1 receptor intracellular signaling pathway in a cell or tissue comprising:
(a) contacting said cell or tissue with a test compound; and
(b) determining a level of activity of PDE1B in said cell or tissue;
wherein a difference in said level and a control level of PDE1B activity in a comparable cell or tissue not contacted with the test compound is indicative of the ability of said test compound to modulate activity of said pathway. In certain embodiments, the difference in said level and said control level of PDE1B activity is indicative of the ability of said test compound to modulate phosphorylation-dependent activation of DARPP-32 or GluR1 AMPA receptor. In other embodiments, the difference in PDE1B activity is indicative of the ability of said test compound to modulate phosphorylation-dependent activation of ARPP-16, ARPP-19, ARPP-21, CREB, cAMP, cGMP, CK1, CK2, Cdk5, PKA, PKG, PP-2C, PP-2B, PP-1, calcium channels, Na/K ATPase or NMDA receptor. In other embodiments, the difference in said level and said control level of PDE1B activity is indicative of the ability of said test compound to modulate activity of a dopamine D2 receptor, nitric oxide, noradrenergic, neurotensin, CCK, VIP, serotonin, glutamate, GABA, acetylcholine, adenosine, cannabinoid receptor, natriuretic peptide or endorphin intracellular signaling pathway.

The invention also provides a method of identifying a compound that modulates PDE1B activity in a dopamine D1 receptor intracellular signaling pathway in a cell or tissue comprising:
(a) contacting said cell or tissue with a test compound; and
(b) determining a level of PDE1B activity in said cell or tissue;
wherein a difference in said level and a control level of PDE1B activity in a comparable cell or tissue not contacted with the test compound is indicative of the ability of said test compound to modulate PDE1B activity. In certain embodiments, the difference in said level and said control level of PDE1B activity is indicative of the ability of said test compound to modulate phosphorylation-dependent activation of DARPP-32 or GluR1 AMPA receptor. In other embodiments, the difference in PDE1B activity is indicative of the ability of said test compound to modulate phosphorylation-dependent activation of ARPP-16, ARPP-19, ARPP-21, CREB, cAMP, cGMP, CK1, CK2, Cdk5, PKA, PKG, PP-2C, PP-2B, PP-1, calcium channels, Na/K ATPase or NMDA receptor. In other embodiments, the difference in said level and said control level of PDE1B activity is indicative of the ability of said test compound to modulate activity of a dopamine D1 receptor, dopamine D2 receptor, nitric oxide, noradrenergic, neurotensin, CCK, VIP, serotonin, glutamate, GABA, acetylcholine, adenosine, cannabinoid receptor, natriuretic peptide or endorphin intracellular signaling pathway.

The invention also provides a method for identifying an agent to be tested for an ability to treat a PDE1B-related or dopamine D1 receptor intracellular signaling pathway disorder in a patient in need of such treatment comprising:
(a) contacting in a cell or tissue PDE1B and Thr34-dephosphorylated DARPP-32 with a potential agent; and
(b) detecting the amount of phosphorylation of Thr34-dephosphorylated DARPP-32,
wherein the agent is identified if an increase in the phosphorylation of Thr34-dephosphorylated DARPP-32 is detected in the presence of the potential agent. In certain embodiments, the ability to treat the PDE1B-related or dopamine D1 receptor intracellular signaling pathway disorder is tested.

The invention also provides a method for identifying an agent to be tested for an ability to treat a PDE1B-related or dopamine D1 receptor intracellular signaling pathway disorder in a patient in need of such treatment comprising:
(a) contacting in a cell or tissue PDE1B and Ser845-dephosphorylated GluR1 AMPA receptor with a potential agent; and
(b) detecting the amount of phosphorylation of Ser845-dephosphorylated GluR1 AMPA receptor,
wherein the agent is identified if an increase in the phosphorylation of Ser845-dephosphorylated GluR1 AMPA receptor is detected in the presence of the potential agent. In certain embodiments, the ability to treat the PDE1B-related or dopamine D1 receptor intracellular signaling pathway disorder is tested.

The invention also provides a method for identifying an agent to be tested for an ability to modulate activity of a dopamine D1 receptor intracellular signaling pathway in a cell or tissue comprising:
(a) determining a first level of PDE1B activity in said cell or tissue;
(b) contacting said cell or tissue with a potential agent; and
(c) determining a second level of PDE1B activity in said cell or tissue,
wherein a difference in said first level and said second level of PDE1B activity is indicative of the ability of said potential agent to modulate activity of the dopamine D1 receptor intracellular signaling pathway. In certain embodiments, the method comprises the additional step of:
(d) determining whether the dopamine D1 receptor intracellular signaling pathway is modulated.

The invention also provides a method for identifying an agent to be tested for an ability to modulate activity of a dopamine D2 receptor, nitric oxide, noradrenergic, neurotensin, CCK, VIP, serotonin, glutamate, GABA, acetylcholine, adenosine, cannabinoid receptor, natriuretic peptide or endorphin intracellular signaling pathway intracellular signaling pathway in a cell or tissue comprising:
(a) determining a first level of PDE1B activity in said cell or tissue;
(b) contacting said cell or tissue with a potential agent; and
(c) determining a second level of PDE1B activity in said cell or tissue,
wherein a difference in said first level and said second level of PDE1B activity is indicative of the ability of said potential agent to modulate activity of said intracellular signaling pathway. In certain embodiments, the method comprises the additional step of:
(d) determining whether said intracellular signaling pathway is modulated.

The invention also provides a method for identifying an agent to be tested for an ability to modulate activity of a dopamine D1 receptor intracellular signaling pathway in a cell or tissue comprising:
(a) contacting said cell or tissue with a potential agent; and
(b) determining a level of PDE1B activity in said cell or tissue;
wherein a difference in said level and a control level of PDE1B activity in a comparable cell or tissue not contacted with the test compound is indicative of the ability of said test compound to modulate activity of the dopamine D1 receptor intracellular signaling pathway. In certain embodiments, the method comprises the additional step of:
(c) determining whether activity of the dopamine D1 receptor intracellular signaling pathway is modulated.

The invention also provides a method for identifying an agent to be tested for an ability to modulate activity of a dopamine D2 receptor, nitric oxide, noradrenergic, neurotensin, CCK, VIP, serotonin, glutamate, GABA, acetylcholine, adenosine, cannabinoid receptor, natriuretic peptide or endorphin intracellular signaling pathway intracellular signaling pathway in a cell or tissue comprising:
    (a) contacting said cell or tissue with a potential agent; and
    (b) determining a level of PDE1B activity in said cell or tissue,
wherein a difference in said level and a control level of PDE1B activity in a comparable cell or tissue not contacted with the test compound is indicative of the ability of said test compound to modulate activity of said intracellular signaling pathway. In certain embodiments, the method comprises the additional step of
    (d) determining whether the activity of said intracellular signaling pathway is modulated.

The invention also provides a method for selecting a potential therapeutic agent for use in the treatment of a PDE1B-related or dopamine D1 receptor intracellular signaling pathway disorder, comprising:
    (a) administering a potential therapeutic agent to an animal;
    (b) measuring the response of said animal to said potential therapeutic agent;
    (c) comparing the response of said animal with that of a control animal to which the potential therapeutic agent has not been administered; and
    (d) selecting a potential therapeutic agent based on the difference in responses observed between said animal and said control animal.
In certain embodiments, the animal is a mouse. In other embodiments, the disorder is Parkinson's disease.

The invention also provides a method for selecting a potential therapeutic agent for use in the treatment of a PDE1B-related or dopamine D1 receptor intracellular signaling pathway disorder, comprising:
    (a) administering a potential therapeutic agent, to an animal;
    (b) measuring the response of said animal to administration of a neurotransmitter that interacts with a dopamine D1 receptor intracellular signaling pathway;
    (c) comparing the response of said animal with that of a control animal to which the potential therapeutic agent has not been administered; and
    (d) selecting a potential therapeutic agent based on the difference in responses observed between said animal and said control animal.
In certain embodiments, the animal is a mouse. In other embodiments, the disorder is Parkinson's disease.

The invention also provides a method for selecting a potential therapeutic agent for use in the treatment of a PDE1B-related or dopamine D1 receptor intracellular signaling pathway disorder, comprising:
    (a) administering a potential therapeutic agent to an animal;
    (b) measuring the response of said animal to dopamine administration;
    (c) comparing the response to dopamine administration of said animal with that of a control animal to which the potential therapeutic agent has not been administered; and
    (d) selecting a potential therapeutic agent based on the difference in responses observed between said animal and said control animal.
In certain embodiments, the animal is a mouse. In other embodiments, the disorder is Parkinson's disease.

The invention also provides a method for selecting a potential therapeutic agent for use in the treatment of a PDE1B-related or dopamine D1 receptor intracellular signaling pathway disorder, comprising:
    (a) administering a potential therapeutic agent to an animal;
    (b) measuring the response of said animal, wherein the response is selected from the group consisting of:
        (i) exhibition of exploratory behavior during a test period for horizontal locomotor activity;
        (ii) exhibition of hyperactivity after administration of methamphetamine treatment;
        (iii) path length in acquisition of a Morris water maze;
        (iv) change in level of phospho-Thr34 or phospho-Ser845 in striatal slices from said animal; and
        (v) change in level of phospho-Thr34 or phospho-Ser845 in nucleus accumbens slices from said animal,
    (c) comparing the response of said animal with that of a control animal to which the potential therapeutic agent has not been administered; and
    (d) selecting a potential therapeutic agent based on the difference in responses observed between said animal and said control animal.
In certain embodiments, the animal is a mouse. In other embodiments, the disorder is Parkinson's disease.

The invention also provides an animal model for testing compounds identified by the screening method of the present invention, wherein the compound is tested for functional utility using the animal model of the present invention. In a preferred embodiment, the invention provides an animal model that is a PDE1B-deficient, e.g., null or "knockout" mouse. In one embodiment, the invention provides a transgenic knockout mouse comprising a homozygous disruption in its endogenous PDE1B gene, wherein said disruption prevents the expression of a functional PDE1B protein, and further wherein the phenotype of said knockout mouse relative to a mouse having a wild type PDE1B gene comprises absence of PDE1B enzymatic activity when assayed for cAMP or cGMP hydrolysis. In certain embodiments, the disruption comprises a targeted disruption of the PDE1B catalytic site. In other embodiments, the phenotype of the PDE1B knockout mouse relative to a mouse having a wild type PDE1B gene further comprises a phenotype selected from the group consisting of: exhibition of significantly more exploratory behavior during the first 30 minutes of a test period for horizontal locomotor activity, exhibition of significantly more hyperactivity after administration of methamphetamine treatment, exhibition of significantly longer path length in acquisition of a Morris water maze, exhibition in striatal slices from said mouse of increased levels of phospho-Thr34 or phospho-Ser845 upon administration of a D1 receptor agonist, and exhibition in nucleus accumbens slices from said mouse of increased levels of phospho-Thr34 or phospho-Ser845 upon administration of a D1 receptor agonist.

3.1. Definitions

As used herein, the term "modulate" or "modulation" shall have its usual meaning, and encompasses the meanings of the words "enhance," "inhibit," and "mimic." "Modulation" of activity may be either an increase or a decrease in activity.

As used herein, an "agonist" is any compound that acts directly or indirectly through or upon a receptor to produce a pharmacological effect, while an "antagonist" is any compound that blocks the stimulation of a receptor and its resulting pharmacological effect.

As used herein, an "effective amount" of a modulatory compound is an amount that can be determined by one of skill in the art based on data from studies using methods of analysis such as those disclosed herein. Such data may include, but not be limited to, results from IC50 determinations, as discussed hereinbelow.

As used herein, the term "DARPP-32" is used interchangeably with "Dopamine- and cyclic AMP (cAMP)-Regulated PhosphoProtein" and "DARPP32" and is a 32 kilodalton cytosolic protein that is selectively enriched in medium-sized spiny neurons in neostriatum. The human, mouse, rat and bovine DARPP-32 amino acid sequences are disclosed in U.S. patent application Ser. Nos. 09/419,379, by Bibb et al., entitled "Methods of Identifying Agents That Regulate Phosphorylation/Dephosphorylation in Dopamine Signaling," filed Oct. 15, 1999, and 09/687,959, by Bibb et al., entitled "Methods of Identifying Agents That Regulate Phosphorylation/Dephosphorylation in Dopamine Signaling," filed Oct. 13, 2000, incorporated herein by reference in their entireties (see SEQ ID NOS: 1-4, respectively).

As used herein, the term "Thr75 DARPP-32" is used interchangeably with "Thr75 DARPP32," "thr$^{75}$ DARPP-32", "Threonine-75 DARPP-32" and "threonine-75 DARPP-32" along with analogous abbreviations, and denotes the seventy-fifth amino acid residue in the amino acid sequence of DARPP-32 as disclosed by Brene et al. (J. Neurosci. 14:985-998 (1994)) having the GenBank Accession of AAB30129.1, which is a threonine residue that can be phosphorylated by Cdk5 and dephosphorylated by protein phosphatase 2A (PP2A).

As used herein, the term "Thr75DARPP-32" denotes the seventy-fifth amino acid residue in the amino acid sequence of human DARPP-32. Unless otherwise indicated, the term can also refer to a corresponding amino acid residue in the DARPP-32 from another species, e.g., murine, bovine, etc. These sequences are well-known to one of skill in the art, and using routine methods, the corresponding amino acid residue can be identified.

As used herein, the term "phospho-Thr75 DARPP-32," or analogous abbreviations, as disclosed above, denotes the phosphorylated form of Thr75 DARPP-32.
DARPP-32.

As used herein, the term "Cdk5 phosphorylatable fragment of DARPP-32" is a protein fragment of DARPP-32 that contains a threonine residue that, when in the dephosphorylated form, can be phosphorylated by Cdk5 and dephosphorylated by protein phosphatase 2A (PP2A). For human DARPP-32 having the amino acid sequence of SEQ ID NO:1, the threonine residue is preferably Thr75 DARPP-32. Such fragments can be between about 5 and 100 residues, or more preferably between about 10 and 50 residues. For example, in a particular embodiment, the peptide fragment comprises 5 consecutive amino acids from SEQ ID NO: 1 including Thr75. In another embodiment of this type, the peptide fragment comprises 7 consecutive amino acids from SEQ ID NO: 1 including Thr75. In an alternative embodiment the peptide fragment comprises between 10 and 25 consecutive amino acids from SEQ ID NO: 1 including Thr75. All of the peptide fragments can be part of fusion peptides or proteins. A Cdk5 phosphorylatable fragment of DARPP-32 can be prepared by any method commonly known in the art, e.g., cleaving (such as with a protease) and by dephosphorylating the phosphorylated fragment or by cleaving (such as with a protease) the dephosphorylated fragment from a larger fragment of Thr75-DARPP-32 protein or from the full-length DARPP-32 protein. Thus, the fragments can be synthesized by either standard peptide synthesis disclosed below, or generated through recombinant DNA technology or by classical proteolysis.

As used herein, the term "Thr34 DARPP-32" is used interchangeably with "Thr34 DARPP32," "thr$^{34}$ DARPP-32" "Threonine-34 DARPP-32" and "threonine-34 DARPP-32" along with analogous abbreviations and denotes the thirty-fourth amino acid residue of the amino acid sequence of DARPP-32 as disclosed by Brene et al. (J. Neurosci. 14:985-998 (1994)) having the GenBank Accession No. of AAB30129.1, which is a threonine residue that can be phosphorylated by the cyclic AMP dependent protein kinase (PKA) or dephosphorylated by protein phosphatase 2B (PP2B).

As used herein, the term "Thr34DARPP-32" denotes the thirty-fourth amino acid residue in the amino acid sequence of human DARPP-32. Unless otherwise indicated, the term can also refer to a corresponding amino acid residue in the DARPP-32 from another species, e.g., murine, bovine, etc. These sequences are well-known to one of skill in the art, and using routine methods, the corresponding amino acid residue can be identified.

As used herein, the term "phospho-Thr34 DARPP-32," or analogous abbreviations as disclosed above, denotes the phosphorylated form of Thr34 DARPP-32.

As used herein, the term "PKA phosphorylatable fragment of DARPP-32" is a protein fragment of DARPP-32 that contains a threonine residue that, when in the dephosphorylated form, can be phosphorylated by PKA. For human DARPP-32 having the amino acid sequence of SEQ ID NO:1, the threonine residue is preferably Thr34 DARPP-32. Such fragments can be between about 5 and 100 residues, or more preferably between about 10 and 50 residues. For example, in a particular embodiment, the peptide fragment comprises 5 consecutive amino acids from SEQ ID NO: 1 including Thr34. In another embodiment of this type, the peptide fragment comprises 7 consecutive amino acids from SEQ ID NO: 1 including Thr34. In an alternative embodiment the peptide fragment comprises between 10 and 25 consecutive amino acids from SEQ ID NO: 1 including Thr34. All of the peptide fragments can be part of fusion peptides or proteins. A PKA phosphorylatable fragment of DARPP-32 can be prepared by any method commonly known in the art, e.g., cleaving (such as with a protease) and by dephosphorylating the phosphorylated fragment or by cleaving (such as with a protease) the dephosphorylated fragment from a larger fragment of Thr34-DARPP-32 protein or from the full-length DARPP-32 protein. Thus, the fragments can be synthesized by either standard peptide synthesis disclosed below, or generated through recombinant DNA technology or by classical proteolysis.

As used herein, the term "Ser845 GluR1AMPA receptor" is used interchangeably with "Ser845-GluR1AMPA receptor," "ser$^{845}$ GluR1 AMPA", "Serine-845 GluR1 AMPA," along with analogous abbreviations and denotes the eight-hundred and forty-fifth amino acid residue of the amino acid sequence of the mature human GluR1 AMPA receptor subunit (i.e., serine 863 of the preprotein sequence as disclosed by Puckett et al. (1991, Molecular cloning and chromosomal localization of one of the human glutamate receptor genes, Proc. Natl. Acad. Sci. U.S.A. 88 (17), 7557-7561) having the GenBank Accession No. of NP_000818 (SEQ ID NO: 7)) which is a serine residue that can be phosphorylated by PKA.

As used herein, the term "Ser845 GluR1AMPA receptor" denotes the eight-hundred and forty-fifth amino acid residue in the amino acid sequence of human mature GluR1 AMPA receptor subunit. Unless otherwise indicated, the term can also refer to a corresponding amino acid residue in the GluR1 AMPA receptor from another species, e.g., murine, bovine, etc. These sequences are well-known to one of skill in the art, and using routine methods, the corresponding amino acid residue can be identified.

As used herein, the term "phospho-Ser845 GluR1AMPA receptor" or analogous abbreviations as disclosed above, denotes the phosphorylated form of Ser845 GluR1AMPA receptor.

As used herein, the term "PKA phosphorylatable fragment of GluR1 AMPA receptor" is a protein fragment of GluR1 AMPA receptor that contains a serine residue that, when in the dephosphorylated form, can be phosphorylated by PKA. For human GluR1AMPA receptor having the amino acid sequence of SEQ ID NO: 7, the serine residue is preferably Ser845 GluR1 AMPA receptor of the mature form (Ser 863 of the preprotein sequence). Such fragments can be between about 5 and 100 residues, or more preferably between about 10 and 50 residues. For example, in a particular embodiment, the peptide fragment comprises 5 consecutive amino acids including Ser845. In another embodiment of this type, the peptide fragment comprises 7 consecutive amino acids including Ser845. In an alternative embodiment the peptide fragment comprises between 10 and 25 consecutive amino acids including Ser845. All of the peptide fragments can be part of fusion peptides or proteins. A PKA phosphorylatable fragment of GluR1AMPA receptor can be prepared by any method commonly known in the art, e.g., cleaving (such as with a protease) and by dephosphorylating the phosphorylated fragment or by cleaving (such as with a protease) the dephosphorylated fragment from a larger fragment of Ser845 GluR1AMPA receptor protein or from the full-length GluR1AMPA receptor protein. Thus, the fragments can be synthesized by either standard peptide synthesis disclosed below, or generated through recombinant DNA technology or by classical proteolysis.

As will be apparent to one of skill in the art, other phosphorylatable and dephosphorylatable fragments of intracellular signaling molecules, including but not limited to DARPP-32 and GluR1 AMPA, may be readily prepared according to methods well known in the art, using the general methods disclosed above.

As used herein, the amount and/or rate of phosphorylation of DARPP-32 or of a phosphorylatable fragment of DARPP-32, as described hereinabove, in a kinase reaction is "significantly changed" when the amount and/or rate of phosphorylation of DARPP-32 or the phosphorylatable fragment of DARPP-32 is increased or decreased by a statistically significant amount, as determined by standard statistical methods known in the art. In another embodiment, the significant change is at least about 10-25%, relative to the control reaction. Preferably, a significant change in rate of the phosphorylation of DARPP-32 by a molecule of interest (e.g., CK1 or Cdk5) observed in the presence of a potential modulator is at some point correlated with the Michaelis constants (e.g., the Vmax or Km) of the reaction. For example, in the case of an inhibitor, a KI can be determined. Thus, in certain embodiments, it may be preferable to study various concentrations of a modulator in a reaction mixture to allow the identification of the potential modulator as a modulator.

As used herein, the amount and/or rate of dephosphorylation of DARPP-32 or of a dephosphorylatable fragment of DARPP-32, as described hereinabove, in a phosphatase reaction is "significantly changed" when the amount and/or rate of dephosphorylation of DARPP-32 or the dephosphorylatable fragment of DARPP-32 is increased or decreased by a statistically significant amount, as determined by standard statistical methods known in the art. In another embodiment, the significant change is at least about 10-25%, relative to the control reaction. Preferably, a significant change in rate of the dephosphorylation of DARPP-32 by a molecule of interest (e.g., PP2C, PP2B or PP2A) observed in the presence of a potential modulator is at some point correlated with the Michaelis constants (e.g., the Vmax or Km) of the reaction. For example, in the case of an inhibitor, a KI can be determined. Thus, in certain embodiments, it may be preferable to study various concentrations of a modulator in a reaction mixture to allow the identification of the potential modulator as a modulator.

As used herein, the term "PDE1B-related disorder," is used interchangeably with the term "phosphodiesterase1B-related disorder," "PDE1B disorder" or analogous terms. A PDE1B-related disorder includes, but is not limited to, Parkinson's disease, Huntington's disease, attention deficit disorder (ADD), attention deficit hyperactivity disorder (ADHD), neurodegenerative disorder, Tourette's syndrome, tic disorder, Lesch-Nyans disease, pain, dystonias, substance or drug abuse, schizophrenia, schizoaffective disorder, depression, affective disorder, manic-depressive disorder, obsessive-compulsive disorder, eating disorder, emesis, panic disorder, anxiety disorder, migraine, myoclonus, premenstrual syndrome (PMS), post-traumatic stress syndrome, carcinoid syndrome, Alzheimer's disease, stroke, epilepsy, sleep or circadian rhythm disorder (e.g., insomnia), sexual disorder, stress disorder, hypertension and cancer. A PDE1B-related disorder also includes, but is not limited to, a disease (e.g., Parkinson's disease) or a condition (e.g., addiction to cocaine) that involves an aberration or dysregulation of a signal transmission pathway, including, but not limited to, neurotransmission mediated by PDE1B in excitable cells, tissues or organs (e.g., neurons, brain, central nervous system, etc.). A PDE1B-related disorder also includes, but is not limited to, a symptom of a PDE1B-related disorder. In certain embodiments, the pathway affected includes the phosphorylation and/or dephosphorylation of DARPP-32, with the corresponding treatment of the dysregulation involving the stimulation and/or inhibition of the phosphorylation and/or dephosphorylation of one or more specific threonine and/or serine residues of DARPP-32 (see, e.g., Greengard et al., Neuron 23:435-447 (1999); Bibb et al., Proc. Natl. Acad. Sci. 97:6809-68 14 (2000); and U.S. patent application Ser. Nos. 09/419,379, by Bibb et al., entitled "Methods of Identifying Agents That Regulate Phosphorylation/Dephosphorylation in Dopamine Signaling," filed Oct. 15, 1999, and 09/687,959, by Bibb et al., entitled "Methods of Identifying Agents That Regulate Phosphorylation/Dephosphorylation in Dopamine Signaling," filed Oct. 13, 2000, each of which is incorporated herein by reference in its entirety). In other embodiments, the pathway affected includes the phosphorylation of phospho-Ser845 of GluR1 AMPA receptor by cAMP-dependent protein kinase (PKA) with the corresponding treatment of the dysregulation involving the stimulation and/or inhibition of the phosphorylation and/or dephosphorylation of one or more specific serine residues of GluR1 AMPA receptor (see, e.g., Kameyama, K. et al. 1998. *Neuron* 21:1163-1175). In yet other embodiments, the pathway affected includes GluR1 subunit of the AMPA receptor as an endpoint of the dopamine pathway. In yet other embodiments, the pathway affected includes other endpoints for the biological effects of dopaminergic intracellular signaling pathways, including but not limited to phosphorylation of several types of calcium channels, the Na/K ATPase, NMDA receptors, CREB, etc., as would be apparent to one of skill in the art.

As used herein, a "dopamine D1 intracellular signaling pathway" is used interchangeably with "D1 receptor intracellular signaling pathway," "dopamine D1 intracellular signaling cascade," "dopamine D1 signaling cascade" or analogous terms.

As used herein, the term "dopamine D1 receptor intracellular signaling pathway disorder," is used interchangeably with the term "D1 receptor intracellular signaling pathway disorder," or analogous terms. A dopamine D1 receptor intracellular signaling pathway disorder includes, but is not limited to Parkinson's disease, Huntington's disease, attention deficit disorder (ADD), attention deficit hyperactivity disorder (ADHD), neurodegenerative disorder, Tourette's syndrome, tic disorder, Lesch-Nyans disease, pain, dystonias, substance or drug abuse, schizophrenia, schizoaffective disorder, depression, affective disorder, manic-depressive disorder, obsessive-compulsive disorder, eating disorder, emesis, panic disorder, anxiety disorder, migraine, myoclonus, premenstrual syndrome (PMS), post-traumatic stress syndrome, carcinoid syndrome, Alzheimer's disease, stroke, epilepsy, sleep or circadian rhythm disorder (e.g., insomnia), sexual disorder, stress disorder, hypertension and cancer. A dopamine D1 receptor intracellular signaling pathway disorder also includes, but is not be limited to, a disease (e.g., Parkinson's disease) or a condition (e.g., addiction to cocaine) that involves an aberration or dysregulation of a signal transmission pathway, including, but not limited to, neurotransmission mediated by dopamine D1 receptors in excitable cells, tissues or organs (e.g., neurons, brain, central nervous system, etc.). A dopamine D1 receptor intracellular signaling pathway disorder also includes, but is not limited to, a symptom of a dopamine D1 receptor intracellular signaling pathway disorder. In certain embodiments, the pathway affected includes the phosphorylation and/or dephosphorylation of DARPP-32, with the corresponding treatment of the dysregulation involving the stimulation and/or inhibition of the phosphorylation and/or dephosphorylation of one or more specific threonine and/or serine residues of DARPP-32 (see, e.g., Greengard et al., Neuron 23:435-447 (1999); Bibb et al., Proc. Natl. Acad. Sci. 97:6809-68 14 (2000); and U.S. patent application Ser. Nos. 09/419,379, by Bibb et al., entitled "Methods of Identifying Agents That Regulate Phosphorylation/Dephosphorylation in Dopamine Signaling," filed Oct. 15, 1999, and 09/687,959, by Bibb et al., entitled "Methods of Identifying Agents That Regulate Phosphorylation/Dephosphorylation in Dopamine Signaling," filed Oct. 13, 2000, each of which is incorporated herein by reference in its entirety). In other embodiments, the pathway affected includes the phosphorylation of phospho-Ser845 of GluR1 AMPA receptor by cAMP-dependent protein kinase (PICA) with the corresponding treatment of the dysregulation involving the stimulation and/or inhibition of the phosphorylation and/or dephosphorylation of one or more specific serine residues of GluR1 AMPA receptor (see, e.g., (Kameyama, K. et al. 1998. Neuron 21:1163-1175).

As used herein, a "small organic molecule" is an organic compound (or organic compound complexed with an inorganic compound (e.g., metal)) that has a molecular weight of less than 3 kilodaltons, preferably less than 1.5 kilodaltons. Preferably, the small organic molecule can cross the blood-brain barrier.

As used herein, the term "about" means within 10 to 15%, preferably within 5 to 10%. For example an amino acid sequence that contains about 60 amino acid residues can contain between 51 to 69 amino acid residues, more preferably 57 to 63 amino acid residues.

4. DESCRIPTION OF THE FIGURES

FIGS. 1A-C. Targeting strategy for PDE1B and Southern and Northern blot analysis of offspring of the third generation backcrossing. A, Schematic of a portion of the endogenous PDE1B gene and the result of homologous recombination with the targeting vector. A 3.1 kb portion of the PDE1B gene encoding the central catalytic domain was disrupted by replacement with the 2.9 kb HPRT gene. Disruption resulted in a size shift in the StuI fragment from 3.7 to 2.2 kb and a size shift in an NdeI/KpnI fragment from 3.7 to 10.6 kb. The bars above the PDE1B gene represent genomic DNA sequences included in the targeting vector. The bars below the PDE1B gene indicate the restriction fragments used for Southern blot analysis of ES cell and mouse genomic DNA. Numbered thick vertical lines represent exons. Thin vertical lines indicate restriction enzyme sites. S, StuI; N, NdeI; X, XbaI; A, AccI; K, KpnI. B, Southern blot of offspring of third generation backcross mice of mouse genomic DNA digested with StuI demonstrating wild-type (W), heterozygous (H), and null (N) genotypes. The 2.2 kb StuI fragment was generated by homologous recombination with the targeting vector. All blots were probed with a PDE1B exon 3 probe. C, Brain total RNA from mice of each genotype was analyzed by Northern blot by hybridizing with K-17, a cDNA probe corresponding to the central catalytic domain (Repaske et al., 1992, J Biol Chem 267:18683-18688). The expected approximately 3.0 kb transcript is observed in the WT and PDE1B+/− mice only (top). The methylene blue-stained ribosomal bands on the same Northern blot demonstrate equal RNA loading (bottom). See Section 6 for details.

Figure 2:
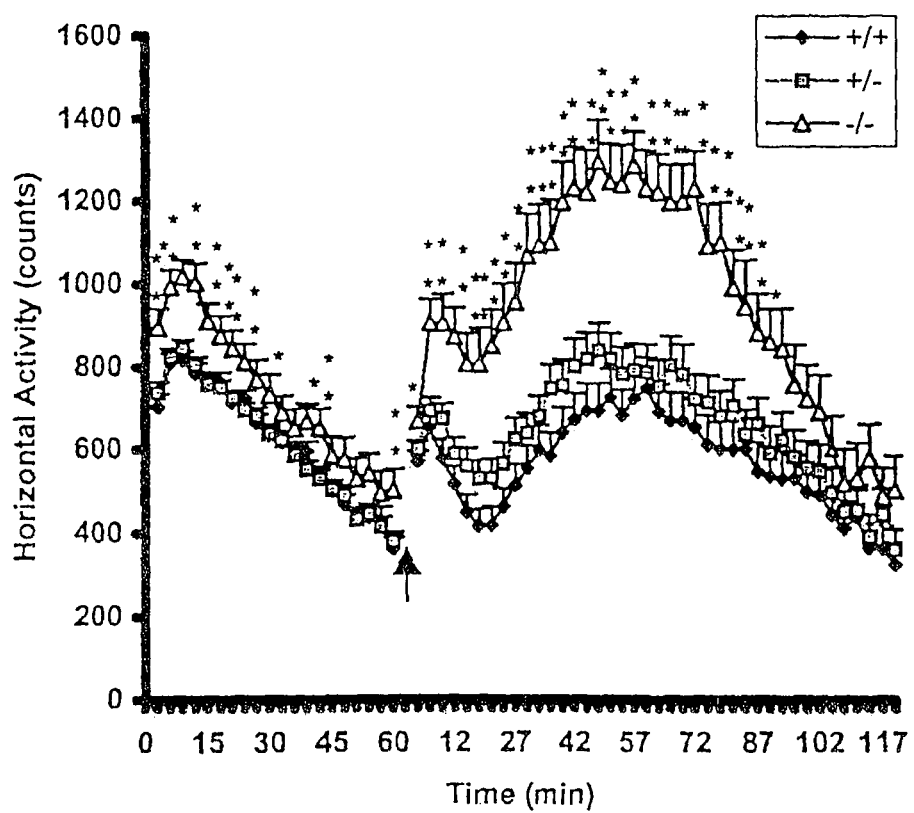

FIG. 2. Horizontal activity. Shown is the mean±SEM horizontal activity for PDE1B−/−, PDE1B+/−, and WT mice (males and females combined). An arrow indicates the time of methamphetamine administration (1 mg/kg). Counts represent the total number of photo beam interruptions per 3 min interval. PDE1B−/− mice were hyperactive compared with WT mice both before ($F_{(2,120)}$=8.55; p<0.0003) and after ($F_{(2,120)}$=11.18; p<0.0001) methamphetamine challenge. *p<0.05; **p<0.01. n=+/+, 71; +/−, 114; −/−, 49. See Section 6 for details.

FIGS. 3A-B. Sex differences in total distance. Shown is the mean±SEM distance traveled by males (top) and females (bottom) in the activity apparatus in 3 min blocks. The arrow indicates time of methamphetamine administration (1 mg/kg). Female PDE1B−/− mice, but not male PDE1B−/− mice, were hyperactive compared with WT mice during the pre-methamphetamine challenge period ($F_{(2,120)}$=3.07; p<0.05); this sex difference did not continue into the postchallenge period. n=+/+, 71; +/−, 114; −/−, 49. See Section 6 for details.

FIGS. 4A-D. Phosphorylation of PKA mediated substrates in WT and PDE1B−/− mice. A, Immunoblot showing level of phospho-Thr 34-DARPP-32 in control (Con) striatal slices and in slices treated with the adenylyl cyclase activator forskolin (For) from WT and PDE1B−/− mice. B, Fold increase in phospho-Thr 34-DARPP-32 in response to forskolin (*p<0.05 compared with WT forskolin; Mann-Whitney U test; n=3 mice per treatment group). C, Immunoblot showing levels of phospho-Thr 34 and total DARPP-32 (left) and phospho-Ser 845 and total GluR1 (right) in untreated (Con) and D1-agonist treated (D1) striatal slices from WT and PDE1B−/− mice. D, Mean±SEM increase in the levels of phospho-Thr 34-DARPP-32 (left) and phospho-Ser 845-GluR1 (right) on incubation with D1 agonist (*p<0.05 compared with untreated control slices; †p<0.05 compared with D1-treated WT slices; Mann-Whitney U test; n=3 mice per treatment group). See Section 6 for details.

FIGS. 5A-B. Spatial learning in the Morris water maze. +, Path length (mean SEM) to reach the platform for mice of each genotype. PDE1B−/− and PDE1B+/− mice showed significantly increased path length compared with WT mice ($F_{(2,112)}$=9.19; p<0.0002). B, Cumulative distance from the platform (mean±SEM) for mice of each genotype. PDE1B−/− and PDE1B+/− mice showed a significantly increased cumulative distance compared with WT mice ($F_{(2,112)}$=8.38; p<0.0004). Data are shown for the average of four trials per day averaged across all 6 d. **p<0.01 compared with wild-type mice. n=+/+, 55; +/−, 101; −/−, 66. See Section 6 for details.

Figure 6:
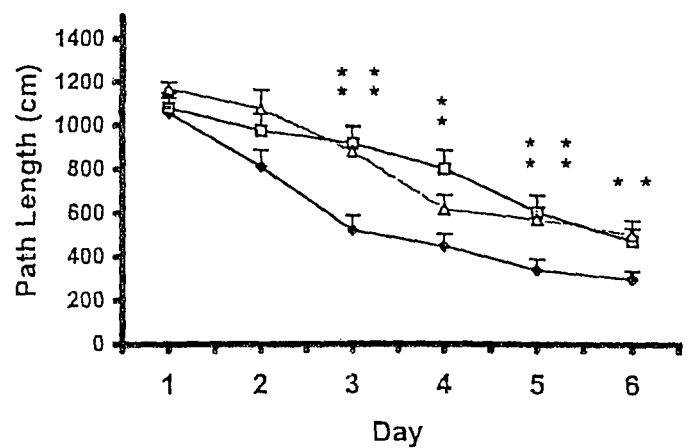

FIG. 6. Spatial learning in the Morris water maze: acquisition of hidden platform task. Data are shown for the average of four trials per day for each of the three genotypes. PDE1B−/− and PDE1B+/− mice showed significantly increased path length compared with WT mice on days 3-6 (genotype by day by platform interaction; $F_{(10,560)}$=2.01; p<0.04). *p<0.05 and **p<0.01 compared with WT mice. Filled diamonds, +/+ (n=55); shaded squares, +/− (n=101); open triangles, −/− (n=66). See Section 6 for details.

Figure 7:
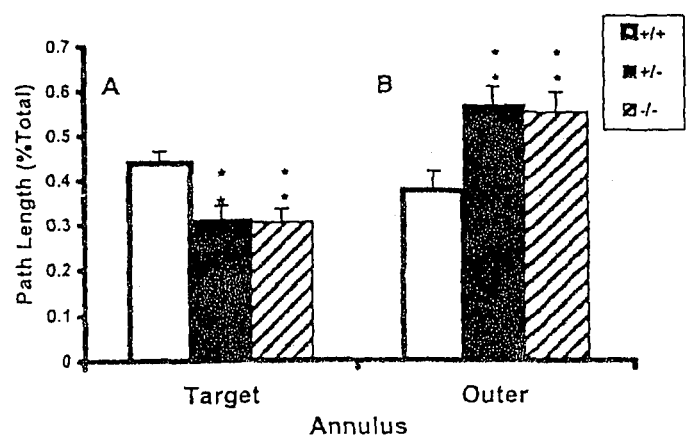

FIGS. 7A-B. Spatial memory in the Morris water maze: probe trial performance. Path length (mean±SEM) is expressed as a percentage of total swim time in the target annulus (A) and the outer annulus (B) averaged across the two probe trials and gender. *p<0.01 compared with wild-type mice. See Section 6 for details.

5. DETAILED DESCRIPTION OF THE INVENTION

The present invention is based on the surprising discovery, on the part of the inventors, that phosphodiesterase (PDE) activity, in particular, phosphodiesterase 1B (PDE1B) activity, functions in brain tissue as a regulator of locomotor activity and learning and memory. According to the invention, PDE1B may be used a therapeutic target for regulation of intracellular signaling pathways, preferably in the nervous system, including but not limited to a dopamine D1 receptor, dopamine D2 receptor, nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP) or endorphin intracellular signaling pathway. In preferred embodiments, PDE1B may be used as a therapeutic target for treatment of, e.g., a PDE1B-related disorder or a dopamine D1 receptor intracellular pathway disorder. In a specific embodiment, PDE1B may be used as a therapeutic target for treatment of Parkinson's disease.

Activation of dopamine (DA) per se and agents that enhance dopaminergic neurotransmission act on cell-surface receptors. Without wishing to be bound by any particular theory, in one aspect of the invention, dopamine D1 receptors mediate the phosphorylation of DARPP-32 via dopamine D1 receptor intracellular signaling pathways. According to the invention, dopamine D1 receptor activation leads to adenylyl cyclase activation (and increased cAMP). cAMP activates protein kinase A (PKA; cAMP-dependent protein kinase), which phosphorylates (or modulates phosphorylation of) downstream elements in intracellular signaling pathways, including but not limited to, DARPP-32 (dopamine and cAMP-regulated phosphoprotein-32); ARPP-16 (DARPP-16), ARPP-19 (DARPP-19), ARPP-21 (DARPP-21), cAMP responsive element binding protein (CREB), AMPA receptor (e.g., GluR1 AMPA receptor), cAMP, cGMP, CK1, CK2, Cdk5, PKA, PKG, PP-2C, PP-2B and PP-1. These intracellular signaling pathways are down-regulated or antagonized by phosphodiesterases (PDEs), including but not limited to PDE1B, which hydrolyzes cAMP to its 5'-monophosphate.

In another aspect of the invention, dopamine D2 receptor activation leads to adenylyl cyclase inhibition (and decreased cAMP). Intracellular concentration of cGMP also are unchanged or inhibited after D2 receptor activation. cGMP activates protein kinase G (PKG; cGMP-dependent protein kinase), which phosphorylates downstream signal transduction pathway elements, including but not limited to downstream elements in intracellular signaling pathways, including but not limited to, DARPP-32 (dopamine and cAMP-regulated phosphoprotein-32), ARPP-16 (DARPP-16), ARPP-19 (DARPP-19), ARPP-21 (DARPP-21), cAMP responsive element binding protein (CREB), AMPA receptor (e.g., GluR1 AMPA receptor), cAMP, cGMP, CK1, CK2, Cdk5, PKA, PKG, PP-2C, PP-2B and PP-1.

In another aspect of the invention, calcium-regulated PDE1B is an interface for regulating activity between dopamine-regulated intracellular signaling pathways and another intracellular signaling pathways, including but not limited to a nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP) or endorphin intracellular signaling pathway. In another aspect of the invention, PDE1B regulates signaling from other cAMP- or cGMP-coupled inputs (A2a, D2, opiate, nitric oxide, glutamate, etc.) that modulate of phosphorylation of DARPP-32. Furthermore, in certain aspects, PDE1B regulates DARPP-32-independent signaling from the D1 receptor, as well as other cAMP- or cGMP-coupled inputs (A2a, D2, opiate, nitric oxide, glutamate, etc.) by modulating the direct phosphorylation, by PKA and by PKG, of endpoint proteins including, but not limited to, the AMPA receptor, calcium channels, Na/K ATPase, NMDA receptor, and CREB. Hence, according to the invention, enhancement of cAMP signaling by inactivation of PDE1B-mediated cyclic nucleotide hydrolysis plays a significant role in dopaminergic function through regulating the activity of DARPP-32 and these related intracellular signaling pathways. Thus, according to the invention, modulation of PDE1B activity should also modulate the activity of these inter-related intracellular signaling pathways.

For clarity of disclosure, and not by way of limitation, the detailed description of the invention is divided into the subsections set forth below.

5.1. Methods for Modulating the Activity of PDE1B

The present invention provides a method for modulating PDE1B activity in a cell or tissue comprising contacting said cell or tissue with an amount of a compound sufficient to alter activity of an intracellular signaling pathway, including but not limited to the dopamine D1 receptor intracellular signaling, wherein contact of said cell or tissue with the compound results in modulation of PDE1B activity.

In certain embodiments, the compound modulates the activity of PDE1B by binding to PDE1B. Binding may be measured under any standard art-known physiological conditions, according to methods well known in the art.

In other embodiments, the phosphorylation of phospho-Thr34 of DARPP-32 or phospho-Ser845 of GluR1 AMPA receptor is modulated via modulation of PDE1 B.

In other embodiments, the phosphorylation of an element downstream in an intracellular signaling pathway, including but not limited to a calcium channel, Na/K ATPase, NMDA receptor, and CREB, is modulated via modulation of PDE1B.

The present invention also provides a method for modulating activity of an intracellular signaling molecule, including, but not limited to DARPP-32 (dopamine and cAMP-regulated phosphoprotein-32), ARPP-16 (DARPP-16), ARPP-19 (DARPP-19), ARPP-21 (DARPP-21), cAMP responsive element binding protein (CREB), AMPA receptor (e.g., GluR1 AMPA receptor), cAMP, cGMP, CK1, CK2, Cdk5, PKA, PKG, PP-2C, PP-2B, PP-1, calcium channels, Na/K ATPase and NMDA receptor, comprising administering (for example, to an individual, patient or animal) an amount of a compound sufficient to alter activity of an intracellular signaling pathway, including but not limited to a dopamine D1 receptor, dopamine D2 receptor, nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP) or endorphin intracellular signaling pathway. In certain embodiments, the compound is a compound identified by the methods of the invention, wherein the compound modulates PDE1B activity and wherein modulation of PDE1B activity results in an alteration in the activity of said intracellular signaling molecule in a cell or tissue. In a specific embodiment, the compound binds to PDE1B. In another specific embodiment, the compound alters expression of PDE1B. In certain embodiments, the intracellular signaling molecule is downstream in a dopamine D1 receptor intracellular signaling pathway.

In a specific embodiment, the intracellular signaling molecule is in an excitable cell, e.g., a neuron.

In specific embodiments of the invention, the activity of PDE1B is increased. In other specific embodiments, the activity of PDE1B is decreased. In certain embodiments, activity of PDE1B encompasses expression of PDE1B. Expression (e.g., gene expression, expression of a protein) may be measured by any method commonly known in the art.

In another embodiment, the invention provides a method for regulating phosphorylation-dependent activation of an intracellular signaling molecule, including but not limited to, DARPP-32 (dopamine and cAMP-regulated phosphoprotein-32), ARPP-16 (DARPP-16), ARPP-19 (DARPP-19), ARPP-21 (DARPP-21), cAMP responsive element binding protein (CREB), AMPA receptor (e.g., GluR1 AMPA receptor), cAMP, cGMP, CK1, CK2, Cdk5, PKA, PKG, PP-2C, PP-2B, PP-1, calcium channels, Na/K ATPase and NMDA receptor, in a cell or tissue comprising administering an amount of a compound sufficient to modulate PDE1B activity, wherein modulation of the PDE1B activity results in an alteration in the phosphorylation-dependent activation of said molecule in the cell or tissue.

According to the invention, a cell or tissue may include, but not be limited to: an excitable cell, e.g., a sensory neuron, motorneuron, or interneuron; a glial cell; a primary culture of cells, e.g., a primary culture of neuronal or glial cells; cell(s) derived from a neuronal or glial cell line; dissociated cell(s); whole cell(s) or intact cell(s); permeabilized cell(s); a broken cell preparation; an isolated and/or purified cell preparation; a cellular extract or purified enzyme preparation; a tissue or organ, e.g., brain, brain structure, brain slice, spinal cord, spinal cord slice, central nervous system, peripheral nervous system, or nerve; tissue slices, and a whole animal.

In certain embodiments, the brain structure is the striatum, basal ganglia, nucleus accumbens, or their anatomical and/or functional counterparts in other mammalian species.

In one embodiment, a method is provided for modulating PDE activity in cells or tissues of interest in vitro.

In another embodiment, PDE1B activity in cells or tissues of interest is modulated in situ or in vivo. The in vitro, in situ and in vivo applications may include, but are not limited to modulating activity in any of the cells or tissues disclosed hereinabove.

5.2. Methods for Screening for Compounds that Modulate the Activity of PDE1B The present invention provides, in vivo, in situ, and in vitro, methods of identifying an agent, drug or compound for modulating PDE1B activity in a cell or tissue. In one aspect, the method comprises identifying an agent to be tested for an ability to treat a disorder, including, but not limited to, a PDE1B-related disorder and a dopamine D1 intracellular signaling pathway disorder. Such methods can be used alone or in conjunction with each other.

In one embodiment, the invention provides a method of identifying a compound that modulates activity of a dopamine D1 receptor intracellular signaling pathway in a cell or tissue comprising:

(a) determining a first level of activity of PDE1B in said cell or tissue;

(b) contacting said cell or tissue with a test compound; and (c) determining a second level of activity of PDE1B in said cell or tissue, wherein a difference in said first level and said second level of PDE1B activity is indicative of the ability of said test compound to modulate activity of a dopamine D1 receptor intracellular signaling pathway.

In one aspect of the invention, a difference in PDE1B activity determined according to the methods of the invention is indicative of the ability of said test compound to modulate phosphorylation-dependent activation of an intracellular signaling pathway, including, but not limited to a dopamine D1 receptor, dopamine D2 receptor, nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP) or endorphin intracellular signaling pathway.

In another aspect of the invention, a difference in PDE1B activity is indicative of the ability of said test compound to modulate phosphorylation-dependent activation of an intracellular signaling molecule, including but not limited to DARPP-32 (dopamine and cAMP-regulated phosphoprotein-32), ARPP-16 (DARPP-16), ARPP-19 (DARPP-19), ARPP-21 (DARPP-21), cAMP responsive element binding protein (CREB), AMPA receptor (e.g., GluR1 AMPA receptor), cAMP, cGMP, CK1, CK2, Cdk5, PKA, PKG, PP-2C, PP-2B, PP-1, calcium channels, Na/K ATPase and NMDA receptor.

In another embodiment, the invention provides a method of identifying a compound that modulates PDE1B activity in a dopamine D1 receptor intracellular signaling pathway in a cell or tissue comprising:

(a) determining a first level of PDE1B activity in said cell or tissue;

(b) contacting said cell or tissue with a test compound; and (c) determining a second level of PDE1B activity in said cell or tissue, wherein a difference in said first level and said second level of PDE1B activity is indicative of the ability of said test compound to modulate PDE1B activity. In certain embodiments, the difference in PDE1B activity is indicative of the ability of said test compound to modulate activity of the dopamine D1 receptor intracellular signaling pathway. In another embodiment, the difference in PDE1B activity is indicative of the ability of the test compound to modulate phosphorylation-dependent activation of an intracellular signaling pathway molecule, including but not limited to DARPP-32 (dopamine and cAMP-regulated phosphoprotein-32), ARPP-16 (DARPP-16), ARPP-19 (DARPP-19), ARPP-21 (DARPP-21), cAMP responsive element binding protein (CREB), AMPA receptor (e.g., GluR1 AMPA receptor), cAMP, cGMP, CK1, CK2, Cdk5, PKA, PKG, PP-2C, PP-2B, PP-1, calcium channels, Na/K ATPase and NMDA receptor.

According to the invention, a control level means a separate baseline level measured in a comparable cell or tissue not contacted with a test compound or a level that is measured in a cell or tissue prior to contacting it with a test compound.

The invention also provides a method of identifying a compound that modulates activity of a dopamine D1 receptor intracellular signaling pathway molecule in a cell or tissue comprising:
  (a) contacting said cell or tissue with a test compound; and
  (b) determining a level of activity of PDE1B in said cell or tissue;
wherein a difference in said level and a control level of PDE1B activity in a comparable cell or tissue not contacted with the test compound is indicative of the ability of said test compound to modulate activity of a dopamine D1 receptor intracellular signaling pathway molecule. In certain embodiments, modulation of PDE1B activity regulates modulation of a dopamine D1 receptor intracellular signaling pathway. In other embodiments, the difference in activity is PDE1B activity is indicative of the ability of said test compound to modulate phosphorylation-dependent activation of an intracellular signaling molecule, including but not limited to DARPP-32 (dopamine and cAMP-regulated phosphoprotein-32), ARPP-16 (DARPP-16), ARPP-19 (DARPP-19), ARPP-21 (DARPP-21), cAMP responsive element binding protein (CREB), AMPA receptor (e.g., GluR1 AMPA receptor), cAMP, cGMP, CK1, CK2, Cdk5, PKA, PKG, PP-2C, PP-2B, PP-1, calcium channels, Na/K ATPase and NMDA receptor.

In another embodiment, the invention provides a method of identifying a compound that modulates PDE1B activity in a dopamine D1 receptor intracellular signaling pathway in a cell or tissue comprising:
  (a) contacting said cell or tissue with a test compound; and
  (b) determining a level of PDE1B activity in said cell or tissue;
wherein a difference in said level and a control level of PDE1B activity in a comparable cell or tissue not contacted with the test compound is indicative of the ability of said test compound to modulate PDE1B activity. In certain embodiments, modulation of PDE1B activity regulates modulation of a dopamine D1 receptor intracellular signaling pathway. In certain embodiments, the difference in activity is PDE1B activity is indicative of the ability of said test compound to modulate phosphorylation-dependent activation of an intracellular signaling molecule, including but not limited to DARPP-32 (dopamine and cAMP-regulated phosphoprotein-32), ARPP-16 (DARPP-16), ARPP-19 (DARPP-19), ARPP-21 (DARPP-21), cAMP responsive element binding protein (CREB), AMPA receptor (e.g., GluR1 AMPA receptor), cAMP, cGMP, CK1, CK2, Cdk5, PKA, PKG, PP-2C, PP-2B, PP-1, calcium channels, Na/K ATPase and NMDA receptor.

The invention also provides a method for identifying an agent to be tested for an ability to treat a disorder, including but not limited to, a PDE1B-related disorder and a dopamine D1 intracellular signaling pathway disorder, in a patient in need of such treatment comprising:
  (a) contacting a potential agent with PDE1B and Thr34-dephosphorylated DARPP-32; and
  (b) detecting the amount of phosphorylation of Thr34-dephosphorylated DARPP-32,
wherein the agent is identified if an increase in the phosphorylation of Thr34-dephosphorylated DARPP-32 is detected in the presence of the potential agent. In certain embodiments, the PDE1B and Thr34-dephosphorylated DARPP-32 are in a cell or tissue. In other embodiments, the ability to treat a dopamine D1 receptor intracellular signaling pathway disorder is tested.

The invention also provides a method for identifying an agent to be tested for an ability to treat a disorder, including but not limited to a PDE1B-related disorder and a dopamine D1 intracellular signaling pathway disorder, in a patient in need or such treatment comprising:
  (a) contacting a potential agent with PDE1B and Ser845-dephosphorylated GluR1 AMPA receptor; and
  (b) detecting the amount of phosphorylation of Ser845-dephosphorylated GluR1 AMPA receptor; wherein the agent is identified if an increase in the phosphorylation of Ser845-dephosphorylated GluR1 AMPA receptor is detected in the presence of the potential agent.
In certain embodiments, the PDE1B and Ser845-dephosphorylated GluR1 AMPA receptor are in a cell or tissue. In other embodiments, the ability to treat a dopamine D1 receptor intracellular signaling pathway disorder is tested.

In another embodiment, the invention provides a method for identifying an agent to be tested for an ability to modulate activity of a dopamine D1 receptor, dopamine D2 receptor, nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP) or endorphin intracellular signaling pathway in a cell or tissue comprising:
  (a) determining a first level of PDE1B activity in said cell or tissue;
  (b) contacting said cell or tissue with a potential agent; and
  (c) determining a second level of PDE1B activity in said cell or tissue,
wherein a difference in said first level and said second level of PDE1B activity is indicative of the ability of said potential agent to modulate activity of the intracellular signaling pathway. In certain embodiments, the method comprises the additional step of:
  (d) determining whether said intracellular signaling pathway is modulated.
In a specific embodiment, the intracellular signaling pathway is a dopamine D1 receptor intracellular signaling pathway.

In another embodiment, the invention provides a method for identifying an agent to be tested for an ability to modulate activity of a dopamine D1 receptor, dopamine D2 receptor, nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP) or endorphin intracellular signaling pathway in a cell or tissue comprising:
  (a) contacting said cell or tissue with a potential agent; and
  (b) determining a level of PDE1B activity in said cell or tissue;
wherein a difference in said level and a control level of PDE1B activity in a comparable cell or tissue not contacted with the test compound is indicative of the ability of said test compound to modulate of the intracellular signaling pathway. In certain embodiments, modulation of a dopamine D1 receptor intracellular signaling pathway is modulated by PDE1B. In certain embodiments, the method comprises the additional step of:
  (c) determining whether said intracellular signaling pathway is modulated.
In a specific embodiment, the intracellular signaling pathway is a dopamine D1 intracellular signaling pathway.

As would be clearly understood by a person of ordinary skill in the art, any and/or all of the embodiments disclosed herein for identifying an agent, drug or compound that can modulate the activity of PDE1B, including such procedures that incorporate rational drug design, as disclosed herein, can be combined to form additional drug screens and assays, all of which are contemplated by the present invention.

Since PDE1B plays an important role in controlling levels of cAMP, and since the cAMP-PKA pathway interacts with many other signaling pathways in the brain, modulation of PDE1B will, in certain embodiments, ameliorate the symptoms and/or be used in the treatment of disorders including, but not limited to, Parkinson's disease, Huntington's disease, attention deficit disorder (ADD), attention deficit hyperactivity disorder (ADHD), neurodegenerative disorder, Tourette's syndrome, tic disorder, Lesch-Nyans disease, pain, dystonias, substance or drug abuse, schizophrenia, schizoaffective disorder, depression, affective disorder, manic-depressive disorder, obsessive-compulsive disorder, eating disorder, emesis, panic disorder, anxiety disorder, migraine, myoclonus, premenstrual syndrome (PMS), post-traumatic stress syndrome, carcinoid syndrome, Alzheimer's disease, stroke, epilepsy, sleep or circadian rhythm disorder (e.g., insomnia), sexual disorder, stress disorder, hypertension and cancer.

According to the methods of the invention, patterns and/or levels of DARPP-32 phosphorylation and/or GluR1 AMPA receptor phosphorylation may be determined both before and after treatment of cells or tissues with a test compound.

One of skill would understand that according to the invention, once a compound is identified as capable of producing, e.g., altered patterns and/or levels of DARPP-32 phosphorylation and/or GluR1 AMPA receptor phosphorylation similar to known ameliorative compounds, the compound may be used to treat, a PDE1B-related disorder, a dopamine D1 receptor intracellular signaling pathway disorder, as well as other conditions in which dopaminergic systems are involved. Such conditions would include, but not be limited to, a PDE1B-related disorder and a dopamine D1 intracellular signaling pathway disorder. In the context of the present invention, the compounds identified would be administered as an effective dose or amount which can be determined by one of skill in the art based on data from studies such as presented in this specification. Such data would include, but not be limited to, results from IC50 determinations.

The present invention also provides in vivo methods of identifying agents that can modulate the activity of a dopamine D1 receptor, dopamine D2 receptor, nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP) or endorphin intracellular signaling pathway via modulation of PDE1B activity. Such methods can be employed alone or in conjunction with in vitro and in situ methods as disclosed herein.

One such in vivo method comprises administering the agent to a non-human mammal. The amount (and/or rate) of activation of PDE1B is then determined. An agent is identified as capable of modulating the activity of an intracellular signaling pathway, including but not limited to a dopamine D1 receptor, dopamine D2 receptor, nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP) or endorphin intracellular signaling pathway, via modulation of PDE1B, when the amount (and/or rate) of PDE1B activation is increased or decreased in the presence of the agent relative to in the absence of the agent. In preferred embodiments, the non-human mammal is a rodent. In a more preferred embodiment, the rodent is a wild-type mouse. In other embodiments, the non-human mammal is an animal model for a disease or disorder. Such animal models are disclosed herein.

In another embodiment, an experimental animal is used to ascertain the effect of a potential agent on a disorder, including but not limited to a PDE1B-related disorder and a dopamine D1 receptor intracellular signaling pathway disorder. A potential modulator that ameliorates the disorder can then be selected.

For example, in certain embodiments, a locomotor or learning behavioral response of an animal can be determined in the presence and absence of the agent. In specific embodiment, locomotor activity of the animal, e.g., a mouse, can be measured in an activity monitor as disclosed in Section 6. In a specific embodiment, a behavioral test, e.g., a test for exploratory behavior during horizontal locomotor activity, a test for locomotor activity after administration of methamphetamine treatment, or a Morris water maze can be used, as disclosed in Section 6.

Methods of testing a potential therapeutic agent (e.g., a candidate drug, potential modulator, etc.) in animals or animal models are well known in the art. Thus potential therapeutic agents can be used to treat whole animals. The potential modulators can be administered by a variety of ways including topically, orally, subcutaneously, or intraperitoneally (such as by intraperitoneal injection) depending on the proposed use. Optimal dose will be empirically defined. Animals can be sacrificed by focused microwave beam irradiation, for example.

The potential efficacy of these compounds in relieving pathological symptoms of a disorder, including but not limited to, a PDE1B-related disorder and a dopamine D1 intracellular signaling pathway disorder, can be assessed in animal models for disease. For example, animals ectopically expressing the human disease-causing form of the Huntington's disease (HD) gene exhibit neuropathological symptoms similar to those of HD patients. Models such as these can be used to assess the efficacy of any potential therapeutic agents as disclosed hereinbelow. Generally, at least two groups of animals are used in the assay, with at least one group being a control group in which the administration vehicle is administered without the potential modulator.

In one embodiment, the invention provides a method for selecting a potential therapeutic agent for use in the treatment of a PDE1B-related or dopamine D1 receptor intracellular signaling pathway disorder, comprising:
  (a) administering a potential therapeutic agent to an animal;
  (b) measuring the response of said animal to said potential therapeutic agent;
  (c) comparing the response of said animal with that of a control animal to which the potential therapeutic agent has not been administered; and
  (d) selecting a potential therapeutic agent based on the difference in responses observed between said animal and said control animal.

In a preferred embodiment, the animal is a mouse.

In another embodiment, the invention provides a method for selecting a potential therapeutic agent for use in the treatment of a PDE1B-related or dopamine D1 receptor intracellular signaling pathway disorder, comprising:
  (a) administering a potential therapeutic agent to an animal;

(b) measuring the response of said animal to administration of a neurotransmitter that interacts with an intracellular signaling pathway;

(c) comparing the response of said animal with that of a control animal to which the potential therapeutic agent has not been administered; and (d) selecting a potential therapeutic agent based on the difference in responses observed between said animal and said control animal.

In a preferred embodiment, the animal is a mouse. In another embodiment, the intracellular signaling pathway is a dopamine D1 receptor, dopamine D2 receptor, nitric oxide, noradrenergic, neurotensin, CCK, VIP, serotonin, glutamate, GABA, acetylcholine, adenosine, cannabinoid receptor, natriuretic peptide or endorphin intracellular signaling pathway.

In another embodiment, the invention provides a method for selecting a potential therapeutic agent for use in the treatment of a PDE1B-related or dopamine D1 receptor intracellular signaling pathway disorder, comprising:

(a) administering a potential therapeutic agent to an animal;

(b) measuring the response of said animal to dopamine administration;

(c) comparing the response to dopamine administration of said animal with that of a control animal to which the potential therapeutic agent has not been administered; and (d) selecting a potential therapeutic agent based on the difference in responses observed between said animal and said control animal.

In a preferred embodiment, the animal is a mouse.

In another embodiment, the invention provides a method for selecting a potential therapeutic agent for use in the treatment of a PDE1B-related or dopamine D1 receptor intracellular signaling pathway disorder, comprising:

(a) administering a potential therapeutic agent to an animal;

(b) measuring the response of said animal, wherein the response is selected from the group consisting of:
(i) exhibition of exploratory behavior during a test period for horizontal locomotor activity;
(ii) exhibition of hyperactivity after administration of methamphetamine treatment;
(iii) path length in acquisition of a Morris water maze;
(iv) change in level of phospho-Thr34 or phospho-Ser845 in striatal slices from said animal; and
(v) change in level of phospho-Thr34 or phospho-Ser845 in nucleus accumbens slices from said animal, (c) comparing the response of said animal with that of a control animal to which the potential therapeutic agent has not been administered; and (d) selecting a potential therapeutic agent based on the difference in responses observed between said animal and said control animal.

In a preferred embodiment, the animal is a mouse.

Another aspect of the invention is a method for selecting a therapeutic agent for potential use in the treatment of disorder, including but not limited to a PDE1B-related disorder and a dopamine D1 receptor intracellular signaling pathway disorder, which comprises administering a suspected therapeutic agent to an animal model, and measuring and/or determining the putative therapeutic agent's effect on any of the phenotypic characteristics of the animal model, which may be believed to be related to said disorder. Potential therapeutic agents are selected on the basis of whether there is a statistical significance between a test response and a normal (i.e., naive or wild-type) response. Potential therapeutic agents are selected that show a statistically significant change in the characteristic measured/determined. In a preferred embodiment, the response of a wild-type animal in the presence of a therapeutic agent is characteristically different from the response of a wild-type animal to which the agent has not been administered.

A still further aspect of the invention is a method for selecting a therapeutic agent for possible use in the treatment of a disorder, including but not limited to a PDE1B-related disorder and a dopamine D1 receptor intracellular signaling pathway disorder, which comprises administering a suspected therapeutic agent to an animal model for a disorder and measuring and/or determining the putative therapeutic agent's effect on any of the phenotypic characteristics outlined above which may be believed to be related to said disorder.

In other embodiments, the agent is administered along with a D1 receptor agonist. The amount (and/or rate) of modulation of PDE1B activity is then determined. Since the administration of e.g., a D1 receptor agonist, in the absence of the agent, should result in an increase in PDE1B, DARPP-32 and GluR1 AMPA receptor activity, an agent is identified as capable of modulating the activity of PDE1B when the amount (and/or rate) of activation is significantly increased or decreased in the presence of the agent relative to in the absence of the agent.

In other embodiments, the agent is administered along with a D1 receptor antagonist. The amount (and/or rate) of modulation of PDE1B activity is then determined. Since the administration of a D1 receptor antagonist in the absence of the agent should result in a decrease in PDE1B, DARPP-32 and GluR1 AMPA receptor activity, an agent is identified as capable of modulating the activity of PDE1B when the amount (and/or rate) of activation is significantly increased or decreased in the presence of the agent relative to in the absence of the agent.

In certain embodiments, combinatorial libraries of chemical compounds, based on different structural skeletons (e.g., purines), as well as unrelated naturally occurring compounds, can be tested as drug candidates. In a preferred embodiment of this type, the assay is performed using high throughput technology with automated robotic technology as disclosed herein. Positive results ("hits") represent either the reduced or increased activity of PDE1B, as compared to the control reactions (in which the drug candidate is not included in the assay).

Once a drug candidate is selected, structural variants of the drug candidate can be tested. These compounds can also be scrutinized and modified with parameters such as membrane permeability, specificity of effects, and toxicity. The selected (e.g., the most potent) compounds of this secondary screening can then be evaluated in situ and in animal models (see Section 5.5) to determine whether the selected compounds alter the activity of PDE1B, and/or induce predicted behavioral alterations with minimal to no side-effects. Such behavioral abnormalities may include, but not be limited to, testing locomotor activity or learning and memory, as disclosed herein (see also, e.g., Kosten et al., J. Pharmacol., Exp. Ther. 269: 137-144 (1994); U.S. patent application Ser. Nos. 09/419, 379, by Bibb et al., entitled "Methods of Identifying Agents That Regulate Phosphorylation/Dephosphorylation in Dopamine Signaling," filed Oct. 15, 1999, and 09/687,959, by Bibb et al., entitled "Methods of Identifying Agents That Regulate Phosphorylation/Dephosphorylation in Dopamine Signaling," filed Oct. 13, 2000, each of which is incorporated herein by reference in its entirety); and/or self-administration of selected drugs or in prepulse inhibition (see, e.g., U.S. Pat.

No. 5,777,195 Issued Jul. 7, 1998, incorporated herein by reference in its entirety). In specific embodiments, methods for testing for antidepressant efficacy commonly known in the art, e.g., a rodent tail-suspension test, can be used.

These tests can be then be followed by human trials in clinical studies. Alternatively, in certain embodiments, human trials in clinical studies can be performed without animal testing. Compounds affecting targets other than PDE1B can also be similarly screened, using alternative targets exemplified below.

Alternatively, modulators (e.g., activators or inhibitors) of PDE1B activity can be obtained by screening, e.g., a random peptide library produced by recombinant bacteriophage (see, e.g., Scott and Smith, Science 249:386-390 (1990); Cwirla et al., Proc. Natl. Acad. Sci. USA 87:6378-6382 (1990); Devlin et al., Science 249:404-406 (1990)) or a chemical library. Using the "phage method" very large libraries can be constructed (106-108 chemical entities). A second approach may be to use chemical methods, of which the Geysen method (Geysen et al., Molecular Immunology 23:709-715 (1986); Geysen et al. J. Immunologic Method 102:259-274 (1987)) and the method of Fodor et al. (Science 251:767-773 (1991)) are examples. Furka et al. (14th international Congress of Biochemistry, Volume 5, Abstract FR:013 (1988); Furka, Int. J. Peptide Protein Res. 37:487-493 (1991)), Houghton (U.S. Pat. No. 4,631,211, issued December 1986) and Rutter et al. (U.S. Pat. No. 5,010,175, issued Apr. 23, 1991) disclose methods to produce a mixture of peptides. Such peptides can be tested as potential modulators of PDE1B activity.

In another aspect, synthetic libraries (Needels et al., Proc. Natl. Acad. Sci. USA 90:10700-4 (1993); Ohlmeyer et al., Proc. Natl. Acad. Sci. USA 90:10922-10926 (1993); Lam et al., International Patent Publication No. WO 92/00252; Kocis et al., International Patent Publication No. WO 94/28028, each of which is incorporated herein by reference in its entirety), and the like can be used to screen for modulators of PDE1B activation, according to the present invention. Once a potential modulator is identified, chemical analogues can be either selected from a library of chemicals as are commercially available (e.g., from Chembridge Corporation, San Diego, Calif. or Evotec OAI, Abingdon, UK), or alternatively synthesized de novo. The prospective agent (drug) can be placed into any standard assay to test its effect on the activity of PDE1B activation. A drug is then selected that modulates the activity of PDE1B activation.

The present invention also contemplates screens for small molecules, analogs thereof, as well as screens for natural modulators of PDE1B, such as those molecules that bind to and inhibit or activate, e.g., D1 receptors or PDE1B in vivo. Alternatively, natural products libraries can be screened using assays of the invention for molecules that modulate e.g., D1 receptors or PDE1B activity.

In one particular assay, the target e.g., PDE1B, can be attached to a solid support. Methods for placing such targets on the solid support are well known in the art and include such things as linking biotin to the target and linking avidin to the solid support. The solid support can be washed to remove unreacted species. A solution of a labeled potential modulator (e.g., an inhibitor) can be contacted with the solid support. The solid support is washed again to remove the potential modulator not bound to the support. The amount of labeled potential modulator remaining with the solid support and thereby bound to the target can be determined. Alternatively, or in addition, the dissociation constant between the labeled potential modulator and the target, for example, can be determined. Suitable labels for either the target or the potential modulator are disclosed herein.

In another aspect of the present invention, a potential modulator can be assayed for its ability to modulate the phosphorylation of Thr34 DARPP-32 by PKA or its dephosphorylation by PP2B, or the phosphorylation of Ser845-GluR1 AMPA receptor by PKA, or the dephosphorylation of Ser845-GluR1 AMPA receptor, either independently, or subsequent to, a binding assay as disclosed herein. In one such embodiment, the amount and/or rate of phosphorylation or dephosphorylation of Thr34 DARPP-32, or a fragment thereof comprising the Thr34 residue, is determined. In another embodiment, the amount and/or rate of phosphorylation or dephosphorylation of Ser845 GluR1 AMPA receptor, or a fragment thereof comprising the Ser845 residue, is determined. Such assays are known in the art. In certain embodiments, the methods disclosed in U.S. patent application Ser. Nos. 09/419,379, by Bibb et al., entitled "Methods of Identifying Agents That Regulate Phosphorylation/Dephosphorylation in Dopamine Signaling," filed Oct. 15, 1999, and 09/687,959, by Bibb et al., entitled "Methods of Identifying Agents That Regulate Phosphorylation/Dephosphorylation in Dopamine Signaling," filed Oct. 13, 2000 (each of which is incorporated herein by reference in its entirety) or by Yan et al. (1999, Nature Neurosci. 3:13-17) are used. In another embodiment, the methods of Yan et al. (1999, Nature Neurosci. 3:13-17) can be used to assay for AMPA receptor activity. Thus, according to the methods of the invention, a modulator of PDE1B activity that modulates the activity of an intracellular signaling molecule is then selected In another embodiment, a potential modulator can be added to a striatal tissue slice (as disclosed in Sections 6). Tissue samples can be treated with various concentrations of a potential modulator and the sample can then be analyzed for activity of PDE1B. Potential modulators of the activity of PDE1B can be tested for example, on intact neurons in situ by treatment of acutely prepared neostriatal slices incubated in Krebs bicarbonate buffer solution containing the reagent. The effects of these compounds can be tested by empirically defining the optimal concentration and time of incubation. In a specific embodiment, homogenates of striatal tissue are subjected to immunoblot analysis 5.2.1. Enzymatic Assays for Phosphodiesterases According to the methods of the invention, inhibitors and activators of calmodulin-dependent phosphodiesterases (CaM-PDEs), including, but not limited to PDE1B, can be detected and isolated using methods commonly known in the art, and/or identified by direct assay of isolated enzyme. Such assays are well known to those of skill in the art.

For example, in one embodiment, the methods of Thompson et al. (1971, Multiple cyclic nucleotide phosphodiesterase activities from rat brain. Biochemistry 10: 311-316) may be used to assay for PDE activity. In one aspect, either cAMP or cGMP may be used as a substrate in the assay. In certain embodiments, tissue is first homogenized in a buffer that contains a mixture of protease inhibitors, e.g., as described by Swinnen et al., (1989, Proc Natl Acad Sci USA, 86: 8197-8201).

PDE1B may be immunoprecipitated from brain homogenate using standard methods, using, e.g., a commercial antibody, e.g., AB-1655 Rabbit Anti-Calmodulin-Dependent Phosphodiesterase 1B 1 Affinity-Purified Antibody (Chemicon).

In another embodiment, PDE1B can be isolated from bovine brain using ion-exchange chromatography and affinity chromatography on Calmodulin-Sepharose (Sharma, R. K., T. H. Wang, et al. (1980). "Purification and properties of bovine brain calmodulin-dependent cyclic nucleotide phosphodiesterase." J Biol Chem 255(12): 5916-23).

In another embodiment, a cloned cDNA copy of a CaM-PDE mRNA can be used to express epitope-tagged enzyme in baculovirus and this enzyme can be affinity purified from insect cell extracts. Sonnenburg et al. described this procedure for PDE1A enzyme (Sonnenburg, W. K., D. Seger, et al. (1995). "Identification of inhibitory and calmodulin-binding domains of the PDE1A1 and PDE1A2 calmodulin-stimulated cyclic nucleotide phosphodiesterases." J Biol Chem 270(52): 30989-1000) and it may be readily adapted for PDE1B.

Mammalian phosphodiesterases may also be expressed in PDE-deficient yeast (Engels, P., M. Sullivan, et al. (1995). "Molecular cloning and functional expression in yeast of a human cAMP-specific phosphodiesterase subtype (PDE IV-C)." FEBS Lett 358(3): 305-10; Atienza, J. M. and J. Colicelli (1998). "Yeast model system for study of mammalian phosphodiesterases." Methods 14(1): 35-42). CaM-PDE expression in recombinant yeast may also be carried out according to the methods described by Loughrey et al. (1996, "Isolation and characterization of cDNAs corresponding to two human calcium, calmodulin-regulated, 3',5'-cyclic nucleotide phosphodiesterases." J Biol Chem 271(2): 796-806).

Overexpression of a CaM-PDE may be carried out according to methods commonly known in the art. In one embodiment, overexpression of a CaM-PDE is carried out in transfected mammalian cells using vectors such as pcDNA3. In one aspect of this embodiment, the overexpression of the CaM-PDE provides a means to study inhibition of the cloned enzyme, by comparing transfected and non-transfected cells (Yan, C., A. Z. Zhao, et al. (1996). "The calmodulin-dependent phosphodiesterase gene PDE1C encodes several functionally different splice variants in a tissue-specific manner." J Biol Chem 271(41): 25699-706).

CaM-PDE activity may be assayed according to methods commonly known in the art. Phosphodiesterase cleavage of radioactively labeled cAMP or cGMP can be used to detect phosphodiesterase inhibitors. In one embodiment, the assay for phosphodiesterase activity relies on recovery of labeled adenosine following a two-step biochemical assay. In the first step, phosphodiesterase hydrolyzes [$^3$H]cyclic AMP to [$^3$H]5'-AMP. In the second step, snake venom 5'-nucleotidase is added to convert the [$^3$H]5'-AMP to [$^3$H]adenosine. Labeled adenosine is separated from [$^3$H]cyclic AMP by anion exchange or affinity chromatography and then detected by liquid scintillation counting. One such assay has been described for cAMP-specific phosphodiesterase PDE4 by Hansen and Beavo (1982, "Purification of two calcium/calmodulin-dependent forms of cyclic nucleotide phosphodiesterase by using conformation-specific monoclonal antibody chromatography." Proc Natl Acad Sci USA 79(9): 2788-92), and modified for high throughput by Daniels and Alvarez (1996, "A semiautomated method for the assay of cyclic adenosine 5'-monophosphate phosphodiesterase." Anal Biochem 236(2): 367-9).

These assays may be modified, according to methods known in the art, to detect inhibitors of the calcium/calmodulin-dependent PDE1B enzyme. For example, in one embodiment, $CaCl_2$ (0.2 mM) and calmodulin (4 µg/ml) are added to the assay. PDE1B activity in semipurified mixtures can be detected by comparing phosphodiesterase activity in the presence of calcium and calmodulin with the activity measured in the presence of 1 mM EGTA.

In another embodiment, a high throughput method may be used to perform a CaM-PDE assay, for example, using the methods of Daniels and Alvarez (1996, "A semiautomated method for the assay of cyclic adenosine 5'-monophosphate phosphodiesterase." Anal Biochem 236(2): 367-9). Such an assay may also be modified, in certain embodiments, into a one-step procedure. In the one-step procedure, conversion of $^3$H-AMP to adenosine using snake venom phosphodiesterase is omitted. Instead, $^3$H-AMP is separated from [$^3$H]cyclic AMP by affinity chromatography using alumina or boronate resin at alkaline pH (Smith, B. J., M. R. Wales, et al. (1993). "A phosphodiesterase assay using alumina microcolumns." Anal Biochem 214(1): 355-7; Duplantier, A. J., C. J. Andresen, et al. (1998). "7-Oxo-4,5,6,7-tetrahydro-1H-pyrazolo[3,4-c]pyridines as novel inhibitors of human eosinophil phosphodiesterase." J Med Chem 41(13): 2268-77; Burnout, C., E. Auclair, et al. (2000). "Synthesis, structure-activity relationships, and pharmacological profile of 9-amino-4-oxo-1-phenyl-3,4,6,7-tetrahydro[1,4]diazepino[6, 7,1-hi]indoles: discovery of potent, selective phosphodiesterase type 4 inhibitors." J Med Chem 43(25): 4850-67).

5.2.2. Enzymatic Assays for Kinases and Phosphatases

Kinase activities can be monitored by a variety of methods known to those skilled in the art, e.g., the methods disclosed in Parker, Law, et al., 2000, Development of high throughput screening assays using fluorescence polarization: nuclear receptor-ligand-binding and kinase/phosphatase assays, J. Biomolec. Screening 5(2): 77-88; Bader et al. (2001, Journal of Biomolecular Screening 6(4): 255-64); Liu, F., X. H. Ma, et al. (2001). "Regulation of cyclin-dependent kinase 5 and casein kinase 1 by metabotropic glutamate receptors." Proceedings of the National Academy of Sciences of the United States of America 98(20): 11062-8; Evans, D. B., K. B. Rank, et al. (2002). "A scintillation proximity assay for studying inhibitors of human tau protein kinase II/Cdk5 using a 96-well format." Journal of Biochemical & Biophysical Methods 50(2-3): 151-61.

Using such methods, samples containing the kinase of interest are exposed under the appropriate conditions to radioactive ATP and a synthetic peptide substrate of the appropriate composition to provide a site for phosphorylation. The radioactive phosphate newly associated with the peptide is then measured. Addition of a chemical moiety, such as biotin covalently linked to the substrate peptide, allows binding of the substrate peptide by a streptavidin-coated bead. Bead-bound peptide can be isolated and associated radioactivity measured, or, preferably, radioactivity associated with the substrate peptide can be measured directly using a bead suitable for scintillation proximity assays.

Activities of protein phosphatases can be monitored by a variety of methods known to those skilled in the art, e.g., the methods disclosed in Cohen et al. (1988, Protein phosphatase-1 and protein phosphatase-2A from rabbit skeletal muscle, Methods Enzymol 159:390-408) or Stewart and Cohen (1988, Protein phosphatase-2B from rabbit skeletal muscle: a $Ca^{2+}$-dependent, calmodulin-stimulated enzyme, Methods Enzymol 159:409-16).

Modulators of PDE1B can also be identified by screening for modulators of DARPP-32 phosphorylation, i.e., Ser137 DARPP-32 phosphorylation (CK1), Thr75 DARPP-32 phosphorylation (Cdk5) or Thr34 DARPP-32 phosphorylation (PKA, PP2B, PP1). Such methods are disclosed in U.S. patent application Ser. Nos. 09/419,379, by Bibb et al., entitled "Methods of Identifying Agents That Regulate Phosphorylation/Dephosphorylation in Dopamine Signaling," filed Oct. 15, 1999, and 09/687,959, by Bibb et al., entitled "Methods of Identifying Agents That Regulate Phosphorylation/Dephosphorylation in Dopamine Signaling," filed Oct. 13, 2000; and in U.S. Pat. No. 5,777,195, by Fienberg et al., issued Jul. 7, 1998, each of which is incorporated herein by reference in its entirety.

5.2.3. Other Phosphorylation Assays

Phosphorylation of a peptide substrate can also be detected via direct binding of phosphospecific antibodies or by measuring displacement of a phosphospecific antibody from a competitor phosphopeptide (see, e.g., Parker, Law et al., 2000, Development of high throughput screening assays using fluorescence polarization: nuclear receptor-ligand-binding and kinase/phosphatase assays, J. Biomolec. Screening 5(2): 77-88). Fluorescence methods such as fluorescence resonance energy transfer (FRET) or fluorescence polarization (FP) can be used to detect the specific phosphopeptide-antibody complexes. These methods have the advantage that they employ "homogeneous" detection that is not dependent on isolation of the bound species, but rather depends on changes in fluorescence that occur owing to specific binding in solution.

Methods of producing phosphospecific antibodies are well known in the art. In one embodiment, the methods disclosed in U.S. patent application Ser. Nos. 09/419,379, by Bibb et al., entitled "Methods of Identifying Agents That Regulate Phosphorylation/Dephosphorylation in Dopamine Signaling," filed Oct. 15, 1999, and 09/687,959, by Bibb et al., entitled "Methods of Identifying Agents That Regulate Phosphorylation/Dephosphorylation in Dopamine Signaling," filed Oct. 13, 2000, (each of which is incorporated herein by reference in its entirety) are used to produce phosphorylation state-specific antibodies having specificity for, e.g., Thr34-phosphorylated DARPP-32.

Phosphorylation state-specific antibodies against phosphoserine, phosphothreonine, or phosphotyrosine are commercially available. These antibodies are useful for determining whether proteins are phosphorylated in general, and on which residue. Such antibodies are available from commercial sources (see, e.g., Smith, The Scientist 15[4]:24, Feb. 19, 2001 for list of commercial sources, including Santa Cruz Biotechnology Inc., Sigma RBI, Stratagene, Upstate Biotechnology and Zymed).

Fluorescence resonance energy transfer, or FRET, is widely used for homogeneous assays capable of detecting specific binding of macromolecules. FRET depends on the ability of excited "donor" fluorescent molecules (fluorophores) to transfer their energy to nearby "acceptor" fluorophores rather than emitting light. Thus, when the two fluorophores are brought together in space by binding to a substrate target, fluorescence emitted at the normal donor wavelength is reduced and fluorescence emitted by the acceptor fluorophore increases. Either the decrease in donor fluorescence or the increase in acceptor fluorescence can be used to measure the binding event.

In one embodiment, the methods disclosed in Bader et al. (2001, A cGMP-dependent protein kinase assay for high throughput screening based on time-resolved fluorescence resonance energy transfer, Journal of Biomolecular Screening 6(4): 255-64) are used to determine activity of e.g., a phosphodiesterase, kinase or protein phosphatase. Bader et al. discloses a cGMP-dependent protein kinase assay for high throughput screening based on time-resolved fluorescence resonance energy transfer ("FRET"), which as, would be appreciated by one of skill in the art, may be adapted for assays of a phosphodiesterase or protein phosphatase. Samples containing the kinase of interest are exposed to ATP and a synthetic peptide substrate with a kinase-specific phosphorylation site and an amino-terminal biotin moiety. Phosphorylated peptide is detected using allophycocyanin-labeled streptavidin, a phosphopeptide specific antibody, and a Europium-chelate-labeled secondary antibody. Simultaneous binding of the streptavidin and the phosphospecific antibody to a phosphorylated substrate molecule brings the Europium chelate "donor" on the secondary antibody close enough to the allophycocyanin fluorophore "acceptor" for fluorescence resonance energy transfer to occur, measurable as a decrease in Europium emission at 615 nm and an increase in allophycocyanin emission at 665 nm wavelength. The Europium—allophycocyanin donor—acceptor pair is commonly used in order to take advantage of the long fluorescence lifetime of excited Europium, thus the signal is "time-resolved".

Other pairs of fluorophores, such as coumarin and fluorescein isothiocyanate, can be used. Pairs of such molecules that can engage in fluorescence resonance energy transfer (FRET) are termed FRET pairs. In order for energy transfer to occur, the donor and acceptor molecules must typically be in close proximity (up to 70 to 100 Å (Clegg, 1992, Methods Enzymol. 211:353-388; Selvin, 1995, Methods Enzymol. 246: 300-334). The efficiency of energy transfer falls off rapidly with the distance between the donor and acceptor molecules. Molecules that are commonly used in FRET include fluorescein, 5-carboxyfluorescein (FAM), 2'7'-dimethoxy-4'5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), and 5-(2'-aminoethyl)aminonaphthalene-1-sulfonic acid (EDANS). Whether a fluorophore is a donor or an acceptor is defined by its excitation and emission spectra, and the fluorophore with which it is paired. For example, FAM is most efficiently excited by light with a wavelength of 488 nm, and emits light with a spectrum of 500 to 650 nm, and an emission maximum of 525 nm. FAM is a suitable donor fluorophore for use with JOE, TAMRA, and ROX (all of which have their excitation maximum at 514 nm).

Fluorescence polarization measurements can also be used for measuring the activity of a phosphodiesterase, protein kinase or a phosphatase (see, e.g., Parker, Law et al., 2000, Development of high throughput screening assays using fluorescence polarization: nuclear receptor-ligand-binding and kinase/phosphatase assays, J. Biomolec. Screening 5(2): 77-88; Turek et al., 2001, Anal. Biochem. 299: 45-53). Binding of a large specific antibody to a fluorescent small phosphopeptide slows its tumbling rate and increases the fluorescence polarization signal. Thus fluorescence polarization is proportional to the amount of bound fluorescent phosphopeptide. This assay can be used in a competitive mode, in which a fixed concentration of fluorescent peptide and antibody are added to a biological sample, and the presence of non-fluorescent phosphoprotein or phosphopeptide is recorded as a decrease in signal. It can also be used in a direct binding mode, in which phosphate addition (by e.g., a kinase) or removal (by e.g., a phosphatase) modulates antibody binding and thus polarization signal. In a specific embodiment, a fluorescence polarization assay is performed using the methods of Turek et al. (2001, Anal. Biochem. 299: 45-53), in which a product-specific anti-phosphorylated peptide-specific (e.g., anti-phospho-serine) antibody is used.

In another embodiment, a cell-based assay for phosphorylation is used. In a specific embodiment, signal transduction based on protein phosphorylation is visualized in vivo, e.g., in single living cells using fluorescent indicators, using methods such as those disclosed in Sato et al. (2002, Fluorescent indicators for imaging protein phosphorylation in single living cells, Nature Biotechnology 20(3): 287-94). Such sensors consist of two fluorescent protein molecules, separated by a flexible linker. The linker peptide contains a phosphorylation site and a phosphoprotein recognition element. Phosphorylation of the linker causes a conformational change that brings the two fluorescent proteins into close proximity, allowing FRET to occur and changing the fluorescent output of the system.

5.3. Agents that Modulate PDE1B Activity

The present invention also provides compositions for modulating the activity of PDE1B including, but not limited to the following agents, drugs, compounds or small molecules disclosed hereinbelow. The invention also provides compositions for modulating the activity of DARPP-32 or GluR1 AMPA receptor via modulation of the activity of PDE1B, including, but not limited to the following agents, drugs, compounds or small molecules disclosed hereinbelow. The invention also provides compositions for use in methods of treatment of a disorder, including but not limited to a PDE1B-related disorder and a dopamine D1 receptor intracellular signaling pathway disorder, wherein the compositions modulate the activity of PDE1B, including, but not limited to the following agents, drugs, compounds, or small molecules disclosed hereinbelow.

As disclosed hereinabove, without wishing to be bound by any particular theory, in one aspect of the invention, dopamine D1 receptors mediate the phosphorylation of DARPP-32 via dopamine D1 receptor intracellular signaling pathways. According to the invention, dopamine D1 receptor activation leads to adenylyl cyclase activation (and increased cAMP). cAMP activates protein kinase A (PKA; cAMP-dependent protein kinase) which phosphorylates downstream signal transduction pathway elements such as DARPP-32 and CREB. These signaling pathways are down-regulated or antagonized by phosphodiesterases (PDEs), including but not limited to PDE1B, which hydrolyzes cAMP to its 5'-monophosphate.

In another aspect of the invention, calcium-regulated PDE1B is an interface for regulating activity between a dopamine-regulated intracellular signaling pathway and another intracellular signaling pathway, including but not limited to a dopamine D1 receptor, dopamine D2 receptor, nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP) or endorphin intracellular signaling pathway Thus, any compound identified according to the methods of the invention that affects the above described interactions in a dopamine D1 intracellular signaling pathway may also serve as the basis of a therapeutic treatment for a PDE1B-related disorder or a dopamine D1 intracellular signaling pathway disorder, and therefore, all of the proteins that participate in such interactions may also be used in assays as described herein.

One of skill would understand that once identified as capable of modulating PDE1B activity in the methods of the present invention, the compound may be used therapeutically to modulate PDE1B activity in cells, e.g., neurons, in order to treat conditions in which PDE1B activity may be involved. Such conditions include, but are not limited to, a dopamine D1 intracellular signaling pathway.

The present invention further provides methods for performing rational drug design to develop drugs that can modulate activity of PDE1B and thereby ameliorate a disorder, including but not limited to a PDE1B-related disorder and a dopamine D1 receptor intracellular signaling pathway disorder. Such rational drug design can be performed using compounds that have been identified as inhibitors (or activators) of PDE1 as a starting point. Thus, the present invention provides screens and assays to allow more specific inhibitors (or activators) to be identified. Such methods of rational drug design are well-known in the art. In a specific embodiment, the rational drug design methods disclosed in U.S. patent application Ser. Nos. 09/419,379, by Bibb et al., entitled "Methods of Identifying Agents That Regulate Phosphorylation/Dephosphorylation in Dopamine Signaling," filed Oct. 15, 1999, and 09/687,959, by Bibb et al., entitled "Methods of Identifying Agents That Regulate Phosphorylation/Dephosphorylation in Dopamine Signaling," filed Oct. 13, 2000, incorporated herein by reference in their entireties, are used.

Indeed, potential modulators can be examined through the use of computer modeling using a docking program such as GRAM, DOCK, or AUTODOCK (Dunbrack et al., Folding & Design 2:27-42 (1997)), to identify potential modulators of PDE1B. These modulators can then be tested for their effect on PDE1B activity. This procedure can include computer fitting of potential modulators to the PDE1B complex to ascertain how well the shape and the chemical structure of the potential modulator will bind to PDE1B (see, e.g., Bugg et al., 1993, Scientific American (Dec.) 269(6):92-98; West et al., TIPS, 16:67-74 (1995)). Computer programs can also be employed to estimate the attraction, repulsion, and steric hindrance of the subunits with a modulator/inhibitor. Generally the tighter the fit, the lower the steric hindrances, and the greater the attractive forces, the more potent the potential modulator since these properties are consistent with a tighter binding constant. Furthermore, the more specificity in the design of a potential drug the more likely that the drug will not interact as well with other proteins. This will minimize potential side-effects due to unwanted interactions with other proteins.

Initially, compounds known to bind to PDE1B can be systematically modified by computer modeling programs until one or more promising potential analogs are identified. In addition systematic modification of selected analogs can then be systematically modified by computer modeling programs until one or more potential analogs are identified. Such analyses are well known to those of skill in the art and have been shown to be effective in the development of, e.g., HIV protease inhibitors (see, e.g., Lam et al., Science 263:380-384 (1994); Wlodawer et al., Ann. Rev. Biochem. 62:543-585 (1993); Appelt, Perspectives in Drug Discovery and Design 1:23-48 (1993); Erickson, Perspectives in Drug Discovery and Design 1:109-128 (1993)).

Any of the potential agents or targets for the potential agents (e.g., PDE1B or DARPP-32) can be labeled. Suitable labels include enzymes (e.g., alkaline phosphatase or horseradish peroxidase), fluorophores (e.g., fluorescein isothiocyanate (FITC), phycoerythrin (PE), Texas red (TR), rhodamine, free or chelated lanthanide series salts, especially Eu3+, to name a few fluorophores), chromophores, radioisotopes, chelating agents, dyes, colloidal gold, latex particles, ligands (e.g., biotin), chemiluminescent agents, magnetic beads or magnetic resonance imaging labels. When a control marker is employed, the same or different labels may be used for the receptor and control marker.

In embodiments wherein a radioactive label, such as the isotopes $^{3}$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re is used, standard counting procedures known in the art may be utilized.

In embodiments wherein the label is an enzyme, detection may be accomplished by any of the presently utilized colorimetric, spectrophotometric, fluorospectrophotometric, amperometric or gasometric techniques known in the art.

A direct label is an example of a label that can be used according to the methods of the present invention. A direct label is an entity that, in its natural state, is readily visible, either to the naked eye (for example, by visual inspection through a compound or dissecting light microscope), or with the aid of an optical filter and/or applied stimulation, e.g., U.V. light to promote fluorescence. Examples of colored labels that can be used according to the methods of the present invention, include metallic sol particles, for example, gold sol particles such as those disclosed by Leuvering (U.S. Pat. No. 4,313,734); dye sol particles such as disclosed by Gribnau et al. (U.S. Pat. No. 4,373,932) and May et al. (WO 88/08534); dyed latex such as disclosed by May et al. (WO 88/08534), Snyder (EP-A 0280 559 and 0 281 327); or dyes encapsulated in liposomes as disclosed by Campbell et al. (U.S. Pat. No. 4,703,017).

Other direct labels include a radionucleotide, a luminescent moiety, or a fluorescent moiety including, but not limited, to, e.g., a modified/fusion chimera of green fluorescent protein (as disclosed in U.S. Pat. No. 5,625,048, issued Apr. 29, 1997, and WO 97/26333, published Jul. 24, 1997, each of which is incorporated herein by reference in its entirety).

In addition to these direct labeling devices, indirect labels comprising enzymes can also be used according to the present invention. Various types of enzyme-linked immunoassays are well known in the art, for example, enzyme-linked immunoassays using alkaline phosphatase, horseradish peroxidase, lysozyme, glucose-6-phosphate dehydrogenase, lactate dehydrogenase, or urease. These and other similar assays are well known in the art and are disclosed, e.g., in Engvall (1980, "Enzyme Immunoassay ELISA and EMIT," in Methods in Enzymology, 70: 419-439) and in U.S. Pat. No. 4,857,453.

In certain embodiments, proteins can be labeled by metabolic labeling. Metabolic labeling occurs during in vitro incubation of the cells that express the protein in the presence of culture medium supplemented with a metabolic label, such as [$^{35}$S]-methionine or [$^{32}$P]-orthophosphate. In addition to metabolic (or biosynthetic) labeling with [Cl$_2$]-methionine, the invention further contemplates labeling with [$^{14}$C]-amino acids and [$^3$H]-amino acids (with the tritium substituted at non-labile positions) (see, e.g., U.S. patent application Ser. Nos. 09/419,379, by Bibb et al., entitled "Methods of Identifying Agents That Regulate Phosphorylation/Dephosphorylation in Dopamine Signaling," filed Oct. 15, 1999, and 09/687,959, by Bibb et al., entitled "Methods of Identifying Agents That Regulate Phosphorylation/Dephosphorylation in Dopamine Signaling," filed Oct. 13, 2000, incorporated herein by reference in their entireties).

5.4. Diagnostic and Therapeutic Methods

As disclosed herein, the invention provides agents, drugs, compounds and compositions that modulate the activity or expression of PDE1B. The invention also provides a method for treating a disorder, including but not limited to a PDE1B-related disorder and a dopamine D1 receptor intracellular signaling pathway disorder, in a patient in need thereof, comprising administering to the patient an agent that alters the activity of PDE1B, wherein PDE1B activity modulates phosphorylation of DARPP-32 and/or the GluR1 AMPA receptor.

The present invention provides methods for treating a disorder, including but not limited to a PDE1B-related and dopamine D1 receptor intracellular signaling pathway disorder, in an individual (e.g., a patient) or an animal subject by administering an effective amount of a compound of the invention to modulate PDE1B activity. In one embodiment, the agent promotes or increases the activity of PDE1B. In another embodiment, the agent inhibits or decreases the activity of PDE1B. In certain embodiments, the agent promotes (or increases) or inhibits (or decreases) the activity of a dopamine D1 receptor intracellular signaling pathway via modulation of PDE1B activity.

In certain embodiments, the invention provides a method for treating a disorder, including, but not limited to, a PDE1B-related and a dopamine D1 receptor intracellular signaling pathway disorder, in a patient in need thereof, comprising administering to the patient an agent that modulates PDE1B activity, wherein the phosphorylation of DARPP-32 at Thr34, and/or the phosphorylation of GluR1 AMPA receptor at Ser845, is modulated. In specific embodiments, the agent modulates the activity of PDE1B by binding to PDE1B.

In one embodiment, a subject in need of such treatment is administered an amount of a compound of the present invention sufficient to modulate PDE1B activity, and modulate DARPP-32 activity, GluR1 AMPA receptor activity, and/or the activity of a intracellular signaling pathway including, but not limited to a dopamine D1 receptor, dopamine D2 receptor, nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP) or endorphin intracellular signaling pathway.

The invention provides methods of administering an agent (or drug or compound) of the invention that can ameliorate a symptom of a disorder, including but not limited to a PDE1B-related and dopamine D1 receptor intracellular signaling pathway disorder, in a patient or subject exhibiting the symptom. In certain embodiments, the invention provides methods of administering an agent identified by the methods disclosed herein, that can ameliorate a symptom of said disorder in a patient or subject exhibiting the symptom.

In another embodiment, the invention provides a method for treating a disorder, including but not limited to a PDE1B-related and dopamine D1 receptor intracellular signaling pathway disorder, in a patient in need thereof, comprising administering to the patient an agent that modulates PDE1B activity, wherein phosphorylation of DARPP-32 and/or GluR1 AMPA receptor is modulated. In a specific embodiment, PDE1B activity is inhibited.

In another embodiment, the invention provides a method for treating a disorder, including but not limited to a PDE1B-related and dopamine D1 receptor intracellular signaling pathway disorder, in a patient in need thereof comprising administering to the patient an agent that modulates PDE 1B activity and modulates the phosphorylation of Thr34-phosphorylated DARPP-32.

In another embodiment, the invention provides a method for treating a disorder characterized by an increase or a decrease in phosphorylation-dependent activation of GluR1 AMPA receptors comprising administering an effective amount of a compound that modulates the activity of PDE1B.

In a particular embodiment, a method of the invention is used to treat a disorder, including but not limited to a PDE1B-related and dopamine D1 receptor intracellular signaling pathway disorder, that is related to a symptom and/or disease state characteristic of a PDE1B-related and/or a dopamine D1 receptor intracellular signaling pathway disorder.

In a particular embodiment, the invention provides a method for treating Parkinson's disease in a patient in need thereof; comprising administering to the patient an agent that inhibits PDE1B activity, wherein phosphorylation of Thr-34-DARPP-32 and/or Ser845-GluR1 AMPA receptor is increased.

Preferably the agent, compound or composition administered in the method of treatment can cross through the blood brain barrier in sufficient quantities and at a sufficient rate so as to allow the treatment of the disorder and thereby, the condition or disease. In one such embodiment, the agent is administered intravenously. In another embodiment, the agent is administered orally. More preferably the agent can cross the blood brain barrier without a carrier (for methods and routes of administration, see Section 5.6).

The invention also provides a method for diagnosing a disorder, including but not limited to a PDE1B-related and dopamine D1 receptor intracellular signaling pathway disorder, in a subject suspected of having such a disorder, said method comprising determining a level of PDE1B activity in a sample from said subject, wherein a greater level of PDE1B activity in the sample from said subject relative to a control level of PDE1B activity in a control sample from a subject that does not have such a disorder indicates that said subject has said disorder. In specific embodiments, the subject is a human.

In certain embodiments, the level of PDE1B activity is determined by measuring phosphorylation of phospho-Thr34 of DARPP-32 or phospho-Ser845 of GluR1 AMPA receptor. In other embodiments, the level of PDE1B activity is a level of PDE1B mRNA, and said level of PDE1B mRNA is determined by methods well known in the art, e.g., by in situ hybridization. In other embodiments, the level of PDE1B activity is a level of PDE1B protein, and said protein level is determined by methods well known in the art, e.g., by immunoblotting.

The invention also provides a method for detecting a disorder, including but not limited to a PDE1B-related and dopamine D1 receptor intracellular signaling pathway disorder, in vivo in a subject suspected of having such a disorder, said method comprising
 (a) administering an agent that specifically binds PDE1B, said agent being conjugated to a label detectable by an imaging method;
 (b) after said administration, waiting sufficient time for said agent to bind specifically to PDE1B in said subject and for unbound agent to clear to background levels in said subject; and
 (c) then imaging said subject with said imaging method to detect levels of PDE1B in said subject.
In certain embodiments, the subject is human.

5.5. Animal Models

According to the methods of the present invention, an animal model may be used for testing compounds identified by the screening methods of the present invention, wherein the compound is tested for functional utility using the animal model. According to the methods of the invention, an animal model may be a wild-type animal (as a model, e.g., for a normal or wild-type physiological or behavior state). Alternatively, the animal model may be a model for a disease or disorder, including but not limited to a PDE1B-related or dopamine D1 receptor intracellular signaling pathway disorder. Such animal models may be used in assays to screen for compounds that modulate the activity of PDE1B, or that ameliorate the symptoms of a disease or disorder. Such animals can be mice, rats, hamsters, sheep, pigs, cattle, etc., and are preferably non-human mammals.

According to the invention, animal models may be employed that have, in certain embodiments, an altered physiological regulation of the nervous system such that the animal or tissues derived from it can be utilized for screening of potential therapeutic agents and/or therapeutic regimens that act at the intracellular level, especially at the level of intracellular signaling pathways, including but not limited to a nitric oxide, norepinephrine, neurotensin, CCK, VIP, serotonin, glutamate, GABA, acetylcholine, adenosine, natriuretic peptide (e.g., ANP, BNP, CNP) or endorphin intracellular signaling pathway. Drugs that can reverse any of the defects exhibited by such an animal model act at some point in the intracellular signaling cascade and are thus of potential use therapeutically. Additionally, since some defects occur at the behavioral level, the affectation or alteration of these can have a high predictive value for therapeutic use in modification of such behaviors.

According to the methods of the invention, animal models thus can be used, as screening tools to elucidate the mechanisms of the various protein phosphorylation steps involved in both normal and diseased patient populations. For example, an animal model can thus be utilized to assess the response to a variety of potential therapeutic strategies and therapeutic agents which can thus be used in the treatment of patients suffering from a variety of neurological diseases and disturbances.

Using animal models, various small molecule drugs can be screened for potentially advantageous effects, including enhanced potency as well as minimization of side effects. Typical candidates for such screening may be obtained from any of several commercially available drug libraries.

Specific neurological and behavioral diseases for which an animal model can be utilized include, but are not limited to, PDE1B-related disorders and dopamine D1 receptor intracellular signaling pathway disorders, as disclosed herein. By utilizing the various characteristic responses an animal to endogenous and exogenous agents, and comparing these responses to an animal treated with a potential therapeutic agent, an assessment of the utility of the potential therapeutic agent in a particular disease state can be made. For instance, the potential therapeutic agent can be administered to an animal model for a particular disease or disorder, and its response to dopamine can be monitored. Comparison with the response to dopamine in a normal, wild-type mouse can then provide an indication of the value of the potential therapeutic agent.

Another aspect of the invention is a method for selecting a therapeutic agent for possible use in the treatment of a disorder, including but not limited to a PDE1B-related and dopamine D1 receptor intracellular signaling pathway disorder, which comprises administering a suspected therapeutic agent to an animal model, and measuring and/or determining the putative therapeutic agent's effect on any phenotypic characteristics which may be believed to be related to said disorder.

In one embodiment of this aspect of the invention, a suspected therapeutic agent is administered to an animal model, and a test response to dopamine is measured for the animal model, wherein the normal response of the animal model in the absence of a therapeutic agent is characteristically different than that of wild-type animals. The potential therapeutic agents are selected on the basis of whether there is a statistical significance between test response and the normal response. Potential therapeutic agents are selected that show a statistically significant change in the characteristic measured/determined. In a preferred embodiment, the response of the animal model in the absence of a therapeutic agent is characteristically different than that of wild-type animals to which the potential therapeutic has not been administered.

Yet another aspect of the present invention is a method for selecting a therapeutic agent for possible use in the treatment of Parkinson's disease which comprises administering a suspected therapeutic agent to an animal model, and measuring and/or determining the putative therapeutic agent's effect on any of the phenotypic characteristics which may be believed to be related to Parkinson's disease.

Animal models that may be used according to the methods of the invention include, but are not limited, to the animal models disclosed hereinbelow.

In one embodiment, a homozygous PDE1B knockout mouse may be used, as disclosed herein, in an additional test or assay to validate or confirm that a candidate agent modulates PDE1B activity as disclosed herein. In one embodiment, the invention provides an animal model that is a PDE1B-deficient, e.g., null or "knockout" mouse, that comprises a homozygous disruption in its endogenous PDE1B gene, wherein said disruption prevents the expression of a functional PDE1B protein, and further wherein the phenotype of said knockout mouse relative to a mouse having a wild type PDE1B gene comprises absence of PDE1B enzymatic activity when assayed for cAMP or cGMP hydrolysis. In certain embodiments, the disruption comprises a targeted disruption of the PDE1B catalytic site. In other embodiments, the disruption comprises an insertion into the coding region of the PDE1B gene.

The knockout mouse contains a non-functional allele for the gene that naturally encodes and expresses functional PDE1B. A knockout mouse containing two non-functional alleles for the gene that naturally encodes and expresses functional PDE1B, is therefore unable to express functional PDE1B.

Non-functional alleles can be generated in any number of ways that are well known in the art, all of which may be used in the present invention. In preferred embodiments, a non-functional allele is made defective by an insertion or substitution of extraneous DNA into the coding region PDE1B allele; preferably the coding region for the catalytic domain. In some embodiments, the insertion contains a signal to terminate transcription prior to the transcription of a region of the allele that encodes PDE1B. In such embodiments, it is still more preferred to remove a section of DNA from the coding region for the catalytic domain of PDE1B and replacing it with the above insertion.

The PDE1B knockout mouse of the invention has phenotype that comprises an increased response to dopamine and/or hyperactivity, as disclosed in Section 6. In other embodiments, the increased response to dopamine is evidenced by increased phosphorylation of DARPP-32 at Thr34 and/or GluR1 AMPA receptor at Ser 845.

In other embodiments, the phenotype of the PDE1B knockout mouse relative to a mouse having a wild type PDE1B gene further comprises a phenotype selected from the group consisting of: exhibition of significantly more exploratory behavior during the first 30 minutes of a test period for horizontal locomotor activity, exhibition of significantly more hyperactivity after administration of methamphetamine treatment, exhibition of significantly longer path length in acquisition of a Morris water maze, exhibition in striatal slices from said mouse of increased levels of phospho-Thr34 or phospho-Ser845 upon administration of a D1 receptor agonist, and exhibition in nucleus accumbens slices from said mouse of increased levels of phospho-Thr34 or phospho-Ser845 upon administration of a D1 receptor agonist. It will appreciated by one of skill in the art that a wild-type mouse in which PDE1B is inhibited experimentally, e.g., through administration a compound of the invention, may, in certain embodiments, exhibit some and/or all of the above-described phenotypic characteristics of a PDE1B knockout mouse.

As disclosed herein, the PDE1B knockout animal of the invention is preferably a mouse, since mice offer distinct advantages as laboratory research animals. However, it will be recognized that any other animal having the PDE1B protein will be amenable to the methods of the instant invention. Such animals can be mice, rats, hamsters, sheep, pigs, cattle, etc., and are preferably non-human mammals.

Methods for producing knockout mice are well known in the art. The method comprises obtaining genomic DNA encoding PDE1B, constructing a vector containing said genomic DNA and a marker gene, wherein said marker gene is placed within the exon of said genomic DNA. The vector is then electroporated into embryonic stem (ES) cells and an embryonic stem (ES) cell is selected that has integrated the vector into its genome, wherein the selected cell has integrated the marker gene into the endogenous site of the gene for PDE1B in the mouse genome. The cell is then injected into a mouse blastocyst, which is then re-implanted into a pseudopregnant female mouse, which gives birth to a chimeric mouse containing a defective allele for PDE1B in its germ line. The chimeric mouse is then mated to a mouse of a standard in-bred line to generate a heterozygous knockout mouse. Two heterozygous mice are then bred generating a homozygous knockout mouse offspring.

Methods for generating cells having targeted gene modifications through homologous recombination are known in the art (see, e.g., Chappel, U.S. Pat. No. 5,272,071; and PCT publication No. WO 91/06667, published May 16, 1991; U.S. Pat. No. 5,464,764; Capecchi et al., issued Nov. 7, 1995; U.S. Pat. No. 5,627,059, Capecchi et al. issued, May 6, 1997; U.S. Pat. No. 5,487,992, Capecchi et al., issued Jan. 30, 1996). Methods for constructing homologous recombination vectors and homologous recombinant animals are described further in Thomas and Capecchi, 1987, Cell 51: 503; Bradley, 1991, Curr. Opin. Bio/Technol. 2: 823-29; and PCT Publication Nos. WO 90/11354, WO 91/01140, and WO 93/04169.

In one embodiment, the invention provides a PDE1B knockout mouse that is generated by:
(a) obtaining genomic DNA encoding a portion of PDE1B;
(b) constructing a vector containing said genomic DNA and a marker gene, wherein said marker gene is inserted into an exon of said genomic DNA;
(c) introducing said vector into mouse embryonic stem cells by electroporation;
(d) selecting a cell that has a disrupted PDE1B gene due to the integration of said vector into its genome by homologous recombination into the endogenous PDE1B gene;
(e) injecting said cell into a mouse blastocyst, thereby forming a chimeric blastocyst;
(f) implanting said resultant chimeric blastocyst into a pseudopregnant mouse wherein said pseudopregnant mouse gives birth to a chimeric mouse containing a mutant PDE1B gene in its germ line;
(g) breeding said chimeric mouse to generate a heterozygous mouse comprising a disrupted PDE1B gene thereby generating a mouse heterozygous for said disrupted PDE1B gene; and
(h) mating together a male and a female mouse each heterozygous for said disrupted PDE1B gene and selecting progeny that are homozygous for said disrupted PDE gene.

In another embodiment, a mouse model of Parkinson's disease is used (Uhl et al., 1985, Lancet 1:956-57; Mokry, 1995, Experimental models and behavioral tests used in the study of Parkinson's Disease, Physiol. Res. 44: 143-50; Du, 2001, Proc. Natl. Acad. Sci. USA 98: 14669-14674). Such a model animal system may be used to screen for compounds useful in the treatment of Parkinson's disease due to their effect on dopamine D1 intracellular signaling pathways. In an alternative embodiment, a rat model of Parkinson's disease is used. In a specific embodiment, rats are unilaterally (i.e. in one hemisphere) injected with 6-OHDA (6-hydroxydopamine; a dopaminergic neurotoxin) according to standard methods. The 6-OHDA is selectively taken up by dopaminergic neurons and kills the neurons. Such 6-OHDA-lesioned animals are considered an animal model of Parkinson's disease (see Section 6).

In another embodiment, a mouse model of schizophrenia is used (Sipes et al., 1995, 8-OH-DPAT disruption of prepulse inhibition in rats: reversal with (+)WAY 100,135 and localization of site of action, Psychopharmacology (Berl) 117(1): 41-8; Cao et al., 2002, Brain Research 937: 32-40). Such a model animal system may be used to screen for compounds useful in the treatment of schizophrenia due to their effect on dopamine D1 intracellular signaling pathways.

In other embodiments, a rat model for attention-deficit disorder (ADD) or attention-deficit hyperactivity disorder (ADHD) is used (see, e.g., Hansen et al., 1999, Alcohol responsiveness, hyperreactivity and motor restlessness in an animal model for attention-deficit hyperactivity disorder, Psychopharmacology 146: 1-9; Russell, 2002, Behavioral Brain Res. 130: 191-196). Russell, for example, discloses a spontaneously hypertensive rat model that is a genetic model for ADHD. Such a model animal system may be used to screen for compounds useful in the treatment of ADHD due to their effect on dopamine D1 intracellular signaling pathways.

In another embodiment, a mouse model of pain is used (e.g., O'Callaghan et al., 1975, Quantification of the analgesic activity of narcotic antagonists by a modified hot-plate procedure, J. Pharmacol Exp Ther 192: 497-505; Guarna et al., 2002, J. Neurochem. 80:271-277; Menéndez et al., 2002, Unilateral hot plate test: a simple and sensitive method for detecting central and peripheral hyperalgesia in mice, J. Neurosci. Methods 113:91-97). Guarna et al. discloses a mouse model for acute thermonociception. Menéndez et al. discloses a mouse model for central and peripheral hyperalgesia. Such a model animal system may be used to screen for compounds useful in the treatment of pain due to their effect on dopamine D1 intracellular signaling pathways.

In another embodiment, a rat model of addiction (e.g., cocaine addiction) is used (Caine and Koob, 1995, Pretreatment with the dopamine agonist 7-OH-DPAT shifts the cocaine self-administration dose-effect function to the left under different schedules in the rat, Behav. Pharmacol 6: 333-347; Orsini et al., 2002, Brain Research 925:133-140). Such a model animal system may be used to screen for compounds useful in the treatment of drug abuse or addiction due to their effect on dopamine D1 intracellular signaling pathways.

In another embodiment, an animal or tissue model of epilepsy is used (see, e.g., Paschoa et al., 1997, Seizure patterns in kindling and cortical stimulation models of experimental epilepsy, Brain Res. 770: 221-227; Kokaia, 1995, Exper. Neurol. 133:215-224; Merlin, 1999, J. Neurophysiol. 82: 1078-1081; Merlin, 2001, J. Neurophysiol. 87:621-625). Kokaia (1995, Exper. Neurol. 133:215-224) discloses a mouse model of epilepsy. Merlin (1999, J. Neurophysiol. 82: 1078-1081; 2001, J. Neurophysiol. 87:621-625) discloses a guinea pig hippocampal slice model of epilepsy. Such model animal or tissue systems may be used to screen for compounds useful in the treatment of epilepsy due to their effect on dopamine D1 intracellular signaling pathways.

In another embodiment, the animal model is a homozygous DARPP-32 knockout mouse (see U.S. Pat. No. 5,777,195, by Fienberg et al., issued Jul. 7, 1998; U.S. Pat. No. 6,013,621, by Nishi et al., issued Jan. 11, 2000; and Fienberg et al., 1998, Science 281:838-842; each of which is incorporated herein by reference in its entirety). In one embodiment, the homozygous DARPP-32 knockout mouse may be used, in an additional test or assay to validate or confirm that a candidate agent modulates PDE1B activity. In a specific embodiment, the validation may be carried out according to the methods described in Nishi et al. (U.S. Pat. No. 6,013,621, issued Jan. 11, 2000). When such an agent is identified that modulates the activity of PDE1B, the presence of, or administration of, the agent in the DARPP-32 knockout mouse should diminish the magnitude of activation of cAMP responsive element binding protein (CREB), AMPA receptor (e.g., GluR1 AMPA receptor), cAMP, cGMP, PKA, PKG, PP-2B, PP-1, calcium channels, Na/K ATPase and NMDA receptor, relative to the absence or non-administration of the agent.

5.6. Pharmaceutical Compositions and Formulations

The present invention also provides pharmaceutical compositions of the agents (or drugs or compounds) of the invention disclosed herein. The invention encompasses pharmaceutical compositions for regulating PDE1B activity, and for treating a disorder, including but not limited to a PDE1B-related and dopamine D1 receptor intracellular signaling pathway disorder. Because in certain embodiments, a decrease of normal function can result in the development of a phenotype of the above-listed diseases or disorders (e.g., Parkinson's disease), an increase in PDE1B activity, or activation of a downstream element in the dopamine D1 receptor intracellular signaling pathway facilitates amelioration of a symptom in individuals exhibiting a symptom of such a disorder.

In one aspect, the invention provides methods of administering an agent that can ameliorate a symptom of a PDE1B-related disorder or dopamine D1 intracellular signaling pathway disorder in a patient or subject exhibiting the symptom. In certain embodiments, symptoms of a certain disorder (e.g., Parkinson's disease) may be ameliorated by decreasing levels of PDE1B activity. In other embodiments, symptoms of the disorder may be ameliorated by increasing levels of PDE1B activity.

The present invention provides pharmaceutical compositions of the agents, drugs or compounds of the invention disclosed hereinabove. The agent, drug or compound, or their physiologically acceptable salts or solvates, may be formulated for administration for injection, or for oral, topical, nasal, inhalation, insufflation (either through the mouth or the nose) buccal, parenteral, rectal administration or other forms of administration. The invention provides pharmaceutical compositions comprising effective amounts of an agent(s) of the invention together with pharmaceutically acceptable diluents, preservatives, solubilizers, emulsifiers, adjuvants, excipients and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimerosal, benzyl alcohol) and bulking substances (e.g., lactose, mannitol).

The compositions may also be incorporated into particulate preparations of polymeric compounds such as polylactic acid, polyglycolic acid, etc. or liposomes. Hyaluronic acid may also be used. Biocompatible absorbable polymers may be selected from the group consisting of aliphatic polyesters, copolymers and blends, which include, but are not limited to, homopolymers and copolymers of lactide (which include D-, L-, lactic acid and D-, L- and meso lactide), glycolide (including glycolic acid), epsilon-caprolactone, p-dioxanone (1,4-dioxan-2-one, which is disclosed in U.S. Pat. No. 4,052,988), alkyl substituted derivatives of p-dioxanone (i.e., 6,6-dimethyl-1,4-dioxan-2-one which is disclosed in U.S. Pat. No. 5,703,200), triethylene carbonate (1,3-dioxan-2-one), alkyl substituted derivatives of 1,3-dioxanone (which are disclosed in U.S. Pat. No. 5,412,068), delta-valerolactone, beta-butyrolactone, gamma-butyrolactone, epsilon-decala tone, hydroxybutyrate, hydroxyvalerate, 1,4-dioxepan-2-one (disclosed in U.S. Pat. No. 4,052,988 and its dimer 1,5,8,12-tetraoxacyclotetradecane-7,14 dione), 1,5-dioxepan-2-one, and polymer blends thereof.

Such compositions may influence physical state, stability, rate of in vivo release, and rate of in vivo clearance of the present proteins and derivatives. See, e.g., Remington s Pharmaceutical Sciences, 18th ed., (1990, Mack Publishing Co., Easton, Pa. 18042) pages 1435-1712). The compositions may be prepared in liquid form, or be in dried powder, such as lyophilized form.

Contemplated for use herein are oral solid dosage forms, which are disclosed generally in Remington s Pharmaceutical Sciences, 18th Ed. 1990 (Mack Publishing Co. Easton Pa. 18042) at Chapter 89. Solid dosage forms include tablets, capsules, pills, troches or lozenges, cachets or pellets. Also, liposomal or proteinoid encapsulation may be used to formulate the present compositions (as, for example, proteinoid microspheres reported U.S. Pat. No. 4,925,673). Liposomal encapsulation may be used and the lipomes may be derivatized with various polymers (e.g., U.S. Pat. No. 5,013,556). A description of possible solid dosage forms for the therapeutic is given by Marshall, K. In: Modern Pharmaceutics Edited by G. S. Banker and C. T. Rhodes Chapter 10, 1979). In general, the formulation will include the agent and inert ingredients (which allow for protection against the stomach environment and release of the biologically active material in the intestine).

To ensure full gastric resistance a coating impermeable to at least pH 5.0 is useful. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L3OD, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings that make the tablet easier to swallow. Capsules may consist of a hard shell (such as gelatin) for delivery of dry therapeutic, i.e., powder; for liquid forms, a soft gelatin shell may be used. The shell material of cachets may be thick starch or other edible paper. For pills, lozenges, molded tablets or tablet triturates, moist massing techniques can be used.

The therapeutic can be included in the formulation as fine multi-particulates in the form of granules or pellets. The formulation of the material for capsule administration can also be as a powder, lightly compressed plugs or even as tablets. The therapeutic can also be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the therapeutic with an inert material or filler. These diluents or fillers can include carbohydrates, especially mannitol, a-lactose, anhydrous lactose, cellulose (e.g., microcrystalline cellulose), sucrose, calcium hydrogen phosphate modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include, but are not limited to, starch (e.g., potato starch or the commercial disintegrant based on starch, Explotab). Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch (e.g., pregelatinised maize starch) and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) can both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes, talc and silica. Soluble lubricants may also be used such as sodium lauryl sulfate, magnesium lauryl sulfate, polyethylene glycol of various molecular weights, Carbowax 4000 and 6000.

Glidants that can improve the flow properties of the drug during formulation and to aid rearrangement during compression can be added. The glidants can include starch, talc, pyrogenic silica and hydrated silicoaluminate.

To aid dissolution of the therapeutic into the aqueous environment a surfactant can be added as a wetting agent. Surfactants may include anionic detergents such as sodium lauryl sulfate, dioctyl sodium sulfosuccinate and dioctyl sodium sulfonate. Cationic detergents can be used and can include benzalkonium chloride or benzethomium chloride. The list of potential non-ionic detergents that can be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants can be present in the formulation of the protein or derivative either alone or as a mixture in different ratios.

Additives that potentially enhance uptake of the agent are, for example, the fatty acids oleic acid, linoleic acid and linolenic acid.

Controlled release oral formulation may be desirable. The agent can be incorporated into an inert matrix that permits release by either diffusion or leaching mechanisms, e.g., gums. Slowly degenerating matrices may also be incorporated into the formulation. Some enteric coatings also have a delayed release effect.

Another form of a controlled release of this therapeutic is by a method based on the Oros therapeutic system (Alza Corp.), i.e. the drug is enclosed in a semipermeable membrane, which allows water to enter and to push the drug out through a single small opening due to osmotic effects.

Other coatings may be used for the formulation. These include a variety of sugars that can be applied in a coating pan. The therapeutic agent can also be given in a film coated tablet and the materials used in this instance are divided into two groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid.

A mix of materials can be used to provide the optimum film coating. Film coating may be carried out in a pan-coater or in a fluidized bed or by compression coating.

Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Nasal delivery of the agent is also contemplated. Nasal delivery allows the passage of the protein to the blood stream directly after administering the therapeutic product to the nose, without the necessity for deposition of the product in the lung. Formulations for nasal delivery include those with dextran or cyclodextran.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations disclosed previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

5.6.1. Dosage Determinations

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful closes in humans. Levels in plasma may be measured, for example, by high performance liquid chromatography.

5.6.2. Routes of Administration

The component or components of a therapeutic composition of the invention may be introduced parenterally, topically, or transmucosally, e.g., orally, nasally, or rectally, or transdermally. Preferably, administration is parenteral, e.g., via intravenous injection, and also including, but not limited to, intra-arteriole, intramuscular, intradermal, subcutaneous, intraperitoneal, intraventricular, and intracranial administration. In preferred embodiments, the component or components of a therapeutic composition of the invention is introduced orally or parentally.

In preferred embodiments of the invention, an agent (or drug or compound) can cross and more preferably readily pass through the blood-brain barrier, which permits, e.g., oral, parenteral or intravenous administration. Alternatively, the agent can be modified or otherwise altered so that it can cross or be transported across the blood brain barrier. Many strategies known in the art are available for molecules crossing the blood-brain barrier, including but not limited to, increasing the hydrophobic nature of a molecule; introducing the molecule as a conjugate to a carrier, such as transferring, targeted to a receptor in the blood-brain barrier, or to docosahexaenoic acid etc.

In another embodiment, an agent of the present invention is administered via the standard procedure of drilling a small hole in the skull to administer the agent.

In another embodiment, the molecule can be administered intracranially or, more preferably, intraventricularly. In another embodiment, osmotic disruption of the blood-brain barrier can be used to effect delivery of agent to the brain (Nilaver et al., Proc. Natl. Acad. Sci. USA 92:9829-9833 (1995)). In yet another embodiment, an agent can be administered in a liposome targeted to the blood-brain barrier. Administration of pharmaceutical agents in liposomes is known (see Langer, Science 249:1527-1533 (1990); Treat et al., in Liposomes in the Therapy of infectious Disease and Cancer, Lopez-Berestein and Fidler (eds.), Liss, New York, pp. pp. 317-327 and 353-365 (1989). All of such methods are envisioned in the present invention.

Although some predictions have been made concerning the ability of molecules to pass through the blood-brain barrier, these predictions are at best speculative. The rate and extent of entry of a compound into the brain are generally considered to be determined by partition coefficient, ionization constant(s), and molecular size. No single partition solvent system has emerged as a universally applicable model for brain penetration, although the octanol water system has received particular attention, and Hansch and coworkers have suggested that a partition coefficient in this system of about 100 is optimal for entry into the central nervous system (CNS) (Glave and Hansch, J. Pharm. Sci. 61:589 (1972); Hansch et al., J. Pharm. Sci. 76:663 (1987)). In practice, the octanol-water partition system only provides a qualitative indication of the capability of a compound to cross the blood-brain barrier. For example, comparisons between known histamine H2 receptor antagonists suggest that there is no such simple relationship between their brain penetration and octanol water partition coefficients (Young et al., J. Med. Chem. 31:656 (1988)). Other factors, besides the octanol-water partition influence the propensity to cross the blood-brain barrier. Comparison of the ability of histamine H2 receptor antagonists to cross the blood-brain barrier suggests that brain penetration may increase with decreasing over-all hydrogen binding ability of a compound (Young et al., J. Med. Chem. 31:656 (1988)). Begley et al. (J. Neurochem. 55:1221-1230 (1990)) herein incorporated by reference in its entirety, discloses the ability of cyclosporin A to cross the blood-brain barrier. Methodology as used by Begley et al. includes: (1) measuring the brain uptake index (BUT) with the equation for a tritiated agent compound:

$BUI=[(brain\ ^3H/brain\ ^{14}C)/(injectate\ ^3H/injectate\ ^{14}C)] \times 100$ where the $^{14}C$ reference compound is $^{14}C$ butanol or an analogous solvent; (2) Brain perfusion studies; (3) Intravenous bolus injection studies; and (4) Studies with cultured cerebral capillary endothelium.

In another embodiment, the therapeutic compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss: New York, pp. 317-327 and 353-365 (1989)). To reduce its systemic side effects, this may be a preferred method for introducing the agent.

In another embodiment, the therapeutic compound can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem. 23:61 (1983); see also Levy et al., Science 228: 190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)). Other controlled release systems are discussed in the review by Langer (Science 249:1527-1533 (1990)).

The following experimental examples are offered by way of illustration and not by way of limitation.

6. EXAMPLE 1

Phosphodiesterase 1B (PDE1B) Knockout Mice Exhibit Exaggerated Locomotor Hyperactivity and DARPP-32 Phosphorylation in Response to Dopamine Agonists and Display Impaired Spatial Learning This example demonstrates that enhancement of cyclic nucleotide signaling by inactivation of PDE1B-mediated cyclic nucleotide hydrolysis plays a significant role in dopaminergic function through the DARPP-32 and related transduction pathways.

Using homologous recombination, mice were generated that lacked phosphodiesterase-mediated (PDE1B) cyclic nucleotide hydrolyzing activity. PDE1B-/- ("null") mice showed exaggerated hyperactivity after acute D-methamphetamine administration. Striatal slices from PDE1B-/- mice exhibited increased levels of phospho-Thr34 DARPP-32 and phospho-Ser845 GluR1 after dopamine D1 receptor agonist or forskolin stimulation. PDE1B-/- and PDE1B+/- (heterozygous) mice also exhibited Morris maze spatial-learning deficits.

6.1. Materials and Methods
6.1.1. PDE1B Knockout Mouse

Two overlapping clones, TRC2 and TRC4, corresponding to exons 2-13 of the PDE1B gene, were obtained by screening an I-129/SvJ Lambda Dash II mouse genomic library as described (Reed, T. R. et al. 1998. Mamm. Gen. 9:571-576). A 0.8 kb XbaI fragment containing exons 4 and 5 and a small portion of the multiple cloning site of pBluescript II KS(-) (Stratagene, Inc., La Jolla, Calif.) was blunt-end ligated into the BamHI site of the targeting vector. A 5 kb AccI/KpnI fragment containing genomic DNA 3' of exon 9, including 2.4 kb of non-coding sequence 3' to exon 13, was blunt-end ligated into the ClaI site of the targeting vector (see FIG. 1A). The targeting vector backbone pGKKOV has been described by Li et al. (1996. EMBO J. 15:714-724). This vector is derived from pBluescript II SK(+) with an HSV-TK selectable marker and a PGK-HPRT selectable marker inserted into the KpnI and HindIII sites, respectively, of the multiple cloning site. The orientation of inserts was determined by sequencing.

The targeting vector (50 μg) was linearized with NotI and electroplated into $9.3 \times 10^6$ E14TG2a embryonic stem (ES) cells. ES cells were plated in ten 100 cm tissue culture plates on $2.2 \times 10^6$ mitomycin C-treated mouse embryonic fibroblasts in 10 ml of DMEM per plate containing 15% ES cell qualified fetal calf serum (Life Technologies, Carlsbad, Calif.), 0.3 mM L-glutamine, 75,000 units of Pen/Strep, 60 units of LIF, and 0.009% β-mercaptoethanol supplemented with 2 μM Cytovene and 1×HAT (Life Technologies, Carlsbad, Calif.) for the selection process. Following 5 days of selection, 302 ES cell clones were selected and expanded in 24 well plates. Clones were screened by Southern blot analysis. Cells from two positive clones were injected into C57Bl/6 blastocysts and implanted into pseudopregnant females. Chimeric offspring were bred to C57Bl/6 mice (Charles River, Wilmington, Mass.) to produce heterozygous offspring that were bred to C57Bl/6 mice for two additional generations to give a total of 3 back-cross breedings. The offspring resulting from inter-breeding the $F_3$ generation were used for behavioral testing.

For behavioral testing, nulliparous $F_4$ generation PDE1B-deficient mice and their wild-type litter mates were used. Animals used for biochemistry were the offspring of third and fourth generation backcrossing. Mice were ear-marked on post-natal day 7 (P7) and weighed weekly beginning on P7 and ending on P112. Tail biopsies were obtained on P21 or P42. Litters were weaned on P28. Mice were housed in cages, same gender in each cage, with 2 to 4 mice per cage. Individual mice were excluded from testing if there were no same gender litter mates or if visible ocular defects were present. All procedures were performed by the same experimenter who was blinded to genotypes until the end of the experiment.

6.1.2. Southern Blot Analysis

Southern blot analysis was performed as described by Reed (1998, *Mamm. Gen.* 9:571-576) on StuI or NdeI/KpnI-digested DNA purified from ES cells or tail biopsies. Briefly, pre-hybridization and hybridization were performed at 65 C in 1% SDS, 1 M NaCl, and 10% dextran sulfate. Blots were screened with a 347 bp PCR-generated probe corresponding to mouse PDE1B exon 3 and 164 bp of flanking intron sequence. PCR primers used were 5'-GACACTAAGTGGG-TATAGCTGGGT-3' (SEQ ID NO: 5) and 5'-GTGG-GAATAAGTCTCAGGGTAGG-3' (SEQ ID NO: 6). Twenty-five ng of probe were radiolabeled with $^{32}$P-dCTP by random priming with the Prime-It II kit (Stratagene, Inc.), boiled with 5 mg/500 µl salmon sperm DNA for 5 minutes, and added to 30 ml of hybridization buffer. Blots were hybridized for 12-16 hours and the final post-hybridization wash was in 2×SSC+ 1% SDS at 65 C. The probe is outside of the targeted region of the PDE1B gene. Homologous recombination events resulted in size shifts from 3.7 to 2.2 kb (Stu1) (see FIGS. 1A, B) and from 3.7 to 10.6 kb (NdeI/KpnI) (see FIG. 1A).

6.1.3. Northern Blot Analysis

Total brain RNA was isolated using the TriReagent method (Molecular Research Center, Cincinnati, Ohio). RNA (10 µg) was fractionated on a 1% denaturing agarose gel and transferred for 24 hours onto a nylon membrane using 20×SSC. The blot was pre-hybridized in 10 ml of solution consisting of 50% formamide, 50 mM NaPO$_4$, 5×SSC, 5×Denhardt's, 0.5% SDS, and 1% glycine with 250 µl of 10 mg/ml salmon sperm DNA at 42 C for 4 hours. The blot was hybridized with $^{32}$P-labeled probe K-17, a 348 bp mouse partial PDE1B cDNA corresponding to the central catalytic domain as described by Repaske et al. (1992. *J. Biol. Chem.* 267:18683-18688). The probe was boiled for 5 minutes with 100 µl of 10 mg/ml salmon sperm DNA, added to 10 ml of the hybridization buffer of 50% formamide, 20 mM NaPO$_4$, 5×SSC, 1×Denhardt's, 0.5% SDS, and 10% dextran sulfate, and incubated at 42° C. for 21 hours. The final post-hybridization wash was in 0.1×SSC+0.1% SDS at 55° C.

6.1.4. Determination of Locomotor Activity

On P50, P51, or P52, locomotor activity was measured in a 30.5 cm×30.5 cm Digiscan apparatus containing sixteen photo-detector-LED pairs along the X-axis and sixteen pairs along the Y-axis (Model RXY2Z, Accuscan Electronics, Columbus, Ohio). Pre-challenge activity was recorded in 3 minute intervals over a one hour period. Mice were challenged with a subcutaneous injection of 1 mg/kg d-methamphetamine hydrochloride (free base) mixed in saline to yield an injection volume of 5 ml/kg body weight and activity was recorded for an additional two hours at three minute intervals. Recording was done during the light cycle. Horizontal activity and total, center and margin distance were measured.

6.1.5. Determination of Locomotor Activity and Learning Behaviors with a Morris Maze On P50, all animals within a litter were administered four timed trials in a 15×244 cm straight water channel with a wire ladder at one end. The channel was constructed on PVC material and filled with 27 to 29° C. water at a depth of 35 cm. Subjects were placed in the channel at the opposite end from the ladder and given a maximum of 60 seconds to find the ladder and escape. These trials were used to measure swimming proficiency and motivation to escape from water prior to Morris water maze trials. Two litters of mice were excluded from further behavioral testing due to poor swimming performance.

The Morris water maze was used with modifications for mice (Upchurch, M. and J. M. Wehner. 1988. *Behav. Gen.* 18:55-68). The maze was a circular, stainless steel perimeter of 122 cm in diameter that was surrounded by an outer tank 162 cm in diameter. The inner perimeter was covered with flat white paint. The clear acrylic platform was 10×10 cm and submerged 1 cm below the surface of the water. White non-toxic paint was added to the water to camouflage the platforms. Water temperature was maintained at 27 to 29° C. Litters were divided into two groups to balance for platform position. Testing began on P51 and continued for 18 days with 6 days each for hidden-platform acquisition and reversal (with platform moved to the opposite quadrant), and followed by cued learning. For hidden-platform acquisition, the platform was placed in the SE or NW quadrant and start positions (N, S, E, or W) were altered on every trial in a random sequence. Four trials were given each day with a maximum time limit of 60 seconds and inter-trial intervals of 30 seconds. Mice not finding the platform in 60 seconds were placed on the platform for the second inter-trial interval. Probe trials (60 seconds) were given on day 3 before acquisition trials and day 6 after the last acquisition trial with the platform removed. For the reversal phase, the same procedure was followed with the platform shifted to the opposite quadrant. For cued learning, black curtains were drawn around the maze to obscure distal cues and the platform was marked by a black solid cylinder (5×7 cm) mounted on a 14 cm brass rod above the platform. Four trials per day were given with the platform and start positions randomly located for each trial. Mice were placed in a holding cage for the 30 second inter-trial interval while the platform was positioned for the next trial. Data were recorded for acquisition and reversal phases using a video tracking system (San Diego Instruments, San Diego, Calif.). Cued acquisition latencies were recorded with a hand-held timer and observed on a closed-circuit monitor.

6.1.6. Olfactory Orientation

On P9, P11 and P13, all offspring in each litter were tested individually for olfactory orientation to their home cage scent as described previously (Acuff-Smith et al, 1992. Psychopharmacology 109:255-263). Each litter's home bedding was changed on P7. The bedding was not changed again until after testing was completed on P14 and was used each test day and then returned to the home cage. Prior to individual testing, pups were removed from the dam and placed in a holding cage on a heating pad to maintain body temperature.

6.1.7. Preparation and Treatment of Striatal Slices

Neostriatal slices were prepared from male C57/BL6 mice (6-8 weeks old) in accordance with methods known in the art (Nishi, A. et al. 1997. *J. Neurosci.* 17:8147-8155).

Male PDE1B−/− (null) and WT mice (8-12 weeks of age) were decapitated. The brain was transferred rapidly to an ice-cold surface, blocked, and fixed to the cutting surface of a Vibratome (Ted Pella, Redding, Calif.) maintained at 4° C. The brain was submersed in cold, oxygenated (95% O$_2$/5%

$CO_2$) Krebs' bicarbonate buffer of the following composition (in mM): 125 NaCl, 5KCl, 26 $NaHCO_3$, 1.5 $CaCl_2$, 1.5 $MgSO_4$, and 10 glucose, pH 7.4. Coronal mouse brain sections (400 µm in thickness) were cut and pooled in cold buffer. Striatal or nucleus accumbens slices were cut from the coronal sections under a dissecting microscope. Individual slices were preincubated in fresh buffer for 15 min at 30° C.; the buffer was replaced, and preincubation continued for an additional 30 min. At the end of this second preincubation period the buffer was replaced with Krebs' buffer or buffer containing test substances for 5 min. Slices were frozen immediately in liquid nitrogen and stored at −80° C. until assayed.

6.1.8. Immunoblotting

Frozen slices were sonicated in homogenization buffer containing 1% SDS. Small aliquots of the homogenate were retained for protein determination by standard assays using bovine serum albumin as the standard. Equal amounts of protein (50 µg) were loaded onto 10% acrylamide gels, separated by SDS/PAGE, and transferred to nitrocellulose membranes by a method described by Tobin et al. (1979. *Proc. Natl. Acad. Sci, USA* 76:4350-4354). Membranes were immunoblotted with the following antibodies: an antiserum detecting the Ser845-phosphorylated form of GluR1 (Kameyama, K. et al. 1998. *Neuron* 21:1163-1175), an antiserum detecting the C-terminal region of GluR1 irrespective of phosphorylation state (Pharmingen, Inc.), mAb23 which is a phosphorylation-specific antibody detecting a DARPP-32 peptide containing phospho-Thr34 (Snyder, G. L. et al. 1992. *J. Neurosci.* 12:3071-3083), the site phosphorylated by PKA, or C24-5a which is a monoclonal antibody detecting DARPP-32 irrespective of phosphorylation state (Hemmings, H. C. and P. Greengard. 1986. *J. Neurosci.* 6:1469-1481).

Antibody binding was revealed by incubation with either a goat anti-rabbit horseradish peroxidase-linked TgG or a goat anti-mouse horseradish peroxidase-linked IgG and the ECL immunoblotting detection system (Amersham Biosciences). Chemiluminescence was detected by autoradiography and bands were quantified by analysis of scanned images using NIH Image 1.52 software. Because the linear range for quantitation of ECL signals by densitometry is limited, several film exposures were obtained for each set of samples to insure that the signals were within a density range that allowed for accurate quantitation.

6.1.9. Statistical Methods

Data were analyzed via ANOVA (general linear model). For data that had repeated measure components, split plot ANOVAs were used, with day and trial treated as within-subject factors in the analyses (Kirk, 1995). Data were averaged within a litter for each genotype having more than one subject of the same gender (Holson and Pearce, 1992). Significant interactions were analyzed further by using simple-effect ANOVA. A posteriori group comparisons were performed by the method of Duncan. Analyses for time-dependent interactions were performed on activity data, using trend analyses by orthogonal decomposition. $\chi^2$ was used to analyze whether the proportion of mice of each genotype matched predicted Mendelian ratios. Neostriatal slice data were analyzed by a Mann-Whitney U test, as indicated, with significance defined as $p<0.05$.

6.2. Results and Discussion

A mouse model was developed wherein the PDE1B enzyme was rendered inactive by targeted disruption of the catalytic domain. These "knockout" mice were used in studies to identify the functional significance of PDE1B activity in vivo in brain. To generate the mice deficient in PDE1B activity, a targeting vector was constructed in order to disrupt the sequences encoding the PDE1B catalytic domain in mouse embryonic stem cell genomic DNA by homologous recombination (FIG. 1A). Of the 302 embryonic stem cell colonies that survived HAT and Cytovene selection, 26 were analyzed by Southern blot using a probe corresponding to PDE1B exon 3 and the flanking intron sequence. The disrupted gene was present in 9 of the clones.

Two recombinant embryonic stem cell lines were microinjected into day E3.5 C57B1/6 blastocysts and implanted in pseudopregnant females. Twenty-eight chimeras were generated (17 males and 11 females) and 8 or 29% from one embryonic stem cell line demonstrated germline transmission when bred to C57B1/6 mice. Third generation heterozygous mice were interbred resulting in 178 wild-type mice (27%), 309 heterozygous mice (47%), 157 PDE1B null mice (24%) and 13 mice that died before being genotyped (2%). These proportions did not differ significantly from the expected Mendelian ratio of 1:2:1 by 2 analysis. A Southern blot demonstrating F4 genotypes is shown in FIG. 1B.

The physical appearance and general behavior of PDE1B null and heterozygous mice was identical to that of the wild-type litter mates. There were no significant differences in either pre-weaning or post-weaning weights among the three genotypes. More PDE1B null mice (6%) and heterozygous mice (6%) died within one week following birth compared to wild-type mice (2%). A Northern blot analysis of total brain RNA probed with K-17, a 348 base pair mouse partial PDE1B cDNA within the targeted domain (Repaske, D. R. et al. 1992. *J. Biol. Chem.* 267:18683-18688), demonstrated a reduction in PDE1B mRNA in the heterozygous mice and the absence of PDE1B mRNA in the null mice, confirming the successful production of knockout mice for the PDE1B gene (FIG. 1C). Further, the PDE1B mRNA levels were decreased in the mice with no apparent upregulation of the normal allele in the heterozygous mice. Immunoprecipitation of PDE1B from whole mouse brain demonstrated absence of PDE1B enzymatic activity in the null mice when assayed for cAMP hydrolysis. The heterozygote mice demonstrated 50% of the activity level seen in wild-type mice.

In order to examine the functional significance of the PDE1B gene and its expression in brain tissue, the locomotor activity of the knockout mice was studied using a series of standard locomotor activity tests in mice, tests that are used routinely to define effects of test conditions or therapeutics on locomotion and then to extrapolate the results to expected results in humans. Such tests are a standard part of the drug development process.

Both exploratory and methamphetamine-stimulated activity were studied in null (knockout), heterozygous, and wild-type mice. The predominant effect of genotype was observed on horizontal locomotor activity where there were significant differences among the mice in terms of both pre-challenge exploratory activity and post-challenge exploratory activity. There was also a significant genotype by interval interaction observed both pre-challenge and post-challenge for horizontal activity tests. ANOVA analysis revealed that pre-challenge, heterozygous mice showed activity levels comparable to that of the wild-type mice (FIG. 2), whereas PDE1B null mice (knockout mice) exhibited significantly more exploratory behavior, especially during the first 30 minutes of the test period. From 30 to 60 minutes, the PDE1B null mice habituated towards wild-type activity levels but still remained slightly more active. ANOVA analysis and group comparisons of post-challenge horizontal activity revealed that the heterozygous mice were slightly, though not significantly different from wild-type mice in terms of activity levels. In contrast, PDE1B null mice were significantly more active than wild-type mice. The stimulated hyperactivity response lasted for 90 minutes after methamphetamine treatment. This can be seen in FIG. 2 by the sharper rise in activity over the same time period in PDE1B−/− mice after METH than occurred in WT mice.

In order to determine if the stimulated response of the PDE1B null mice was qualitatively as well as quantitatively different from the control, wild-type mouse response, a trend analysis using orthogonal decomposition was performed. Null to wild-type comparisons showed significant linear, quadratic, and cubic trends for the genotype by interval interaction; heterozygous to wild-type interactions did not show any significant effects. In the null to wild-type comparison, the quadratic trend best fit the data, revealing that the null mice were not only more active but also had a greater rate of change than the wild-type mice in response to methamphetamine, indicating a faster rate of response in the mice.

Figure 3:
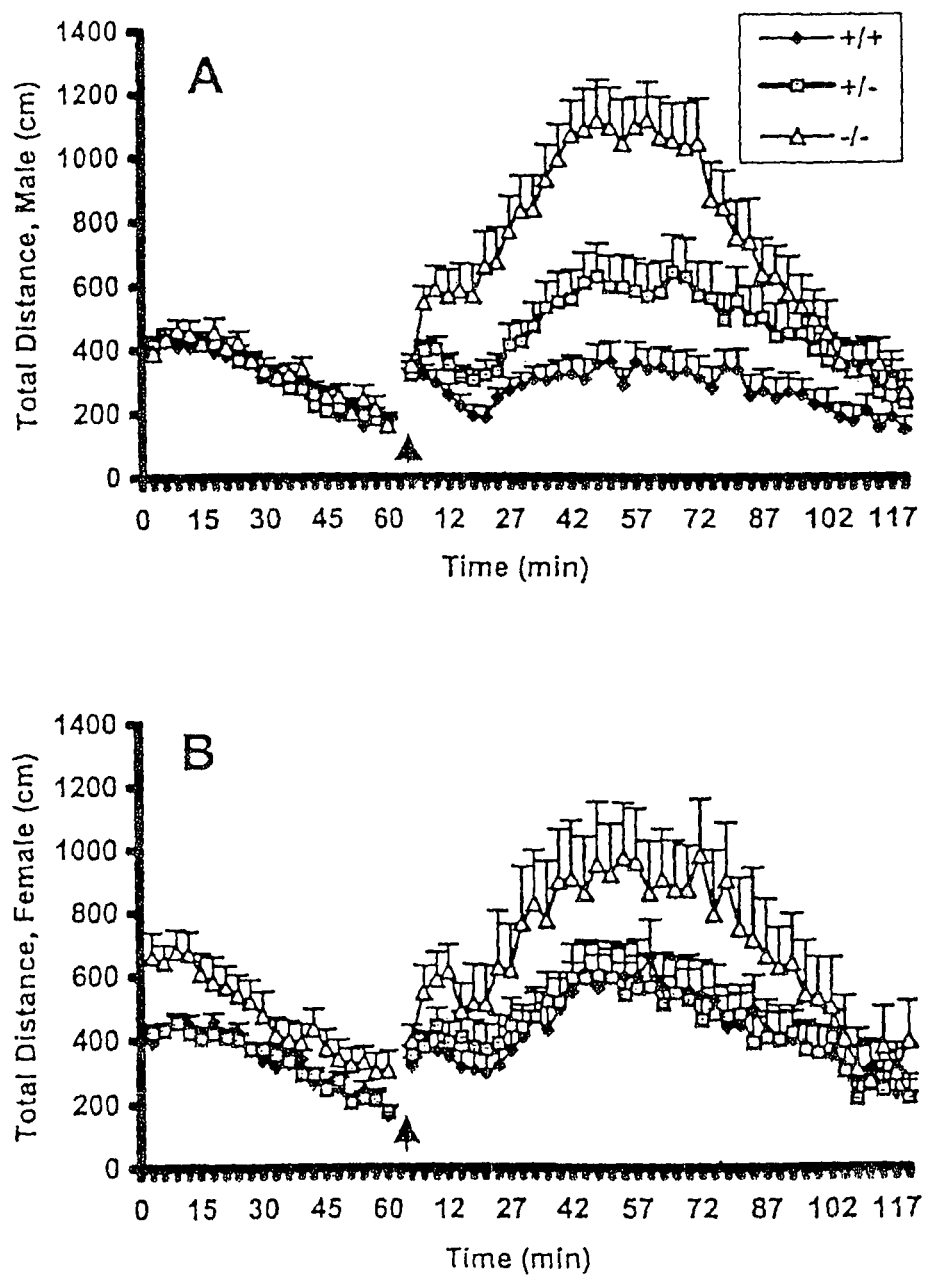

When the endpoint of total distance was examined, the same pattern of responses as were seen with horizontal activity resulted. As with the measures of horizontal activity, there was a significant main effect of genotype both pre-challenge and post-challenge. PDE1B null mice traveled greater total distances as compared to wild-type mice in both the pre-challenge and post-challenge periods. A genotype by interval interaction was also observed for both pre-challenge and post-challenge and the pattern was identical to that seen with horizontal activity measures. There was one difference in the results identified for measures of total activity as compared to the results of horizontal activity. This was that there was a genotype by sex interaction seen in the pre-challenge period. Null females only showed a hyperactive response in terms of total activity while null males did not exhibit a significant increase in total activity pre-challenge (FIG. 3). However, after methamphetamine challenge, both null males and females showed stimulated hyperactivity as compared to wild-type mice. There appeared to be a slightly greater total response in male null mice, although the results were not statistically significant. Male heterozygous mice also showed an intermediate response to methamphetamine challenge that although not statistically different from male wild-type mice suggested a subtle gene-dose effect. Distance data were further analyzed in terms of central and margin activity; both analyses showed the same significant effects and interactions as were observed with measures of total distance.

Next, locomotor activity was tested in straight channel and cued acquisition of a Morris water maze. In the straight channel trials, used to determine swimming performance, there were no significant differences observed among the three genotypes, with all mice demonstrating equal swimming ability and motivation to escape. Similarly, there were no main effects or interactions found for cued learning when proximal cues were present and distal cues removed from the Morris water maze.

Spatial learning and memory were then tested in a hidden platform Morris water maze test. The results showed that in acquisition of the Morris water maze, both heterozygous mice and PDE1B null mice had significantly longer path length than wild-type mice (FIG. 5A). A significant day by genotype by platform interaction was also found. Although wild-type mice tested with the platform in both quadrants had shorter path length than heterozygous or PDE1B null mice, the interaction was the product of the fact that the effect was larger on days 3 through 6 (in the southeast quadrant). A significant trial by genotype by sex effects on path length was also observed but the contribution of gender appeared to be minor. The same pattern was seen when latency was examined. As with the other measures, the effect was larger for one goal quadrant than the other (the southeast). The null and heterozygous mice had significantly longer latencies than wild-type mice on days 3 and 4. A trial by genotype by sex interaction was observed, but as before the contribution of sex was minor.

Figure 5:
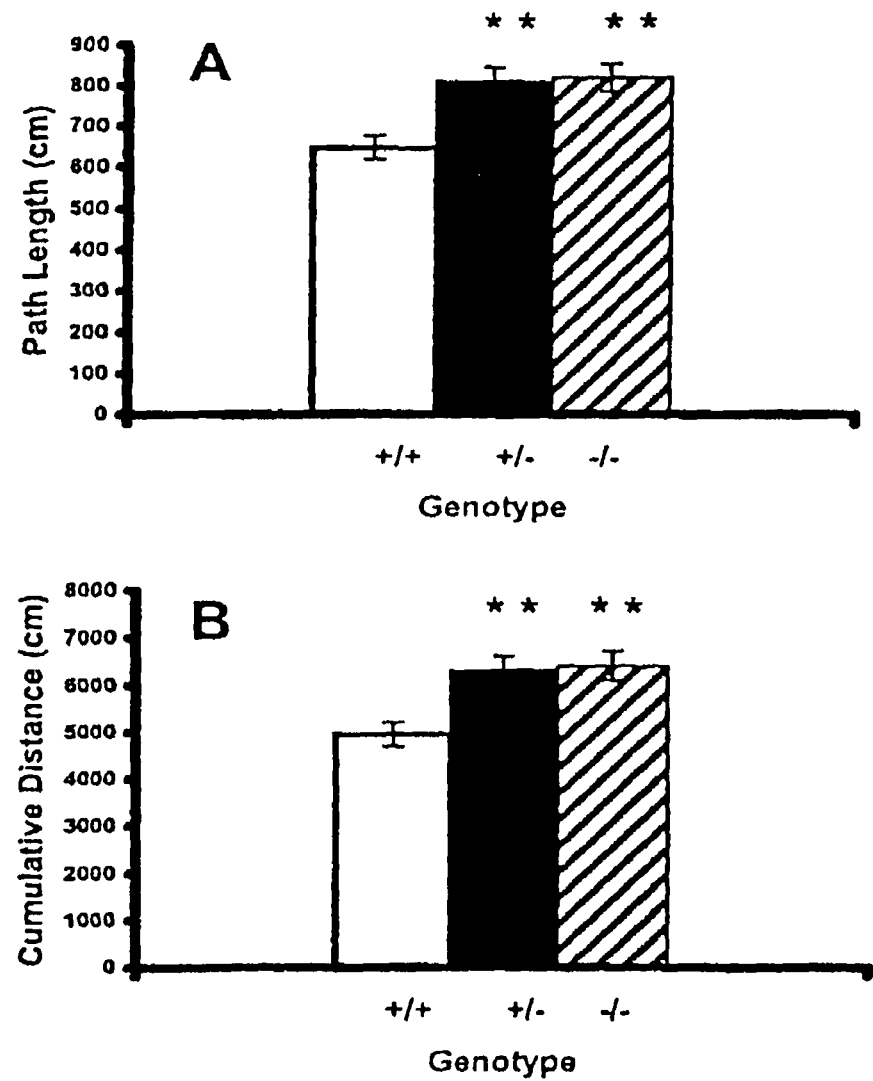

When the learning curves for the test were examined, the patterns for cumulative distance and latency were similar among groups (FIGS. 5 and 6). All groups showed similar performance on day 1, indicating that no pre-existing performance differences among the genotypes was present. On subsequent days, wild-type mice showed steady improvement, requiring shorter paths to the goal on each successive day of testing. Null and heterozygous mice, in contrast, showed less improvement each day than their wild-type controls, resulting in significant differences on test days 3 through 6. Even after 24 trials on day 6, null and heterozygous mice were not performing comparably to wild-type mice.

Probe trial measurements of path length and dwell time in the target zone were analyzed two ways. First, these data were analyzed by annuli: one annulus containing the target platform sites, one outside the outer edge of the platform and one inside the inner edge of the platform. Secondly, probe trial data were analyzed by dividing the maze into four equal quadrants. Overall, null and heterozygous mice swam significantly less in the target annulus than wild-type mice (FIG. 7A). A significant genotype by platform position interaction was found in both the target annulus and the outer annulus. Again, null mice and heterozygous mice swam less in the target annulus, an effect that was most pronounced in the southeast condition as compared to wild-type mice. Conversely, null mice and heterozygous mice swam significantly more in the outer annulus than wild-type mice (FIG. 7B). No significant difference was found in path length within the inner annulus, dwell times, or platform crossings. A significant interaction of day by genotype by platform position was found for average distance from the target in which heterozygous mice were significantly farther from the target site than wild-type mice. In addition, heterozygous mice had significantly shorter dwell times than wild-type mice. There were no differences in time or distance due to quadrants.

For reversal testing, no significant differences were found for the measures of path length or cumulative distance. A trial by genotype interaction was observed for latency in which the null mice had significantly longer latencies than wild-type mice on trial 24 of the testing. No significant differences were found on reversal probe trials. In addition, no significant differences were found among the three genotypes in terms of olfactory orientation.

Figure 4:
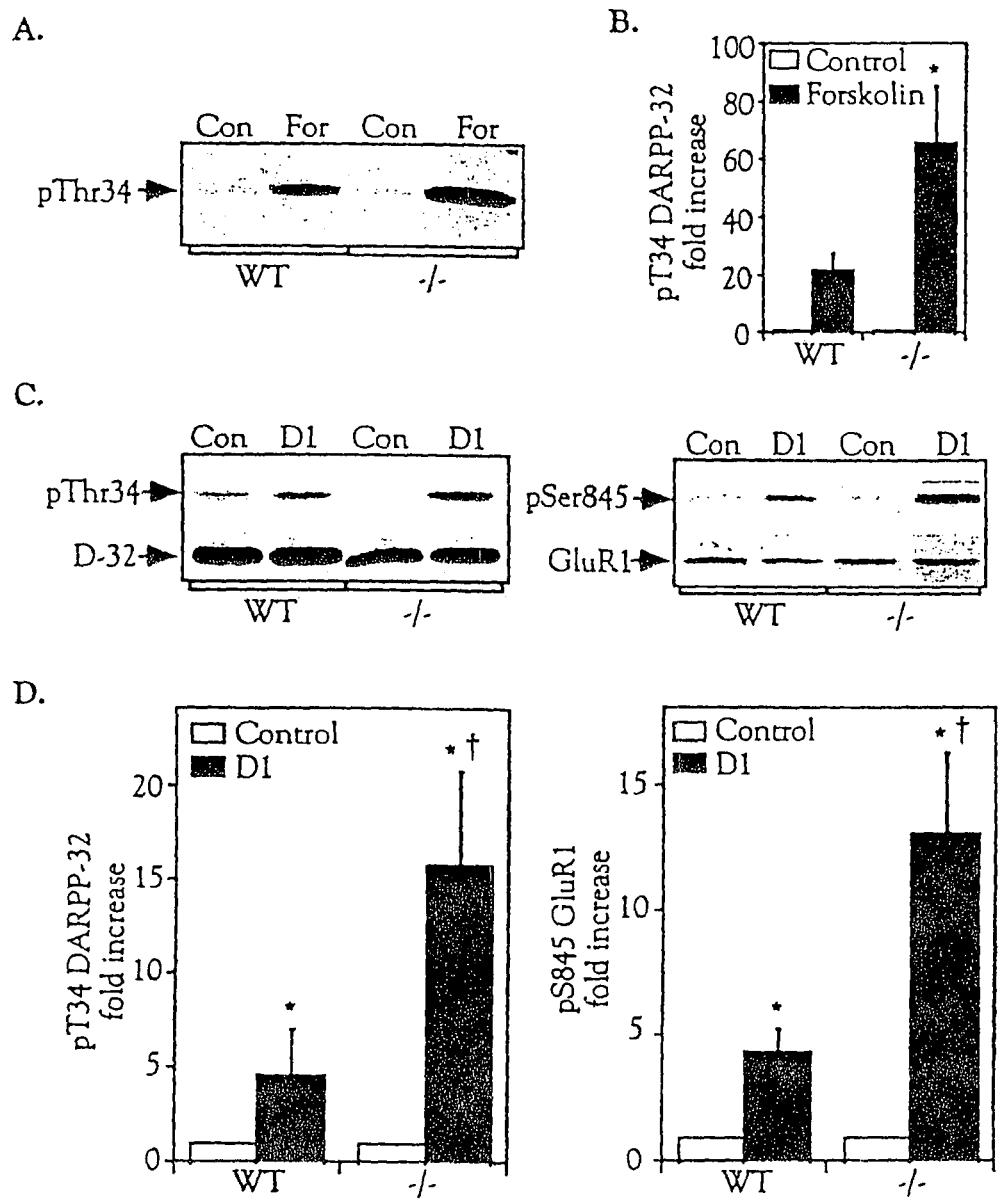

Experiments were then performed to determine whether mice lacking the PDE1B gene (PDE1B null mice) would exhibit functional enhancement of PKA-mediated protein phosphorylation. Striatal brain slices were prepared from male wild-type and male PDE1B null mice. The slices were then exposed to a dopamine D1-type receptor agonist, SKF81297 (10 µM), for 10 minutes. The effect of treatment on phosphorylation of DARPP-32 at Thr34 and the GluR1 AMPA receptor at Ser845 was measured using phosphorylation state-specific antibodies (FIGS. 4C, D); these substrates have been shown to be regulated by activation of D1 receptors and PKA (Greengard, P. et al. 1999. Neuron 23:435-447). Dopamine receptor agonist treatment increased levels of phospho-Thr34 DARPP-32 by 4 to 5 fold in striatal slices of wild-type mice as compared to control mice (no treatment with agonist), while agonist treatment increased levels of phospho-Ser845 also by 4 to 5 fold as compared to controls (no treatment with agonist) (FIG. 4D). When striatal slices from wild-type mice and PDE1B null mice were treated with D1 receptor agonist, levels of both phospho-Thr34 and phospho-Ser845 were significantly increased in PDE1B null mice as compared to controls (15-fold increase for phospho-Thr34 and 13-fold increase for phospho-Ser845) (FIG. 4D). In addition, there was an enhanced D1-mediated phosphorylation observed in nucleus accumbens slices from PDE1B null mice as compared to wild-type mice. Interestingly, there were no significant differences in basal levels of phospho-Thr34, phospho-Ser845, or total levels of DARPP-32 or GluR1 when untreated striatal (FIG. 4C) or accumbens slices from PDE1B null mice were compared with striatal or accumbens slices from wild-type mice.

Forskolin (10 a direct activator of adenylyl cyclase, also was used to increase cAMP levels in striatal slices from PDE1B null and wild-type mice (FIG. 4A). Forskolin treatment induced a significantly greater increase in levels of phospho-Thr34 DARPP-32 and phospho-Ser845 GluR1 in striatal slices from PDE1B null mice (65-fold increase) when compared with wild-type mice (21-fold increase) (FIG. 4B).

These data have demonstrated that mice lacking PDE1B activity have significantly increased spontaneous and methamphetamine-induced locomotor activity as compared to wild-type and heterozygous mice. The biochemical data presented demonstrate that these alterations in PDE1B-deficient mouse behavior are likely a consequence of disruption of striatal pathways in brain, pathways that are the predominant regulators of locomotor activity in animals, including humans. The behavioral changes observed in the PDE1B-deficient mice were observed in response to a novel environment (exploration) and in response to an acute drug challenge (methamphetamine). In addition, the data showed that PDE1B-deficient mice habituated to the environment before being given the methamphetamine challenge as shown by the fact that there was no significant difference from wild-type animals in the last 15 minutes of the pre-challenge period. Thus, the PDE1B-deficient mice showed an increased level of activity in response to methamphetamine challenge that was not due to previous pre-challenge activity levels.

It is well-established that locomotor activity is a standard method for testing the effects of neurotoxicants and psychostimulants. Many drugs, such as cocaine and amphetamines have been shown to affect locomotor activity through regulation of dopaminergic signaling in the brain (Traficante, L. et al. 1976. *Life Sci.* 19:1061-1066). These drugs are known to bind to the dopamine transporter in brain, which results in dopamine overflow and increased ligand binding to dopamine receptors, which in turn results in activation of adenylyl cyclase and an increase in intracellular levels of cAMP (Giros, B. et al. 1996. *Nature* 379: 606-612). Increased intracellular levels of cAMP in turn activate PKA to phosphorylate cellular proteins including proteins such as DARPP-32 and CREB (Cunningham, S. and A. Kelley. 1993. *J. Neurosci.* 13:2342-2350; Konradi, C. et al. 1994. *J. Neurosci.* 14:5623-5634; Misrendino, M. and E Nestler. 1995. *Brain Res.* 674: 299-306). Dopamine binding to D1 receptors also increases intracellular levels of cGMP and leads to activation of PKG and phosphorylation of DARPP-32 as well as other proteins (Altar, C. et al. 1990. *Eur. J. Pharmacol.* 181:17-21; Tsou, K. et al. 1993. *Proc. Natl. Acad. Sci. USA* 90:3462-3465). Alterations of this pathway cause changes in levels of locomotor activity as has been shown in numerous studies involving mice lacking dopamine, dopamine receptors, dopamine transporter, or DARPP-32.

With the present data showing that PDE1B-deficient (null) mice had increased levels of activity in comparison to wild-type mice and even greater increases in activity with an acute methamphetamine challenge, as well as the biochemical data, it is demonstrated that by removing PDE1B cyclic nucleotide hydrolyzing ability, the magnitude and duration of dopamine receptor-generated increases in cyclic nucleotides has been increased.

Considered together, these data have demonstrated that PDE1B activity is involved in locomotion through activity in the striatal pathways of the brain, as well as in learning. The significant effects seen in PDE1B-deficient mice indicate that PDE1B is an important regulator of locomotor activity as well as learning in the brain. The biochemical data demonstrating that basal phosphorylation is unaffected in PDE1B knockout mice, while D1 receptor-mediated phosphorylation of DARPP-32 and GluR1 was enhanced in the PDE1B-deficient or knockout mice supports the finding that PDE1B is involved in learning and locomotion through alterations of the PDE1B signaling pathway.

Based on the understanding that PDE1B has a role in dopamine signaling in the brain, specifically in areas known to be associated with locomotion and learning, according to the present invention, PDE1B represents a novel target for development of new drugs that could be used to treat a variety of diseases that would include, but not be limited to, Parkinson's disease, Huntington's disease, attention deficit disorder (ADD), attention deficit hyperactivity disorder (ADHD), neurodegenerative disorder, Tourette's syndrome, tic disorder, Lesch-Nyans disease, pain, dystonias, substance or drug abuse, schizophrenia, schizoaffective disorder, depression, affective disorder, manic-depressive disorder, obsessive-compulsive disorder, eating disorder, emesis, panic disorder, anxiety disorder, migraine, myoclonus, premenstrual syndrome (PMS), post-traumatic stress syndrome, carcinoid syndrome, Alzheimer's disease, stroke, epilepsy, sleep or circadian rhythm disorder (e.g., insomnia), sexual disorder, stress disorder, hypertension and cancer.

6.3. References

Abel T, Nguygen P V, Barad M, Deuel T A, Kandel E R, Bourtchuladze R (1997) Genetic demonstration of a role for PKA in the late phase of LTP, in hippocampus-based long-term memory. Cell 88:615-626.

Acuff-Smith K D, George M, Lorens S A, Vorhees C V (1992) Preliminary evidence for methamphetamine-induced behavioral and ocular effects in rat offspring following exposure during early organogenesis. Psychopharmacology 109: 255-263.

Altar C, Boyar W, Kim H (1990) Discriminatory roles for D1 and D2 dopamine receptor subtypes in the in vivo control of neostriatal cyclic GMP. Eur J Pharmacol 181:17-21.

Bach M E, Hawkins R D, Osman M, Kandel E R, Mayford M (1995) Impairment of spatial but not contextual memory in CaMKII mutant mice with selective loss of hippocampal LTP in the range of the theta frequency. Cell 81:905-915.

Balk J-H, Picetti R, Salardi A, Thirlet G, Dierich A, Depaulis A, LeMeur M, Borrelli E (1995) Parkinsonian-like locomotor impairment in mice lacking dopamine D2 receptors. Nature 377:424-428.

Borisy F F, Ronnett G V, Cunningham A M, Julifs D, Beavo J A, Snyder S H (1992) Calcium/calmodulin-activated phosphodiesterase expressed in olfactory receptor neurons. J Neurosci 12:915-923.

Bourtchuladze R, Frenguelli B, Blendy J, Cioffi D, Schutz G, Silva A J (1994) Deficient long-term memory in mice with a targeted mutation of the cAMP-responsive element-binding protein. Cell 79:59-68.

Cunningham S, Kelley A (1993) Hyperactivity and sensitization to psychostimulants following cholera toxin infusion into the nucleus accumbens. J Neurosci 13:2342-2350.

Davis R L, Cherry J, Dauwalder B, Han P-L, Skoulakis E (1995) The cyclic AMP system and *Drosophila* learning. Mol Cell Biochem 149-150:271-278.

Devan B D, White N M (1999) Parallel information processing in the dorsal striatum: relation to hippocampal function. J Neurosci 19:2789-2798.

Devan B D, Goad E H, Petri H L (1996) Dissociation of hippocampal and striatal contributions to spatial navigation in the water maze. Neurobiol Learn Mem 66:305-323.

Devan B D, McDonald R J, White N M (1999) Effects of medial and lateral caudate-putamen lesions on place- and cue-guided behaviors in the water maze: relation to thigmotaxis. Behav Brain Res 100:5-14.

D'Hooge R, De Deyn P P (2001) Applications of the Morris water maze in the study of learning and memory. Brain Res Rev 36:60-90.

Drago J, Gerfen C, Lachowicz J, Steiner H, Hollon T, Love P, Ooi G, Grinberg A, Lee E, Huang S, Bartlett P, Jose P, Sibley D, Westphal H (1994) Altered striatal function in a mutant mouse lacking D1A dopamine receptors. Proc Natl Acad Sci USA 91:12564-12568.

Engels P, Abdel'Al S, Hulley P, Lubbert H (1995) Brain distribution of four rat homologues of the *Drosophila* dunce cAMP phosphodiesterase. J Neurosci Res 41:169-178.

Erneux C, VanSande J, Miot F, Cochaux P, Decoster C, Dumont J (1985) A mechanism in the control of intracellular cAMP level: the activation of a calmodulin-sensitive phosphodiesterase by a rise of intracellular free calcium. Cell Endocrinol 43:123-134.

Fienberg A A, Hiroi N, Mermelstein P G, Song W J, Snyder G L, Nishi A, Cheramy A, O'Callaghan J P, Miller D B, Cole D G, Corbett R, Haile C N, Cooper D C, Onn S P, Grace A A, Ouimet C C, White F J, Hyman S E, Sumicier D J, Girault J-A, et al (1998) DARPP-32: regulator of the efficacy of dopaminergic neurotransmission. Science 281:838-842.

Furtado J C S, Mazurek M F (1996) Behavioral characterization of quinolinate-induced lesions of the medial striatum: relevance for Huntington's disease. Exp Neurol 138:158-168.

Furuyama T, Iwashashi Y, Tano Y, Takagi H, Inahaki S (1994) Localization of 63 kDa calmodulin-stimulated phosphodiesterase mRNA in the rat brain by in situ hybridization histochemistry. Mol Brain Res 26:331-336.

Gally J A, Montague P R, Reeke G NJ, Edelman G M (1990) The NO hypothesis: possible effects of a short-lived, rapidly diffusible signal in the development and function of the nervous system. Proc Natl Acad Sci USA 87:3547-3551.

Garthwaite J (1991) Glutamate, nitric oxide, and cell-cell signaling in the nervous system. Trends Neurosci 14:60-67.

Giros B, Jaber M, Jones S R, Wightman R M, Caron M G (1996) Hyperlocomotion and indifference to cocaine and amphetamine in mice lacking the dopamine transporter. Nature 379:606-612.

Greengard P, Allen P B, Nairn A C (1999) Beyond the dopamine receptor: the DARPP-32/protein phosphatase-1 cascade. Neuron 23:435-447.

Guzowski J F, McGaugh J L (1997) Antisense oligodeoxynucleotide mediated disruption of hippocampal cAMP response element binding protein levels impairs consolidation of memory for water maze training. Proc Natl Acad Sci USA 94:2693-2698.

Hemmings H C, Greengard P (1986) DARPP-32, a dopamine- and adenosine 3:5-monophosphate-regulated phosphoprotein: regional, tissue, and phylogenetic distribution. J Neurosci 6:1469-1481.

Hiroi N, Fienberg A, Haile C, Alburges M, Hanson G, Greengard P, Nestler E (1999) Neuronal and behavioural abnormalities in striatal function in DARPP-32 mutant mice. Eur J Neurosci 11:1114-1118.

Holson R R, Pearce B (1992) Principles and pitfalls in the analysis of prenatal treatment effects in multiparous species. Neurotoxicol Teratol 14:221-228.

Houslay M D, Sullivan M, Bolger G B (1998) The multienzyme PDE4 cyclic adenosine monophosphate-specific phosphodiesterase family: intracellular targeting, regulation, and selective inhibition by compounds exerting anti-inflammatory and antidepressant actions. Adv Pharmaco144:225-342.

Jarrard L E (1993) On the role of the hippocampus in learning and memory in the rat. Behav Neural Biol 60:9-26.

Kameyama T, Lee H-K, Bear M F, Huganir R L (1998) Involvement of a postsynaptic protein kinase A substrate in the expression of homosynaptic long-term depression. Neuron 21:1163-1175.

Kirk R E (1995) Experimental design: procedures for the behavioral sciences. Pacific Grove, C A: Brooks/Cole.

Ko G Y, Kelly P T (1999) Nitric oxide acts as a postsynaptic signaling molecule in calcium/calmodulin-induced synaptic potentiation in hippocampal CA1 pyramidal neurons. J Neurosci 19:6784-6794.

Konradi C, Cole R, Heckers S, Hyman S (1994) Amphetamine regulates gene expression in rat striatum via transcription factor C RE B. J Neurosci 14:5623-5634.

Kotter R (1994) Postsynaptic integration of glutamatergic and dopaminergic signals in the striatum. Prog Neurobiol 44:163-196.

Krinks M, Haiech J, Rhoads A, Klee C (1984) Reversible and irreversible activation of cyclic nucleotide phosphodiesterase: separation of the regulatory and catalytic domains by limited proteolysis. In: Advances in cyclic nucleotide and protein phosphorylation research (Strada S J, Thompson W, eds), pp 31-47. New York: Raven.

Laemmli U K (1970) Cleavage of structural proteins during the assembly of the head of bacteriophage T4. Nature 227:680-685.

Lal S, Sharma R K, McGregor C, Macaulay R J B (1999) Immunohistochemical localization of calmodulin-dependent cyclic phosphodiesterase in the human brain. Neurochem Res 24:43-49.

Li H, Zeitler P S, Valerius M T, Small K, Potter S S (1996) GsH-1, an orphan Hox gene, is regulated for normal pituitary development. EMBO J 15:714-724.

Livingstone M S, Sziber P P, Quinn W G (1984) Loss of calcium calmodulin responsiveness in adenylate cyclase of rutabaga, a *Drosophila* learning mutant. Cell 37:205-215.

Ludvig N, Burkmeister V, Jobe P C, Kincaid R L (1991) Electron microscopic immunocytochemical evidence that the calmodulin-dependent cyclic nucleotide phosphodiesterase is localized predominantly at postsynaptic sites in the rat brain. Neuroscience 44:491-500.

Malenka R C, Nicoll R A (1999) Long-term potentiation—a decade of progress? Science 285:1870-1874.

Mansuy I M, Mayford M, Jacob B, Kandel E R, Bach M E (1998) Restricted and regulated overexpression reveals calcineurin as a key component in the transition from short-term to long-term memory. Cell 92:39-49.

Mayer B, Koesling D, Bohme E (1993) Characterization of nitric oxide synthase, soluble guanylyl cyclase, and C2/calmodulin-stimulated cGMP phosphodiesterase as components of neuronal signal transduction. In: Advances in second messenger phosphodiesterase research (Brown B L, Dobson P R M, eds), pp 1.11-119. New York: Raven.

Mayford M, Wang J, Kandel E R, O'Dell T J (1995) CaMKII regulates the frequency-response function of hippocampal synapses for the production of both LTD, LTP. Cell 81:891-904.

Miserendino M, Nestler E (1995) Behavioral sensitization to cocaine: modulation by the cyclic AMP system in the nucleus accumbens. Brain Res 674:299-306.

Monsma F, Mahan L, McVittie L, Gerfen C, Sibley D (1990) Molecular cloning and expression of a D1 dopamine receptor linked to adenylyl cyclase activation. Proc Natl Acad Sci USA 87:6723-6727.

Polli J W, Kincaid R L (1994) Expression of a calmodulin-dependent phosphodiesterase isoform (PDE1B1) correlates with brain regions having extensive dopaminergic innervation. J Neurosci 14:1251-1261.

Qui Y, Davis R L (1993) Genetic dissection of the learning/memory gene dunce of *Drosophila melanogaster*. Genes Dev 7:1447-1458.

Rafales L (1986) Assessment of locomotor activity. In: Neurobehavioral toxicology (Annau Z, ed), pp 54-68. Baltimore: Johns Hopkins U P.

Reed T M, Browning J E, Blough R I, Vorhees C V, Repaske D R (1998) Genomic structure and chromosome location of the murine PDE1B phosphodiesterase gene. Mamm Genome 9:571-576.

Repaske D R, Swinnen N, Jin S-L, VanWyk J J, Conti M (1992) A polymerase chain reaction strategy to identify and clone cyclic nucleotide phosphodiesterase cDNAs. J Biol Chem 267:18683-18688.

Saucier D, Hargreaves E L, Boon F, Vanderwolf C H, Cain D P (1996) Detailed behavioral analysis of water maze acquisition under systemic N MD A or muscarinic antagonism: nonspatial pretraining eliminates spatial learning deficits. Behav Neurosci 110:103-116.

Schenk F (1985) Development of place navigation in rats from weaning to puberty. Behav Neural Biol 43:69-85.

Sharma R K, Wang J (1985) Differential regulation of bovine brain calmodulin-dependent cyclic nucleotide phosphodiesterase isoenzymes by cyclic AMP-dependent protein kinase and calmodulin-dependent phosphatase. Proc Natl Acad Sci USA 82:2603-2607.

Sharma R K, Wang J (1986) Calmodulin and Ca 2-dependent phosphorylation and dephosphorylation of 63 kDa subunit containing bovine brain calmodulin-stimulated cyclic nucleotide phosphodiesterase isozyme. J Biol Chem 261:1322-1328.

Skoulakis E M C, Kalderon D, Davis R L (1993) Preferential expression in mushroom bodies of the catalytic subunit of protein kinase A, its role in learning and memory. Neuron 11:197-208.

Snyder G L, Girault J-A, Chen J Y C, Czemik A J, Kebabian J W, Nathanson J A, Greengard P (1992) Phosphorylation of DARPP-32 and protein phosphatase inhibitor-1 in rat choroid plexus: regulation by factors other than dopamine. J Neurosci 12:3071-3083.

Snyder G L, Fienberg A A, Huganir R L, Greengard P (1998) A dopamine/D1 receptor/protein kinase A/dopamine- and cAMP-regulated phosphorylation (Mr 32 kDa)/protein phosphatase-1 pathway regulates dephosphorylation of the N MD A receptor. J Neurosci 18:10297-10303.

Soderling S H, Bayuga S J, Beavo J A (1999) Isolation and characterization of a dual-substrate phosphodiesterase gene family: PDE10A. Proc Natl Acad Sci USA 96:7071-7076.

Surmeier D J, Bargas J, Hemmings H C, Nairn A C, Greengard P (1995) Modulation of calcium currents by a D1 dopaminergic protein kinase/phosphatase cascade in rat neostriatal neurons. Neuron 14:385-397.

Towbin H, Staehlin T, Gordon J (1979) Electrophoretic transfer of proteins from polyacrylamide gels to nitrocellulose sheets: procedure and some applications. Proc Natl Acad Sci USA 76:4350-4354.

Traficante L, Friedman E, Oleshansky M, Gerson S (1976) Dopaminesensitive adenylate cyclase and cAMP phosphodiesterase in substantia nigra and corpus striatum of rat brain. Life Sci 19:1061-1066.

Tsou K, Snyder G, Greengard P (1993) Nitric oxide/cGMP pathway stimulates phosphorylation of DARPP-32, a dopamine- and cAMPregulated phosphoprotein, in the substantia nigra. Proc Natl Acad Sci USA 90:3462-3465.

Upchurch M, Wehner J M (1988) Differences between inbred strains of mice in Morris water maze performance. Behav Genet 18:55-68.

Wu J, Wang Y, Rowan M J, Anwyl R (1998) Evidence for involvement of the cGMP-protein kinase G signaling system in the induction of longterm depression, but not long-term potentiation, in the dentate gyms. J Neurosci 18:3589-3596.

Xu M, Moratalla R, Gold L, Hiroi N, Koob G, Graybiel A, Tonegawa S (1994) Elimination of cocaine-induced hyperactivity and dopaminemediated neurophysiological effects in dopamine D1 receptor mutant mice. Cell 79:945-955.

Yan C, Bentley J K, Sonnenburg W K, Beavo J A (1994) Differential expression of the 61 kDa and 63 kDa calmodulin-dependent phosphodiesterases in the mouse brain. J Neurosci 14:973-984.

Yan C, Zhao A Z, Bentley J K, Loughrey K, Ferguson K, Beavo J A (1995) Molecular cloning and characterization of a calmodulindependent phosphodiesterase enriched in olfactory sensory neurons. Proc Natl Acad Sci USA 92:9677-9681.

Yan C, Zhao A Z, Bentley J K, Beavo J A (1996) The calmodulin dependent phosphodiesterase gene PDE1C encodes several functionally different splice variants in a tissue-specific manner. J Biol Chem 271:25699-25706.

Yan Z, Surmeier D (1997) D5 dopamine receptors enhance Zn2-sensitive G AB AA currents in striatal cholinergic interneurons through a PKA/PP1 cascade. Neuron 19:1115-1126.

Yin J C P, Wallach J S, Del Vecchio M, Wilder E L, Zhou H, Quinn W G, Tully T (1994) Induction of a dominant negative C RE B transgene specifically blocks long-term memory in *Drosophila*. Cell 79:49-58.

Yuasa K, Kanoh Y, Okumura K, Omori K (2001) Genomic organization of the human phosphodiesterase PDE11A gene. Evolutionary relatedness with other PDEs containing GAF domains. Eur J Biochem 268:168-178.

Zhou Q-Y, Palmiter R D (1995) Dopamine-deficient mice are severely hypoactive, adipsic, and aphagic. Cell 83:1197-1209.

Zola-Morgan S, Squire L R (1993) Neuroanatomy of memory. Annu Rev Neurosci 16:547-563.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. An in vitro method of identifying a compound that inhibits phosphodiesterase 1 B ("PDE1B") activity in a dopamine D1 receptor intracellular signaling pathway by binding to or altering the expression of PDE1B in a cell or tissue expressing dopamine D1 receptor comprising:
   (a) determining a first level of PDE1B activity and Thr34 of DARPP-32 phosphorylation in said cell or tissue;
   (b) contacting said cell or tissue with a test compound; and
   (c) determining a second level of PDE1B activity and Thr34 of DARPP-32 phosphorylation in said cell or tissue, wherein a difference in said first level and said second level of PDE1B activity and Thr34 of DARPP-32 phosphorylation is indicative of the ability of said test compound to modulate PDE1B activity.

2. The method of claim 1 wherein inhibition of PDE1 B modulates phosphorylation of phospho-Thr34 of Dopamine- and cAMP-Regulated Phosphoprotein-32 ("DARPP-32").

3. An in vitro method of identifying a compound that inhibits phosphodiesterase 1 B ("PDE1B") activity in a dopamine D1 receptor intracellular signaling pathway by binding to or altering the expression of PDE1B and Thr34 of DARPP-32 phosphorylation in a cell or tissue expressing dopamine D1 receptor comprising:
   (a) contacting said cell or tissue with a test compound; and
   (b) determining a level of PDE1B activity and Thr34 of DARPP-32 phosphorylation in said cell or tissue;
   wherein a difference in said level and a control level of PDE1B activity and Thr34 of DARPP-32 phosphorylation in a comparable cell or tissue not contacted with the test compound is indicative of the ability of said test compound to modulate PDE1B activity.

4. The method of claim 3 wherein the difference in said level and said control level of PDE1B activity and Thr34 of DARPP-32 phosphorylation is indicative of the ability of said test compound to modulate activity of a dopamine D1 receptor intracellular signaling pathway.

* * * * *

SEQUENCE LISTING

<160> NUMBER OF SEQ ID NOS: 7

<210> SEQ ID NO 1
<211> LENGTH: 204
<212> TYPE: PRT
<213> ORGANISM: Homo sapiens

<400> SEQUENCE: 1

Met Asp Pro Lys Asp Arg Lys Lys Ile Gln Phe Ser Val Pro Ala Pro
1               5                   10                  15

Pro Ser Gln Leu Asp Pro Arg Gln Val Glu Met Ile Arg Arg Arg Arg
            20                  25                  30

Pro Thr Pro Ala Met Leu Phe Arg Leu Ser Glu His Ser Ser Pro Glu
        35                  40                  45

Glu Glu Ala Ser Pro His Gln Arg Ala Ser Gly Glu Gly His His Leu
    50                  55                  60

Lys Ser Lys Arg Pro Asn Pro Cys Ala Tyr Thr Pro Pro Ser Leu Lys
65                  70                  75                  80

Ala Val Gln Arg Ile Ala Glu Ser His Leu Gln Ser Ile Ser Asn Leu
                85                  90                  95

Asn Glu Asn Gln Ala Ser Glu Glu Asp Glu Leu Gly Glu Leu Arg
            100                 105                 110

Glu Leu Gly Tyr Pro Arg Glu Glu Asp Glu Glu Glu Glu Asp Asp
        115                 120                 125

Glu Glu Glu Glu Glu Glu Asp Ser Gln Ala Glu Val Leu Lys Val
    130                 135                 140

Ile Arg Gln Ser Ala Gly Gln Lys Thr Thr Arg Gly Leu Gly Leu Glu
145                 150                 155                 160

Gly Pro Trp Glu Arg Pro Pro Leu Asp Glu Ser Glu Arg Asp Gly
                165                 170                 175

Gly Ser Glu Asp Gln Val Glu Asp Pro Ala Leu Ser Gly Pro Gly Glu
            180                 185                 190

Glu Pro Gln Arg Pro Ser Pro Ser Glu Pro Gly Arg
        195                 200

<210> SEQ ID NO 2
<211> LENGTH: 201
<212> TYPE: PRT
<213> ORGANISM: Mus musculus

<400> SEQUENCE: 2

Met Asp Pro Lys Asp Arg Lys Lys Ile Gln Phe Ser Val Pro Ala Pro
1               5                   10                  15

Pro Ser Gln Leu Asp Pro Arg Gln Val Glu Met Ile Arg Arg Arg Arg
            20                  25                  30

Pro Thr Pro Ala Leu Leu Phe Arg Val Ser Glu His Ser Ser Pro Glu
        35                  40                  45

Glu Glu Glu Glu Glu Ala Ser Pro His Gln Arg Thr Ser Gly Glu Gly
    50                  55                  60

His His Pro Lys Ser Lys Arg Pro Asn Pro Cys Ala Tyr Thr Pro Pro
65                  70                  75                  80

Ser Leu Lys Ala Val Arg Arg Leu Gln Thr Ile Ser Asn Leu Ser Glu
                85                  90                  95

Asn Gln Ala Ser Glu Glu Glu Asp Glu Leu Gly Glu Leu Arg Glu Leu
            100                 105                 110

Gly Tyr Pro Gln Glu Asp Asp Glu Glu Asp Glu Asp Glu Glu Glu Asp

```
             115                 120                 125
Glu Glu Glu Asp Ser Gln Ala Glu Val Leu Lys Gly Ser Arg Gly Thr
    130                 135                 140

Val Gly Gln Lys Leu Leu Val Ala Gly Val Trp Arg Gly Pro Gly Ser
145                 150                 155                 160

Ala His Leu Leu Trp Met Ser Pro Arg Met Glu Thr Leu Arg Thr
                165                 170                 175

Lys Trp Lys Ala Glu Gln His Glx Val Ser Leu Glu Arg Asn Leu Ser
            180                 185                 190

Ile Pro Ala Pro Pro Glu Pro Gly Thr
            195                 200

<210> SEQ ID NO 3
<211> LENGTH: 205
<212> TYPE: PRT
<213> ORGANISM: Rattus sp.

<400> SEQUENCE: 3

Met Asp Pro Lys Asp Arg Lys Lys Ile Gln Phe Ser Val Pro Ala Pro
1               5                   10                  15

Pro Ser Gln Leu Asp Pro Arg Gln Val Glu Met Ile Arg Arg Arg Arg
            20                  25                  30

Pro Thr Pro Ala Leu Leu Phe Arg Val Ser Glu His Ser Ser Pro Glu
        35                  40                  45

Glu Glu Ser Ser Pro His Gln Arg Thr Ser Gly Glu Gly His His Pro
    50                  55                  60

Lys Ser Lys Arg Pro Asn Pro Cys Ala Tyr Thr Pro Pro Ser Leu Lys
65                  70                  75                  80

Ala Val Gln Arg Ile Ala Glu Ser His Leu Gln Thr Ile Ser Asn Leu
                85                  90                  95

Ser Glu Asn Gln Ala Ser Glu Glu Asp Glu Leu Gly Glu Leu Arg
            100                 105                 110

Glu Leu Gly Tyr Pro Asn Glu Asp Asp Glu Asp Glu Asp Glu Asp
        115                 120                 125

Glu Glu Glu Asp Glu Glu Asp Ser Gln Ala Glu Val Leu Lys Gly
    130                 135                 140

Ser Arg Gly Thr Ala Gly Asn Lys Leu Thr Ser Gly Gln Gly Leu Glu
145                 150                 155                 160

Gly Pro Trp Glu Arg Pro Pro Leu Asp Glu Pro Gln Arg Asp Gly
                165                 170                 175

Asn Ser Glu Asp Gln Gly Glu Gly Arg Ala Thr Gln Ser Glu Pro Gly
            180                 185                 190

Glu Glu Pro Arg His Pro Thr Pro Pro Glu Ser Gly Thr
        195                 200                 205

<210> SEQ ID NO 4
<211> LENGTH: 203
<212> TYPE: PRT
<213> ORGANISM: Bovine

<400> SEQUENCE: 4

Met Asp Pro Lys Asp Arg Lys Lys Ile Gln Phe Ser Val Pro Ala Pro
1               5                   10                  15

Pro Ser Gln Leu Asp Pro Arg Gln Val Glu Met Ile Arg Arg Arg Arg
            20                  25                  30

Pro Thr Pro Ala Met Leu Phe Arg Leu Ser Glu His Ser Ser Pro Glu
```

```
            35                  40                  45
Glu Glu Ala Ser Pro His Gln Arg Ala Ser Gly Glu Gly His His Leu
 50                  55                  60
Lys Ser Lys Arg Pro Asn Pro Cys Ala Tyr Thr Pro Pro Ser Leu Lys
 65                  70                  75                  80
Ala Val Gln Arg Ile Ala Glu Ser His Leu Gln Ser Ile Ser Asn Leu
                 85                  90                  95
Gly Glu Asn Gln Ala Ser Glu Glu Asp Glu Leu Gly Glu Leu Arg
            100                 105                 110
Glu Leu Gly Tyr Pro Arg Glu Glu Glu Glu Glu Glu Glu Asp
        115                 120                 125
Glu Glu Glu Glu Glu Asp Ser Gln Ala Glu Val Leu Lys Gly Ser Arg
            130                 135                 140
Gly Ser Ala Gly Gln Lys Thr Thr Tyr Gly Gln Gly Leu Glu Gly Pro
145                 150                 155                 160
Trp Glu Arg Pro Pro Pro Leu Asp Gly Pro Gln Arg Asp Gly Ser Ser
                165                 170                 175
Glu Asp Gln Val Glu Asp Pro Ala Leu Asn Glu Pro Gly Glu Glu Pro
            180                 185                 190
Gln Arg Met Pro Ala His Pro Glu Pro Gly Thr
            195                 200

<210> SEQ ID NO 5
<211> LENGTH: 24
<212> TYPE: DNA
<213> ORGANISM: Artificial Sequence
<220> FEATURE:
<223> OTHER INFORMATION: PCR primer

<400> SEQUENCE: 5
gacactaagt gggtatagct gggt                                          24

<210> SEQ ID NO 6
<211> LENGTH: 23
<212> TYPE: DNA
<213> ORGANISM: Artificial Sequence
<220> FEATURE:
<223> OTHER INFORMATION: PCR primer

<400> SEQUENCE: 6
gtgggaataa gtctcagggt agg                                           23

<210> SEQ ID NO 7
<211> LENGTH: 906
<212> TYPE: PRT
<213> ORGANISM: Homo sapiens

<400> SEQUENCE: 7

Met Gln His Ile Phe Ala Phe Phe Cys Thr Gly Phe Leu Gly Ala Val
 1                   5                  10                  15
Val Gly Ala Asn Phe Pro Asn Asn Ile Gln Ile Gly Gly Leu Phe Pro
                 20                  25                  30
Asn Gln Gln Ser Gln Glu His Ala Ala Phe Arg Phe Ala Leu Ser Gln
             35                  40                  45
Leu Thr Glu Pro Pro Lys Leu Leu Pro Gln Ile Asp Ile Val Asn Ile
 50                  55                  60
Ser Asp Ser Phe Glu Met Thr Tyr Arg Phe Cys Ser Gln Phe Ser Lys
 65                  70                  75                  80
```

```
Gly Val Tyr Ala Ile Phe Gly Phe Tyr Glu Arg Arg Thr Val Asn Met
                 85                  90                  95

Leu Thr Ser Phe Cys Gly Ala Leu His Val Cys Phe Ile Thr Pro Ser
            100                 105                 110

Phe Pro Val Asp Thr Ser Asn Gln Phe Val Leu Gln Leu Arg Pro Glu
        115                 120                 125

Leu Gln Asp Ala Leu Ile Ser Ile Asp His Tyr Lys Trp Gln Lys
    130                 135                 140

Phe Val Tyr Ile Tyr Asp Ala Asp Arg Gly Leu Ser Val Leu Gln Lys
145                 150                 155                 160

Val Leu Asp Thr Ala Ala Glu Lys Asn Trp Gln Val Thr Ala Val Asn
                165                 170                 175

Ile Leu Thr Thr Thr Glu Glu Gly Tyr Arg Met Leu Phe Gln Asp Leu
            180                 185                 190

Glu Lys Lys Lys Glu Arg Leu Val Val Asp Cys Glu Ser Glu Arg
        195                 200                 205

Leu Asn Ala Ile Leu Gly Gln Ile Ile Lys Leu Glu Lys Asn Gly Ile
    210                 215                 220

Gly Tyr His Tyr Ile Leu Ala Asn Leu Gly Phe Met Asp Ile Asp Leu
225                 230                 235                 240

Asn Lys Phe Lys Glu Ser Gly Ala Asn Val Thr Gly Phe Gln Leu Val
                245                 250                 255

Asn Tyr Thr Asp Thr Ile Pro Ala Lys Ile Met Gln Gln Trp Lys Asn
            260                 265                 270

Ser Asp Ala Arg Asp His Thr Arg Val Asp Trp Lys Arg Pro Lys Tyr
        275                 280                 285

Thr Ser Ala Leu Thr Tyr Asp Gly Val Lys Val Met Ala Glu Ala Phe
    290                 295                 300

Gln Ser Leu Arg Arg Gln Arg Ile Asp Ile Ser Arg Arg Gly Asn Ala
305                 310                 315                 320

Gly Asp Cys Leu Ala Asn Pro Ala Val Pro Trp Gly Gln Gly Ile Asp
                325                 330                 335

Ile Gln Arg Ala Leu Gln Gln Val Arg Phe Glu Gly Leu Thr Gly Asn
            340                 345                 350

Val Gln Phe Asn Glu Lys Gly Arg Arg Thr Asn Tyr Thr Leu His Val
        355                 360                 365

Ile Glu Met Lys His Asp Ser Ile Arg Lys Ile Gly Tyr Trp Asn Glu
    370                 375                 380

Asp Asp Lys Phe Val Pro Ala Thr Asp Ala Gln Ala Gly Asp
385                 390                 395                 400

Asn Ser Ser Val Gln Asn Arg Thr Tyr Ile Val Thr Thr Ile Leu Glu
                405                 410                 415

Asp Pro Tyr Val Met Leu Lys Lys Asn Ala Asn Gln Phe Glu Gly Asn
            420                 425                 430

Asp Arg Tyr Glu Gly Tyr Cys Val Glu Leu Ala Ala Glu Ile Ala Lys
        435                 440                 445

His Val Gly Tyr Ser Tyr Arg Leu Glu Ile Val Ser Asp Gly Lys Tyr
    450                 455                 460

Gly Ala Arg Asp Pro Asp Thr Lys Ala Trp Asn Gly Met Val Gly Glu
465                 470                 475                 480

Leu Val Tyr Gly Arg Ala Asp Val Ala Val Ala Pro Leu Thr Ile Thr
                485                 490                 495

Leu Val Arg Glu Glu Val Ile Asp Phe Ser Lys Pro Phe Met Ser Leu
```

```
                500             505             510
Gly Ile Ser Ile Met Ile Lys Lys Pro Gln Lys Ser Lys Pro Gly Val
            515             520             525

Phe Ser Phe Leu Asp Pro Leu Ala Tyr Glu Ile Trp Met Cys Ile Val
            530             535             540

Phe Ala Tyr Ile Gly Val Ser Val Val Leu Phe Leu Val Ser Arg Phe
545             550             555             560

Ser Pro Tyr Glu Trp His Ser Glu Glu Phe Glu Glu Gly Arg Asp Gln
                565             570             575

Thr Thr Ser Asp Gln Ser Asn Glu Phe Gly Ile Phe Asn Ser Leu Trp
            580             585             590

Phe Ser Leu Gly Ala Phe Met Gln Gln Gly Cys Asp Ile Ser Pro Arg
            595             600             605

Ser Leu Ser Gly Arg Ile Val Gly Gly Val Trp Trp Phe Phe Thr Leu
            610             615             620

Ile Ile Ile Ser Ser Tyr Thr Ala Asn Leu Ala Ala Phe Leu Thr Val
625             630             635             640

Glu Arg Met Val Ser Pro Ile Glu Ser Ala Glu Asp Leu Ala Lys Gln
                645             650             655

Thr Glu Ile Ala Tyr Gly Thr Leu Glu Ala Gly Ser Thr Lys Glu Phe
            660             665             670

Phe Arg Arg Ser Lys Ile Ala Val Phe Glu Lys Met Trp Thr Tyr Met
            675             680             685

Lys Ser Ala Glu Pro Ser Val Phe Val Arg Thr Thr Glu Glu Gly Met
            690             695             700

Ile Arg Val Arg Lys Ser Lys Gly Lys Tyr Ala Tyr Leu Leu Glu Ser
705             710             715             720

Thr Met Asn Glu Tyr Ile Glu Gln Arg Lys Pro Cys Asp Thr Met Lys
                725             730             735

Val Gly Gly Asn Leu Asp Ser Lys Gly Tyr Gly Ile Ala Thr Pro Lys
            740             745             750

Gly Ser Ala Leu Arg Asn Pro Val Asn Leu Ala Val Leu Lys Leu Asn
            755             760             765

Glu Gln Gly Leu Leu Asp Lys Leu Lys Asn Lys Trp Trp Tyr Asp Lys
770             775             780

Gly Glu Cys Gly Ser Gly Gly Gly Asp Ser Lys Asp Lys Thr Ser Ala
785             790             795             800

Leu Ser Leu Ser Asn Val Ala Gly Val Phe Tyr Ile Leu Ile Gly Gly
            805             810             815

Leu Gly Leu Ala Met Leu Val Ala Leu Ile Glu Phe Cys Tyr Lys Ser
            820             825             830

Arg Ser Glu Ser Lys Arg Met Lys Gly Phe Cys Leu Ile Pro Gln Gln
            835             840             845

Ser Ile Asn Glu Ala Ile Arg Thr Ser Thr Leu Pro Arg Asn Ser Gly
            850             855             860

Ala Gly Ala Ser Ser Gly Gly Ser Gly Glu Asn Gly Arg Val Val Ser
865             870             875             880

His Asp Phe Pro Lys Ser Met Gln Ser Ile Pro Cys Met Ser His Ser
                885             890             895

Ser Gly Met Pro Leu Gly Ala Thr Gly Leu
            900             905
```